United States Patent
Rudolf et al.

(10) Patent No.: US 6,949,541 B2
(45) Date of Patent: Sep. 27, 2005

(54) SUBSTITUTED PIPERIDINES, MEDICAMENTS CONTAINING THESE COMPOUNDS, AND METHODS FOR THE PRODUCTION THEREOF

(75) Inventors: Klaus Rudolf, Warthausen (DE); Henri Doods, Warthausen (DE); Eckhart Bauer, Biberach (DE); Rudolf Hurnaus, Biberach (DE); Wolfgang Eberlein, Biberach (DE); Alexander Dreyer, Ochsenhausen (DE); Stephan Georg Mueller, Warthausen (DE)

(73) Assignee: Boehringer Ingelheim Pharma KG, Ingelheim (DE)

( * ) Notice: Subject to any disclaimer, the term of this patent is extended or adjusted under 35 U.S.C. 154(b) by 388 days.

(21) Appl. No.: 10/169,009

(22) PCT Filed: Dec. 22, 2000

(86) PCT No.: PCT/EP00/13236

§ 371 (c)(1),
(2), (4) Date: Nov. 7, 2002

(87) PCT Pub. No.: WO01/49676

PCT Pub. Date: Jul. 12, 2001

(65) Prior Publication Data

US 2003/0212057 A1 Nov. 13, 2003

(30) Foreign Application Priority Data

Dec. 30, 1999 (DE) .......................... 199 63 868

(51) Int. Cl.⁷ .................... C07D 401/04; C07D 471/04; A61K 31/445; A61K 38/04; A61P 25/06

(52) U.S. Cl. ................. 514/220; 514/221; 514/266.21; 514/266.22; 514/253.01; 540/495; 540/500; 544/286; 544/360; 544/364

(58) Field of Search ................... 514/220, 221, 514/266.21, 266.22, 253.01; 540/495, 500; 544/286, 360, 364

(56) References Cited

FOREIGN PATENT DOCUMENTS

| DE | 196 36 623 A1 | 3/1998 |
|----|---------------|--------|
| WO | WO 98 11128 A1 | 3/1998 |
| WO | WO 00 18764 A1 | 4/2000 |

OTHER PUBLICATIONS

Doods, H. et al; "Pharmacological Profile of BIBN4096BX, The First Selective Small Molecule CGRP Antagonist", British Journal of Pharmacology, Basingstoke, Hants; Bd. 129, Nr. 3, 2000 420–423 CA 128:230701.

*Primary Examiner*—Bruck Kifle
(74) *Attorney, Agent, or Firm*—Michael M. Morris; Mary-Ellen M. Devlin; Alan R. Stempel

(57) ABSTRACT

The present invention relates to substituted piperidines of general formula

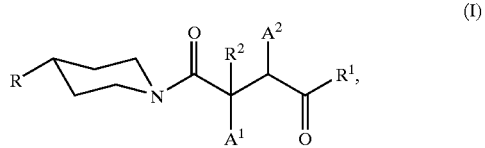

wherein
$A^1, A^2, R, R^1$ and $R^2$ are defined as in claim 1, the tautomers, the diastereomers, the enantiomers, the mixtures thereof and the salts thereof, particularly the physiologically acceptable salts thereof with inorganic or organic acids or bases, which have valuable pharmacological properties, particularly CGRP-antagonistic properties, pharmaceutical compositions containing these compounds, their use and processes for preparing them.

8 Claims, No Drawings

SUBSTITUTED PIPERIDINES, MEDICAMENTS CONTAINING THESE COMPOUNDS, AND METHODS FOR THE PRODUCTION THEREOF

RELATED APPLICATIONS

This application has been derived from International Application PCT/EP00/13226 pursuant to 35 U.S.C. 371.

The present invention relates to new substituted piperidines of general formula

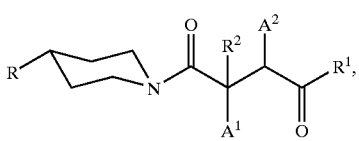

(I)

the tautomers, the diastereomers, the enantiomers, the mixtures thereof and the salts thereof, particularly the physiologically acceptable salts thereof with inorganic or organic acids or bases, pharmaceutical compositions containing these compounds, their use and processes for preparing them.

In the above general formula (I)

R denotes a saturated, mono- or di-unsaturated 5- to 7-membered aza, diaza, triaza, oxaza, thiaza, thiadiaza or S,S-dioxidothiadiaza heterocyclic group, whilst the abovementioned heterocyclic groups are linked via a carbon or nitrogen atom and contain one or two carbonyl groups adjacent to a nitrogen atom, may be substituted by an alkyl group at one of the nitrogen atoms, may be substituted at one or two carbon atoms by an alkyl group, by a phenyl, phenylmethyl, naphthyl, biphenylyl, pyridinyl, diazinyl, furyl, thienyl, pyrrolyl, 1,3-oxazolyl, 1,3-thiazolyl, isoxazolyl, pyrazolyl, 1-methylpyrazolyl, imidazolyl or 1-methylimidazolyl groups, whilst the substituents may be identical or different, and wherein a double bond of one of the above-mentioned unsaturated heterocyclic groups may be fused with a benzene, pyridine, diazine, 1,3-oxazole, thiophene, furan, thiazole, pyrrole, N-methyl-pyrrole or quinoline ring, with a 2(1H)-oxoquinoline ring optionally substituted at the nitrogen atom by an alkyl group or with an imidazole or N-methylimidazole ring or two olefinic double bonds of one of the abovementioned unsaturated heterocyclic groups may each be fused to a benzene ring, whilst the phenyl, pyridinyl, diazinyl, furyl, thienyl, pyrrolyl, 1,3-oxazolyl, 1,3-thiazolyl, isoxazolyl, pyrazolyl, 1-methylpyrazolyl, imidazolyl or 1-methylimidazolyl groups contained in R as well as benzo-, thieno-, pyrido- and diazino-fused heterocyclic groups may additionally be mono-, di- or trisubstituted in the carbon skeleton by fluorine, chlorine or bromine atoms, by alkyl, alkoxy, nitro, alkylthio, alkylsulphinyl, alkylsulphonyl, alkylsulphbnylamino, phenyl, trifluoromethyl, alkoxycarbonyl, carboxy, dialkylamino, hydroxy, amino, acetylamino, propionylamino, aminocarbonyl, alkylaminocarbonyl, dialkylaminocarbonyl, (4-morpholinyl)carbonyl, (1-pyrrolidinyl)carbonyl, (1-piperidinyl)carbonyl, (hexahydro-1-azepinyl)carbonyl, (4-methyl-1-piperazinyl)carbonyl, methylenedioxy, aminocarbonylamino, alkanoyl, cyano, trifluoromethoxy, trifluoromethylthio, trifluoromethylsulphinyl or trifluoromethylsulphonyl groups, whilst the substituents may be identical or different, $R^1$ denotes a phenyl, 1-naphthyl, 2-naphthyl, 1H-indol-3-yl, 1-methyl-1H-indol-3-yl, 1-formyl-1H-indol-3-yl, 4-imidazolyl, 1-methyl-4-imidazolyl, 2-thienyl, 3-thienyl, thiazolyl, 1H-indazol-3-yl, 1-methyl-1H-indazol-3-yl, benzo[b]fur-3-yl, benzo[b]thien-3-yl, pyridinyl, quinolinyl or isoquinolinyl group, whilst the abovementioned aromatic and heteroaromatic groups may additionally be mono-, di- or trisubstituted in the carbon skeleton by fluorine, chlorine or bromine atoms, by alkyl groups, cycloalkyl groups with 3 to 8 carbon atoms, phenylalkyl groups, alkenyl, alkoxy, phenyl, phenylalkoxy, trifluoromethyl, alkoxycarbonyl, carboxy, dialkylamino, nitro, hydroxy, amino, alkylamino, acetylamino, propionylamino, methylsulphonyloxy, aminocarbonyl, alkylaminocarbonyl, dialkylaminocarbonyl, alkanoyl, cyano, tetrazolyl, phenyl, pyridinyl, thiazolyl, furyl, trifluoromethoxy, trifluoromethylthio, trifluoromethylsulphinyl or trifluoromethylsulphonyl groups and the substituents may be identical or different, $R^2$ denotes the hydrogen atom or a $C_{1-3}$-alkyl group, one of the groups $A^1$ and $A^2$ denotes the hydrogen atom and the other denotes the amino, the [1,4']bipiperidinyl-1'-yl or an alkylamino group or the group

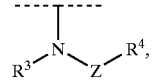

(II)

wherein $R^3$ denotes the hydrogen atom or an alkyl group,

Z denotes the carbonyl or the sulphonyl group and $R^4$ denotes an alkoxy, amino, alkylamino or dialkylamino group, a piperidinyl group optionally substituted by a 1-methyl-4-piperidinyl, 4-methyl-1-piperazinyl or piperidinyl group, a 1-methyl-4-piperidinyloxy group, a pyridinylamino, benzo[b]furanyl, 1,2,4-triazol-1-yl or 1H-indolyl group, a phenyl group optionally substituted by a 4-alkyl-1-piperazinyl or 4-arylalkyl-1-piperazinyl group or a branched or unbranched alkyl group comprising 1 to 7 carbon atoms, which may be substituted in the ω position by an amino, phenyl, pyridinyl, phenoxy, phenylamino, phenylmethoxycarbonylamino or N-alkylphenylamino group, by a dialkylamino group, by a piperidinyl or piperazinyl group optionally substituted by a phenyl, pyridinyl, dimethylamino, 4-morpholinyl, 4-alkyl-hexahydro-1H-1,4-diazepin-1-yl, 4-alkyl-1-piperazinyl, 4-(alkylsulphonyl)-1-piperazinyl, 4-(dialkylaminoalkyl)-1-piperazinyl, 1-alkyl-4-piperidinyl or piperidinyl group, by a 4-methyl-1-piperazinyl group, by an N-($C_{1-3}$-alkyl)-N-(1'-$C_{1-3}$-alkyl-[1,4']bipiperidinyl-1-yl)amino or 4-(1-piperidinylmethyl)-1-piperidinyl group and independently thereof in the α position by an amino, tert.alkoxycarbonylamino or {{{[1,4']bipiperidinyl-1'-yl}-acetyl}amino} group, whilst the abovementioned alkyl and alkenyl groups or the alkyl groups contained in the abovementioned groups, unless otherwise specified, contain 1 to 5 carbon atoms and may be branched or unbranched and the abovementioned aromatic and heteroaromatic groups may additionally be mono-, di- or trisubstituted by fluorine, chlorine or bromine atoms, by cyano or hydroxy groups and the substituents may be identical or different.

The present invention relates to racemates if the compounds of general formula I have only one chiral element. However, the application also includes the individual diastereomeric pairs of antipodes or mixtures thereof which are present if there is more than one chiral element in the compounds of general formula (I), as well as the individual optically active enantiomers of which the abovementioned racemates are composed.

The compounds of general formula (I) have valuable pharmacological properties, based on their selective CGRP-antagonistic properties. The invention further relates to pharmaceutical compositions containing these compounds, their use and the preparation thereof.

Preferred compounds of the above general formula I are those wherein

R denotes a mono- or di-unsaturated 5- to 7-membered aza, diaza, triaza or thiaza heterocyclic group,
  whilst the abovementioned heterocyclic groups are linked via a carbon or nitrogen atom and
  contain one or two carbonyl groups adjacent to a nitrogen atom,
  may be substituted at a carbon atom by a phenyl, pyridinyl, diazinyl, thienyl, pyrrolyl, 1,3-thiazolyl, isoxazolyl, pyrazolyl or 1-methylpyrazolyl group,
  and wherein an olefinic double bond of one of the abovementioned unsaturated heterocyclic groups may be fused to a benzene, pyridine, diazine or quinoline ring or to a 2(1H)-oxoquinoline ring optionally substituted at the nitrogen atom by a methyl group, or two olefinic double bonds of one of the abovementioned unsaturated heterocyclic groups may each be fused to a benzene ring,
    whilst the phenyl, pyridinyl, diazinyl, thienyl, pyrrolyl, 1,3-thiazolyl, isoxazolyl, pyrazolyl or 1-methylpyrazolyl groups contained in R as well as benzo-, pyrido- and diazino-fused heterocyclic groups may additionally be mono-, di- or trisubstituted in the carbon skeleton by fluorine, chlorine or bromine atoms, by alkyl, alkoxy, nitro, trifluoromethyl, hydroxy, amino, acetylamino, acetyl, cyano or trifluoromethoxy groups, whilst the substituents may be identical or different, $R^1$ denotes a phenyl, 1-naphthyl or 2-naphthyl group,
  whilst these aromatic groups may be mono-, di- or trisubstituted by fluorine, chlorine or bromine atoms, by branched or unbranched alkyl groups, by alkoxy, trifluoromethyl, nitro, hydroxy, amino or acetylamino groups, whilst the substituents may be identical or different, $R^2$ denotes the hydrogen atom or the methyl group,
one of the groups $A^1$ and $A^2$ denotes the hydrogen atom and the other denotes the amino, methylamino or ethylamino group, the [1,4']bipiperidinyl-1'-yl group or the group

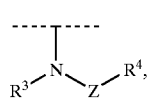

(II)

wherein $R^3$ denotes the hydrogen atom, the methyl or the ethyl group,
  Z denotes the carbonyl or sulphonyl group and
  $R^4$ denotes an alkoxy, amino, alkylamino or dialkylamino group, a 1- or 4-piperidinyl group optionally substituted by a 1-methyl-4-piperidinyl, 4-methyl-1-piperazinyl or 1-piperidinyl group, a 1-methyl-4-piperidinyloxy group, a pyridinylamino, benzo[b]furanyl, 1,2,4-triazol-1-yl or 1H-indolyl group, a phenyl group optionally substituted by a 4-methyl-1-piperazinyl or 4-phenylmethyl-1-piperazinyl group, or a branched or unbranched alkyl group comprising 1 to 7 carbon atoms which may be substituted
    in the ω position by an amino, phenyl, pyridinyl, phenoxy, phenylamino, phenylmethoxycarbonylamino or N-methylphenylamino group, by a dimethylamino group, by a 1-piperidinyl or 1-piperazinyl group optionally substituted by a phenyl, pyridinyl, dimethylamino, 4-morpholinyl, 4-methyl-hexahydro-1H-1,4-diazepin-1-yl, 4-methyl-1-piperazinyl, 4-(methylsulphonyl)-1-piperazinyl, 4-(dimethylaminoalkyl)-1-piperazinyl, 1-methyl-4-piperidinyl or 1-piperidinyl group, by a 4-methyl-1-piperazinyl group, by a N-methyl-N-(1'-methyl-[1,4']bipiperidinyl-1-yl)amino or 4-(1-piperidinylmethyl)-1-piperidinyl group and
    independently thereof in the α position by an amino, tert.butoxycarbonylamino or {{{[1,4']bipiperidinyl-1'-yl}-acetyl}amino} group,
  whilst the abovementioned alkyl groups or the alkyl groups contained in the abovementioned groups, unless otherwise specified, contain 1 to 4 carbon atoms and may be branched or unbranched and the abovementioned aromatic and heteroaromatic groups may additionally be mono-, di- or trisubstituted by fluorine, chlorine or bromine atoms, by cyano or hydroxy groups and the substituents may be identical or different, the tautomers, diastereomers, enantiomers and salts thereof.

Particularly preferred compounds of the above general formula I are those wherein R denotes a mono-unsaturated 5- to 7-membered diaza or triaza heterocyclic group,
  whilst the abovementioned heterocyclic groups are linked via a nitrogen atom,
  contain a carbonyl group adjacent to a nitrogen atom and
  may additionally be substituted at a carbon atom by a phenyl group,
  and wherein an olefinic double bond of one of the abovementioned unsaturated heterocyclic groups may be substituted by a benzene or quinoline ring or by a 2(1H)-oxoquinoline ring optionally substituted at the nitrogen atom by a methyl group, or two olefinic double bonds of one of the abovementioned unsaturated heterocyclic groups may each be fused to a benzene ring,
  whilst the phenyl groups contained in R as well as benzo-fused heterocyclic groups may additionally be mono-, di- or trisubstituted in the carbon skeleton by fluorine, chlorine or bromine atoms, by methyl, methoxy, nitro, trifluoromethyl, hydroxy, amino, acetylamino, acetyl, cyano or trifluoromethoxy groups, whilst the substituents may be identical or different, and are preferably unsubstituted or monosubstituted by a fluorine, chlorine or bromine atom or by a methyl or methoxy group, $R^1$ denotes a phenyl group optionally mono-, di- or trisubstituted by fluorine, chlorine or bromine atoms, by methyl, methoxy, trifluoromethyl, nitro, hydroxy or amino groups, whilst the substituents may be identical or different, $R^2$ denotes the hydrogen atom or the methyl group and one of the groups $A^1$ and $A^2$ denotes the hydrogen atom and the other denotes the amino or methylamino group, the [1,4']bipiperidinyl-1'-yl group or the group

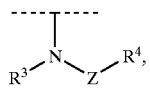

(II)

wherein R3 denotes the hydrogen atom or the methyl group,

Z denotes the carbonyl or sulphonyl group and $R^4$ denotes a branched or unbranched $C_{1-5}$-alkoxy group, a 1- or 4-piperidinyl group optionally substituted by a 1-methyl-4-piperidinyl, 4-methyl-1-piperazinyl or 1-piperidinyl group, a 1-methyl-4-piperidinyloxy group, a 2-pyridinylamino, benzo[b]furan-2-yl, 1,2,4-triazol-1-yl or 1H-indol-2-yl group, a phenyl group optionally substituted by a 4-methyl-1-piperazinyl or 4-phenylmethyl-1-piperazinyl group or a branched or unbranched alkyl group comprising 1 to 7 carbon atoms which is substituted in the ω position by an amino, phenyl, 2-pyridinyl, phenoxy, phenylamino, phenylmethoxycarbonylamino or N-methylphenylamino group, by a dimethylamino group, by a 1-piperidinyl or 1-piperazinyl group optionally substituted by a phenyl, pyridinyl, dimethylamino, 4-morpholinyl, 4-methyl-hexahydro-1H-1,4-diazepin-1-yl, 4-methyl-1-piperazinyl, 4-(methylsulphonyl)-1-piperazinyl, 4-(3-dimethylaminopropyl)-1-piperazinyl, (2-dimethylaminoethyl)-1-piperazinyl, 1-methyl-4.-piperidinyl or 1-piperidinyl group, by a 4-methyl-1-piperazinyl group, by a N-methyl-N-(1'-methyl-[1,4']bipiperidinyl-1-yl)amino or 4-(1-piperidinylmethyl)-1-piperidinyl group or is substituted in the α position by an amino, tert.butoxycarbonylamino or {{{[1,4']bipiperidinyl-1'-yl}-acetyl}amino} group or is substituted in the α position by an amino, phenyl or phenylmethoxycarbonylamino group and in the α position by an amino, tert.butoxycarbonylamino or {{{[1,4']bipiperidinyl-1'-yl}-acetyl}amino} group, whilst the abovementioned alkyl groups or the alkyl groups contained in the abovementioned groups, unless otherwise specified, contain 1 to 4 carbon atoms and may be branched or unbranched and the abovementioned aromatic and heteroaromatic groups may additionally be mono-, di- or trisubstituted by fluorine, chlorine or bromine atoms, by cyano or hydroxy groups, the tautomers, diastereomers, enantiomers and salts thereof.

Most particularly preferred compounds of the above general formula (I) are those wherein R denotes a 3,4-dihydro-2(1H)-oxoquinazolin-3-yl, 1,3-dihydro-4-phenyl-2H-2-oxoimidazol-1-yl, 2,4-dihydro-5-phenyl-3(3H)-oxo-1,2,4-triazol-2-yl, 1,3-dihydro-2(2H)-oxoimidazo[4,5-c]quinolin-3-yl, 1,3,4,5-tetrahydro-2-oxo-1,3-benzodiazepin-3-yl, 1,3-dihydro-5-methyl-2,4 (2H,5H)-dioxoimidazo[4,5-c]quinolin-3-yl, 5,7-dihydro-6-oxo-1,3-dibenzodiazepin-5-yl or 1,3-dihydro-2-oxobenzimidazol-1-yl group, whilst the abovementioned bicyclic heterocyclic groups may additionally be monosubstituted in the carbon skeleton by methoxy groups, $R^1$ denotes a phenyl group optionally mono-, di- or trisubstituted by fluorine, chlorine or bromine atoms or by hydroxy or amino groups, whilst the substituents may be identical or different, $R^2$ denotes the hydrogen atom or the methyl group one of the groups $A^1$ and $A^2$ denotes the hydrogen atom and the other denotes the amino or methylamino group, the [1,4']bipiperidinyl-1'-yl group or the group

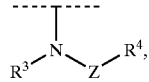

(II)

wherein $R^3$ denotes the hydrogen atom or the methyl group,

Z denotes the carbonyl or sulphonyl group and $R^4$ denotes a branched or unbranched $C_{1-4}$-alkoxy group, a 1- or 4-piperidinyl group optionally substituted by a 1-methyl-4-piperidinyl, 4-methyl-1-piperazinyl or 1-piperidinyl group, a 1-methyl-4-piperidinyloxy group, a 2-pyridinylamino, benzo[b]furan-2-yl, 1,2,4-triazol-1-yl or 1H-indol-2-yl group, a phenyl group optionally substituted by a 4-methyl-1-piperazinyl or 4-phenylmethyl-1-piperazinyl group, or a branched or unbranched alkyl group having 1 to 7 carbon atoms, preferably 1 to 5 carbon atoms, which is substituted in the ω position by an amino, 2-pyridinyl, phenoxy, phenylamino, phenylmethoxycarbonylamino or N-methylphenylamino group, by a dimethylamino group, by a 1-piperidinyl or 1-piperazinyl group optionally substituted by a phenyl, 4-pyridinyl, dimethylamino, 4-morpholinyl, 4-methyl-hexahydro-1H-1,4-diazepin-1-yl, 4-methyl-1-piperazinyl, 4-(methylsulphonyl)-1-piperazinyl, 4-(3-dimethylaminopropyl)-1-piperazinyl, 1-methyl-4-piperidinyl or 1-piperidinyl group, by a 4-methyl-1-piperazinyl group, by an N-methyl-N-(1'-methyl-[1,4']bipiperidinyl-1-yl)amino or 4-(1-piperidinylmethyl)-1-piperidinyl group or is substituted in the o position by an amino, phenyl or phenylmethoxycarbonylamino group and in the α position by an amino, tert.butoxycarbonylamino or {{{[1,4']bipiperidinyl-1'-yl}-acetyl}amino} group, whilst the abovementioned alkyl groups or the alkyl groups contained in the abovementioned groups, unless otherwise specified, contain 1 to 4 carbon atoms and may be branched or unbranched and the abovementioned aromatic and heteroaromatic groups may additionally be mono-, di- or trisubstituted by fluorine, chlorine or bromine atoms, by cyano or hydroxy groups, the tautomers, diastereomers, enantiomers and salts thereof.

The following compounds are mentioned as examples of particularly preferred compounds:

(1) (R,S)-4-(4-amino-3,5-dibromophenyl)-2-[(1,1-dimethylethoxycarbonyl)methylamino]-1-{4-[2(2H)-oxo-1,3,4,5-tetrahydro-1,3-benzodiazepin-3-yl]-1-piperidinyl}-1,4-butanedione (2) (R,S)-4-(4-amino-3,5-dibromophenyl)-2-{{{[1,4']-bipiperidinyl-1'-yl}acetyl}methylamino}-1-{(4-[2(2H)-oxo-1,3,4,5-tetrahydro-1,3-benzodiazepin-3-yl]-1-piperidinyl}-1,4-butanedione (3) (R,S)-2-[(acetyl)methylamino]-4-(4-amino-3,5-dibromophenyl)-1-{4-[2(2H)-oxo-1,3,4,5-tetrahydro-1,3-benzodiazepin-3-yl]-1-piperidinyl}-1,4-butanedione (4) (R,S)-4-(4-amino-3,5-dibromophenyl)-1-{4-[1,4-dihydro-2(2H)-oxoquinazolin-3-yl]-1-piperidinyl}-2-[(1,1-dimethylethoxycarbonyl)amino]-1,4-butanedione (5) (R,S)-4-(4-amino-3,5-dibromophenyl)-1-{4-[1,4-dihydro-2(2H)-oxoquinazolin-3-yl]-1-piperidinyl}-2-{[4-(dimethylamino)-1-oxobutyl]amino}-1,4-butanedione (6) (R,S)-2-amino-4-(4-amino-3,5-dibromophenyl)-1-{4-[1,4-dihydro-2(2H)-oxoquinazolin-3-yl]-1-piperidinyl}-1,4-butanedione (7) (R,S)-4-(4-amino-3,5-dibromophenyl)-1-{4-[1,4-dihydro-2(2H)-oxoquinazolin-3-yl]-1-piperidinyl}-2-{{{(1-methyl-[1,4']bipiperidinyl-4-yl}carbonyl]amino}-1,4-butanedione (8) (R,S)-4-(4-amino-3,5-dibromophenyl)-1-{4-[1,4-dihydro-2(2H)-oxoquinazolin-3-yl]-1-piperidinyl}-2-{[(4-methyl-1-piperazinyl)acetyl]amino}-1,4-butanedione (9) (R,S)-4-(4-amino-3,5-dibromophenyl)-1-{4-[5-methyl-2,4-dioxo-2,3,4,5-tetrahydro-1H-imidazo[4,5-c]quinolin-3-yl]-1-piperidinyl}-2-{[(4-methyl-1-piperazinyl)acetyl]amino}-1,4-butanedione

(10) (R,S)-4-(4-amino-3,5-dibromophenyl)-1-{4-[5,7-dihydro-6(6H)-oxodibenzo[d,f][1,3]diazepin-5-yl]-1-piperidinyl}-2-{[(4-methyl-1-piperazinyl)acetyl]amino}-1,4-butanedione

(11) (R,S)-4-(4-amino-3,5-dibromophenyl)-1-{4-[1,3-dihydro-2(2H)-oxo-4-phenyl-1-imidazolyl]-1-piperidinyl}-2-{[(4-methyl-1-piperazinyl)acetyl]amino}-1,4-butanedione

(12) (R,S)-4-(4-amino-3,5-dibromophenyl)-1-{4-[1,3-dihydro-2(2H)-oxo-imidazo[4,5-c]quinolin-3-yl]-1-piperidinyl}-2-{[(4-methyl-1-piperazinyl)acetyl]amino}-1,4-butanedione

(13) (R,S)-4-(4-amino-3,5-dibromophenyl)-1-{4-[1,4-dihydro-5(5H)-oxo-3-phenyl-[1,2,4]triazol-1-yl]-1-piperidinyl}-2-{[(4-methyl-1-piperazinyl)acetyl]amino}-1,4-butanedione

(14) (R,S)-4-(4-amino-3,5-dibromophenyl)-1-{4-[7-methoxy-2(2H)-oxo-1,3,4,5-tetrahydro-1,3-benzodiazepin-3-yl]-1-piperidinyl}-2-{[(4-methyl-1-piperazinyl)acetyl]amino}-1,4-butanedione

(15) (R,S)-4-(4-amino-3,5-dibromophenyl)-2-{[(4-methyl-1-piperazinyl)acetyl]amino}-1-{4-[2(2H)-oxo-1,3,4,5-tetrahydro-1,3-benzodiazepin-3-yl]-1-piperidinyl}-1,4-butanedione

(16) (R,S)-4-(4-amino-3,5-dibromophenyl)-1-{4-[2(2H)-oxo-1,3-dihydrobenzimidazol-1-yl]-1-piperidinyl}-2-{[(4-methyl-1-piperazinyl)acetyl]amino}-1,4-butanedione

(17) (R,S)-4-(4-amino-3,5-dibromophenyl)-2-[(1,1-dimethylethoxycarbonyl)amino]-1-{4-[2(2H)-oxo-1,3,4,5-tetrahydro-1,3-benzodiazepin-3-yl]-1-piperidinyl}-1,4-butanedione

(18) (R,S)-2-amino-4-(4-amino-3,5-dibromophenyl)-1-{4-[2(2H)-oxo-1,3,4,5-tetrahydro-1,3-benzodiazepin-3-yl]-1-piperidinyl}-1,4-butanedione

(19) (R,S)-4-(4-amino-3,5-dibromophenyl)-2-{{{[1,4']-bipiperidinyl-1'-yl}acetyl}amino}-1-{4-[2(2H)-oxo-1,3,4,5-tetrahydro-1,3-benzodiazepin-3-yl]-1-piperidinyl}-1,4-butanedione

(20) (R,S)-4-(4-amino-3,5-dibromophenyl)-2-{{[4-(4-methyl-1-piperazinyl)-1-piperidinyl]carbonyl}amino}-1-{4-[2(2H)-oxo-1,3,4,5-tetrahydro-1,3-benzodiazepin-3-yl]-1-piperidinyl}-1,4-butanedione

(21) (R,S)-4-(4-amino-3,5-dibromophenyl)-2-{{{[1,4']-bipiperidinyl-1'-yl}carbonyl}amino}-1-{4-[2(2H)-oxo-1,3,4,5-tetrahydro-1,3-benzodiazepin-3-yl]-1-piperidinyl}-1,4-butanedione

(22) (R,S)-4-(4-amino-3,5-dibromophenyl)-2-{{[4-(dimethylamino)-1-piperidinyl]acetyl}amino}-1-{4-[2(2H)-oxo-1,3,4,5-tetrahydro-1,3-benzodiazepin-3-yl]-1-piperidinyl}-1,4-butanedione

(23) (R,S)-4-(4-amino-3,5-dibromophenyl)-2-{{[4-(4-methyl-1-piperazinyl)-1-piperidinyl]acetyl}amino}-1-{4-[2(2H)-oxo-1,3,4,5-tetrahydro-1,3-benzodiazepin-3-yl]-1-piperidinyl}-1,4-butanedione

(24) (R,S)-4-(4-amino-3,5-dibromophenyl)-2-1{[(1-methyl-4-piperidinyl)oxy]carbonyl}amino}-1-{4-[2(2H)-oxo-1,3,4,5-tetrahydro-1,3-benzodiazepin-3-yl]-1-piperidinyl}-1,4-butanedione

(25) (R,S)-2-(acetylamino)-4-(4-amino-3,5-dibromophenyl)-1-{4-[2(2H)-oxo-1,3,4,5-tetrahydro-1,3-benzodiazepin-3-yl]-1-piperidinyl}-1,4-butanedione

(26) (R,S)-4-(4-amino-3,5-dichlorophenyl)-2-{{{[1,4']bipiperidinyl-1'-yl}acetyl}amino}-1-{4-[2(2H)-oxo-1,3,4,5-tetrahydro-1,3-benzodiazepin-3-yl]-1-piperidinyl}-1,4-butanedione

(27) (R,S)-4-(4-amino-3,5-dichlorophenyl)-2-{{[4-(4-methyl-1-piperazinyl)-1-piperidinyl]acetyl}amino}-1-{4-[2(2H)-oxo-1,3,4,5-tetrahydro-1,3-benzodiazepin-3-yl]-1-piperidinyl}-1,4-butanedione

(28) (R,S)-4-(4-amino-3,5-dibromophenyl)-2-{[1,4']-bipiperidinyl-1'-yl}-1-{4-[2(2H)-oxo-1,3,4,5-tetrahydro-1,3-benzodiazepin-3-yl]-1-piperidinyl}-1,4-butanedione

(29) (R,S)-4-(4-amino-3,5-dibromophenyl)-2-{{{2-{[1,4']-bipiperidinyl-1'-yl}ethyl}sulphonyl}amino}-1-{4-[2(2H)-oxo-1,3,4,5-tetrahydro-1,3-benzodiazepin-3-yl]-1-piperidinyl}-1,4-butanedione

(30) (R,S)-4-(4-amino-3,5-dibromophenyl)-2-{{{[1,4']-bipiperidinyl-1'-yl}-acetyl}amino}-2-methyl-1-{4-[2(2H)-oxo-1,3,4,5-tetrahydro-1,3-benzodiazepin-3-yl]-1-piperidinyl}-1,4-butanedione

(31) (R,S)-4-(4-amino-3,5-dibromophenyl)-1-{4-[2(2H)-oxo-1,3,4,5-tetrahydro-1,3-benzodiazepin-3-yl]-1-piperidinyl}-2-(phenoxyacetylamino)-1,4-butanedione

(32) (R,S)-4-(4-amino-3,5-dibromophenyl)-2-(4-chlorophenoxyacetylamino)-1-{4-[2(2H)-oxo-1,3,4,5-tetrahydro-1,3-benzodiazepin-3-yl]-1-piperidinyl}-1,4-butanedione

(33) (R,S)-4-(4-amino-3,5-dibromophenyl)-2-(4-hydroxyphenoxyacetylamino)-1-{4-[2(2H)-oxo-1,3,4,5-tetrahydro-1,3-benzodiazepin-3-yl]-1-piperidinyl}-1,4-butanedione

(34) (R,S)-4-(4-amino-3,5-dibromophenyl)-2-(4-bromophenoxyacetylamino)-1-{4-[2(2H)-oxo-1,3,4,5-tetrahydro-1,3-benzodiazepin-3-yl]-1-piperidinyl}-1,4-butanedione

(35) (R,S)-4-(4-amino-3,5-dibromophenyl)-2-(4-cyanophenoxyacetylamino)-1-{4-[2(2H)-oxo-1,3,4,5-tetrahydro-1,3-benzodiazepin-3-yl]-1-piperidinyl}-1,4-butanedione

(36) (R,S)-4-(4-amino-3,5-dibromophenyl)-2-(benzo[b]furan-2-carbonylamino)-1-{4-[2(2H)-oxo-1,3,4,5-tetrahydro-1,3-benzodiazepin-3-yl]-1-piperidinyl}-1,4-butanedione

(37) (R,S)-4-(4-amino-3,5-dibromophenyl)-2-(1,2,4-triazol-1-carbonylamino)-1-{4-[2(2H)-oxo-1,3,4,5-tetrahydro-1,3-benzodiazepin-3-yl]-1-piperidinyl}-1,4-butanedione

(38) (R,S)-4-(4-amino-3,5-dibromophenyl)-2-(1H-indol-2-carbonyl-amino)-1-{4-[2(2H)-oxo-1,3,4,5-tetrahydro-1,3-benzodiazepin-3-yl]-1-piperidinyl}-1,4-butanedione

(39) (R,S)-4-(4-amino-3,5-dibromophenyl)-2-(phenylaminoacetylamino)-1-{4-[2(2H)-oxo-1,3,4,5-tetrahydro-1,3-benzodiazepin-3-yl]-1-piperidinyl}-1,4-butanedione

(40) (R,S)-4-(4-amino-3,5-dibromophenyl)-2-[(N-methylphenylamino)acetylamino]-1-{4-[2(2H)-oxo-1,3,4,5-tetrahydro-1,3-benzo-diazepin-3-yl]-1-piperidinyl}-1,4-butanedione

(41) (R,S)-4-(4-amino-3,5-dibromophenyl)-2-[(N-methyl-4-chlorophenylamino)acetylamino]-1-{4-[2(2H)-oxo-1,3,4,5-tetrahydro-1,3-benzodiazepin-3-yl]-1-piperidinyl}-1,4-butanedione

(42) (R,S)-4-(4-amino-3,5-dibromophenyl)-2-{{[4-(1-methyl-4-piperidinyl)-1-piperazinyl]acetyl}amino}-1-{4-[2(2H)-oxo-1,3,4,5-tetrahydro-1,3-benzodiazepin-3-yl]-1-piperidinyl}-1,4-butanedione

(43) (R,S)-4-(4-amino-3,5-dibromophenyl)-2-(2-pyridinylacetylamino)-1-{4-[2(2H)-oxo-1,3,4,5-tetrahydro-1,3-benzodiazepin-3-yl]-1-piperidinyl}-1,4-butanedione

(44) (R,S)-4-(4-amino-3,5-dibromophenyl)-2-(2-pyridinylaminocarbonylamino)-1-{4-[2(2H)-oxo-1,3,4,5-tetrahydro-1,3-benzodiazepin-3-yl]-1-piperidinyl}-1,4-butanedione

(45) (R,S)-4-(4-amino-3,5-dibromophenyl)-2-{{[4-(4-morpholinyl)-1-piperidinyl]acetyl}amino}-1-{4-[2(2H)-oxo-1,3,4,5-tetrahydro-1,3-benzodiazepin-3-yl]-1-piperidinyl}-1,4-butanedione

(46) (R,S)-4-(4-amino-3,5-dibromophenyl)-2-{{[4-(4-pyridinyl)-1-piperazinyl]acetyl}amino}-1-{4-[2(2H)-oxo-1,3,4,5-tetrahydro-1,3-benzodiazepin-3-yl]-1-piperidinyl}-1,4-butanedione

(47) (R,S)-4-(4-amino-3,5-dibromophenyl)-2-{{{4-[4-(1-methylethyl)-1-piperazinyl]-1-piperidinyl}acetyl}-amino}-1-{4-[2(2H)-oxo-1,3,4,5-tetrahydro-1,3-benzodiazepin-3-yl]-1-piperidinyl}-1,4-butanedione

(48) (R,S)-4-(4-amino-3,5-dibromophenyl)-2-{{[4-(hexahydro-4-methyl-1H-1,4-diazepin-1-yl)-1-piperidinyl]acetyl}amino}-1-{4-[2(2H)-oxo-1,3,4,5-tetrahydro-1,3-benzodiazepin-3-yl]-1-piperidinyl}-1,4-butanedione

(49) (R,S)-4-(4-amino-3,5-dibromophenyl)-2-{{{4-[4-(methylsulphonyl)-1-piperazinyl]-1-piperidinyl}acetyl}-amino}-1-{4-[2(2H)-oxo-1,3,4,5-tetrahydro-1,3-benzodiazepin-3-yl]-1-piperidinyl}-1,4-butanedione

(50) (R,S)-4-(4-amino-3,5-dibromophenyl)-2-{{{4-[4-(3-dimethylaminopropyl)-1-piperazinyl]-1-piperidinyl}acetyl}amino}-1-{4-[2(2H)-oxo-1,3,4,5-tetrahydro-1,3-benzodiazepin-3-yl]-1-piperidinyl}-1,4-butanedione

(51) (R,S)-4-(4-amino-3,5-dibromophenyl)-2-[(1-oxo-3-phenylpropyl)amino]-1-{4-[2(2H)-oxo-1,3,4,5-tetrahydro-1,3-benzodiazepin-3-yl]-1-piperidinyl}-1,4-butanedione

(52) (R,S)-4-(4-amino-3,5-dibromophenyl)-2-{{3-{[1,4']-bipiperidinyl-1'-yl}-1-oxopropyl}amino}-1-{4-[2(2H)-oxo-1,3,4,5-tetrahydro-1,3-benzodiazepin-3-yl]-1-piperidinyl}-1,4-butanedione

(53) (R,S)-4-(4-amino-3,5-dibromophenyl)-2-{{{N-methyl-N-{1'-methyl-[1,4']bipiperidinyl-4-yl}amino}acetyl}-amino}-1-{4-[2(2H)-oxo-1,3,4,5-tetrahydro-1,3-benzodiazepin-3-yl]-1-piperidinyl}-1,4-butanedione

(54) (R,S)-4-(4-amino-3,5-dibromophenyl)-2-{{[4-(1-piperidinylmethyl)-1-piperidinyl]acetyl}amino}-1-{4-[2(2H)-oxo-1,3,4,5-tetrahydro-1,3-benzodiazepin-3-yl]-1-piperidinyl}-1,4-butanedione

(55) (R,S)-4-(4-amino-3,5-dibromophenyl)-2-{{3-[4-(4-methyl-1-piperazinyl)-1-piperidinyl]-1-oxopropyl}-amino}-1-{4-[2(2H)-oxo-1,3,4,5-tetrahydro-1,3-benzodiazepin-3-yl]-1-piperidinyl}-1,4-butanedione

(56) (R,S)-4-(4-amino-3,5-dibromophenyl)-2-[4-(4-methyl-1-piperazinyl)benzoylamino]-1-{4-[2(2H)-oxo-1,3,4,5-tetrahydro-1,3-benzodiazepin-3-yl]-1-piperidinyl}-1,4-butanedione

(57) (R,S)-4-(4-amino-3,5-dibromophenyl)-2-[4-(4-phenylmethyl-1-piperazinyl)benzoylamino]-1-{4-[2(2H)-oxo-1,3,4,5-tetrahydro-1,3-benzodiazepin-3-yl]-1-piperidinyl}-1,4-butanedione

(58) 4-(4-amino-3,5-dibromophenyl)-2-{[2-(1,1-dimethylethoxycarbonylamino)-1-oxo-6-(phenylmethoxycarbonylamino)hexyl]-amino}-1-{4-[2(2H)-oxo-1,3,4,5-tetrahydro-1,3-benzodiazepin-3-yl]-1-piperidinyl}-1,4-butanedione

(59) 4-(4-amino-3,5-dibromophenyl)-2-{[2-amino-1-oxo-6-(phenylmethoxycarbonylamino)hexyl]amino}-1-{4-[2(2H)-oxo-1,3,4,5-tetrahydro-1,3-benzodiazepin-3-yl]-1-piperidinyl}-1,4-butanedione

(60) (R,S)-4-(4-amino-3,5-dibromophenyl)-2-{{3-[4-(dimethylamino)-1-piperidinyl]-1-oxopropyl}amino}-1-{4-[2(2H)-oxo-1,3,4,5-tetrahydro-1,3-benzodiazepin-3-yl]-1-piperidinyl}-1,4-butanedione

(61) 4-(4-amino-3,5-dibromophenyl)-2-{[2-{{{[1,4']-bipiperidinyl-1'-yl}-acetyl}amino}-1-oxo-6-(phenylmethoxycarbonylamino)hexyl]amino}-1-{4-[2(2H)-oxo-1,3,4,5-tetrahydro-1,3-benzodiazepin-3-yl]-1-piperidinyl}-1,4-butanedione

(62) (R,S)-4-(4-amino-3,5-dibromophenyl)-2-{{{2-[4-(4-methyl-1-piperazinyl)-1-piperidinyl]ethyl}sulphonyl}-amino}-1-{4-[2(2H)-oxo-1,3,4,5-tetrahydro-1,3-benzodiazepin-3-yl]-1-piperidinyl}-1,4-butanedione

(63) (R,S)-4-(4-amino-3,5-dibromophenyl)-2-{{{2-[4-(4-methyl-1-piperidinyl)-1-piperazinyl]ethyl}sulphonyl}-amino}-1-{4-[2(2H)-oxo-1,3,4,5-tetrahydro-1,3-benzodiazepin-3-yl]-1-piperidinyl}-1,4-butanedione

(64) 2-{[6-amino-2-{{{[1,4']bipiperidinyl-1'-yl}-acetyl}amino}-1-oxo-hexyl]amino}-4-(4-amino-3,5-dibromophenyl)-1-{4-[2(2H)-oxo-1,3,4,5-tetrahydro-1,3-benzodiazepin-3-yl]-1-piperidinyl}-1,4-butanedione

(65) 4-(4-amino-3,5-dibromophenyl)-2-{[3-(3,5-dibromo-4-hydroxy-phenyl)-2-(1,1-dimethylethoxycarbonylamino)-1-oxopropyl]amino}-1-{4-[2(2H)-oxo-1,3,4,5-tetrahydro-1,3-benzodiazepin-3-yl]-1-piperidinyl}-1,4-butanedione

(66) 2-{[2-amino-3-(3,5-dibromo-4-hydroxyphenyl)-1-oxopropyl]amino}-4-(4-amino-3,5-dibromophenyl)-1-{4-[2(2H)-oxo-1,3,4,5-tetrahydro-1,3-benzodiazepin-3-yl]-1-piperidinyl}-1,4-butanedione

(67) (R,S)-3-{{{[1,4']bipiperidinyl-1'-yl}acetyl}amino}-)-4-(3,5-dibromo-4-hydroxyphenyl)-1-{4-[2(2H)-oxo-1,3,4,5-tetrahydro-1,3-benzodiazepin-3-yl]-1-piperidinyl}-1,4-butanedione

(68) (R,S)-4-(3,5-dibromo-4-hydroxyphenyl)-1-{4-[2(2H)-oxo-1,3,4,5-tetrahydro-1,3-benzodiazepin-3-yl]-1-piperidinyl}-3-{{[4-(4-pyridinyl)-1-piperazinyl]acetyl}amino}-1,4-butanedione

(69) (R,S)-4-(3,5-dibromo-4-hydroxyphenyl)-3-{[(4-methyl-1-piperazinyl)acetyl]amino}-1-{4-[2(2H)-oxo-1,3,4,5-tetrahydro-1,3-benzodiazepin-3-yl]-1-piperidinyl}-1,4-butanedione and the salts thereof.

One subgroup of compounds of general formula (I) deserving special mention comprises those wherein R denotes a saturated, mono- or di-unsaturated 5- to 7-membered aza, diaza, triaza, oxaza, thiaza, thiadiaza or S,S-dioxidothiadiaza heterocyclic group, whilst the abovementioned heterocyclic groups may be linked via a carbon or nitrogen atom and may contain one or two carbonyl groups adjacent to a nitrogen atom, may be substituted at one of the nitrogen atoms by an alkyl group, may be substituted at one or two carbon atoms by an alkyl group, by a phenyl, phenylmethyl, naphthyl, biphenylyl, pyridinyl, diazinyl, furyl, thienyl, pyrrolyl, 1,3-oxazolyl, 1,3-thiazolyl, isoxazolyl, pyrazolyl, 1-methylpyrazolyl, imidazolyl or 1-methylimidazolyl groups, whilst the substituents may be identical or different, and wherein a double bond of one of the above-mentioned unsaturated heterocyclic groups may be fused to a benzene, pyridine, diazine, 1,3-oxazole, thiophene, furan, thiazole, pyrrole, N-methyl-pyrrole or quinoline ring, to a 2(1H)-oxoquinoline ring optionally substituted at the nitrogen atom by an alkyl group or to an imidazole or N-methylimidazole ring, or two olefinic double bonds of one of the abovementioned unsaturated heterocyclic groups may each be fused to a benzene ring, whilst the phenyl, pyridinyl, diazinyl, furyl, thienyl, pyrrolyl, 1,3-oxazolyl, 1,3-thiazolyl, isoxazolyl, pyrazolyl, 1-methylpyrazolyl, imidazolyl or 1-methylimidazolyl groups contained in R as well as benzo-, thieno-, pyrido- and diazino-fused heterocyclic groups may additionally be mono-, di- or trisubstituted in the carbon skeleton by fluorine, chlorine or bromine atoms, by alkyl, alkoxy, nitro, alkylthio, alkylsulphinyl, alkylsulphonyl, alkylsulphonylamino, phenyl, trifluoromethyl, alkoxycarbonyl, carboxy, dialkylamino, hydroxy, amino, acetylamino, propionylamino, aminocarbonyl, alkylaminocarbonyl, dialkylaminocarbonyl, (4-morpholinyl)carbonyl, (1-pyrrolidinyl)carbonyl, (1-piperidinyl)carbonyl, (hexahydro-1-azepinyl)carbonyl, (4-methyl-1-piperazinyl)carbonyl, methylenedioxy, aminocarbonylamino, alkanoyl, cyano, trifluoromethoxy, trifluoromethylthio, trifluoromethylsulphinyl or trifluoromethylsulphonyl groups, whilst the substituents may be identical or different, $R^1$ denotes a phenyl, 1-naphthyl, 2-naphthyl, 1H-indol-3-yl, 1-methyl-1H-indol-3-yl, 1-formyl-1H-indol-3-yl, 4-imidazolyl, 1-methyl-4-imidazolyl, 2-thienyl, 3-thienyl, thiazolyl, 1H-indazol-3-yl, 1-methyl-1H-indazol-3-yl, benzo[b]fur-3-yl, benzo[b]thien-3-yl, pyridinyl, quinolinyl or isoquinolinyl group, whilst the abovementioned aromatic and heteroaromatic groups may additionally be mono-, di- or trisubstituted in the carbon skeleton by fluorine, chlorine or bromine atoms, by alkyl groups, cycloalkyl groups with 3 to 8 carbon atoms, phenylalkyl groups, alkenyl, alkoxy, phenyl, phenylalkoxy, trifluoromethyl, alkoxycarbonyl, carboxy, dialkylamino, nitro, hydroxy, amino, alkylamino, acetylamino, propionylamino, methylsulphonyloxy, aminocarbonyl, alkylaminocarbonyl, dialkylaminocarbonyl, alkanoyl, cyano, tetrazolyl, phenyl, pyridinyl, thiazolyl, furyl, trifluoromethoxy, trifluoromethylthio, trifluoromethylsulphinyl or trifluoromethylsulphonyl groups and the substituents may be identical or different, $R^2$ denotes the hydrogen atom, one of the groups $A^1$ and $A^2$ denotes the hydrogen atom and the other denotes the amino, the [1,4']bipiperidinyl-1'-yl or an alkylamino group or the group

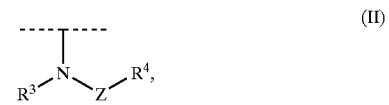

wherein $R^3$ denotes the hydrogen atom or an alkyl group,

Z denotes the carbonyl or the sulphonyl group and $R^4$ denotes an alkoxy, amino, alkylamino or dialkylamino group, a piperidinyl group optionally substituted by a 1-methyl-4-piperidinyl, 4-methyl-1-piperazinyl or piperidinyl group, a 1-methyl-4-piperidinyloxy group or a branched or unbranched alkyl group having 1 to 4 carbon atoms which may be substituted in the ω position by a dialkylamino group, by a piperidinyl group optionally substituted by a dimethylamino, 4-methyl-1-piperazinyl or piperidinyl group or by a 4-methyl-1-piperazinyl group, whilst the abovementioned alkyl and alkenyl groups or the alkyl groups contained in the abovementioned groups, unless otherwise specified, contain 1 to 5 carbon atoms and may be branched or unbranched.

The compounds of general formula I are prepared by methods known in principle. The following methods have proved particularly suitable for preparing the compounds of general formula I according to the invention:

a) In order to prepare compounds of general formula (I) wherein $A^1$ and $A^2$ have the meanings given hereinbefore with the exception of an optionally alkyl-substituted amino group:

coupling a carboxylic acid of general formula

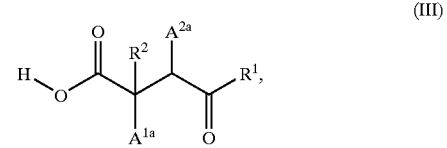

wherein $A^{1a}$ and $A^{2a}$ have the meanings given hereinbefore for $A^1$ and $A^2$ with the exception of an optionally alkyl-substituted amino group and $R^1$ and $R^2$ are as hereinbefore defined, with a compound of general formula

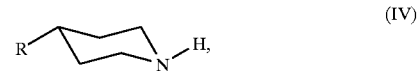

wherein R is as hereinbefore defined.

The coupling is preferably carried out using methods known from peptide chemistry (cf. e.g. Houben-Weyl, Methoden der Organischen Chemie, Vol. 15/2), for example using carbodiimides such as e.g. dicyclohexylcarbodiimide (DCC), diisopropyl carbodiimide (DIC) or ethyl-(3-dimethylaminopropyl)carbodiimide, O-(1H-benzotriazol-1-yl)-N,N-N',N'-tetramethyluronium hexafluorophosphate (HBTU) or tetrafluoroborate (TBTU) or 1H-benzotriazol-1-yl-oxy-tris-(dimethylamino)-phosphonium hexafluorophosphate (BOP). By adding 1-hydroxybenzotriazole (HOBt) or 3-hydroxy-4-oxo-3,4-dihydro-1,2,3-benzotriazine (HOObt) any possible racemisation can additionally be suppressed, if desired, or the reaction speed can be increased. The couplings are normally carried out with equimolar amounts of the coupling components as well as the coupling reagent in solvents such as dichloromethane, tetrahydrofuran, acetonitrile, dimethyl formamide (DMF), dimethyl acetamide (DMA), N-methylpyrrolidone (NMP) or mixtures thereof and at temperatures between −30 and +30° C., preferably −20 and +25° C. If necessary, N-ethyl-diisopropylamine (DIEA) (Hünig base) is preferably used as an additional auxiliary base.

The so-called anhydride process is used as a further coupling method for synthesising compounds of general formula I (cf. also: M. Bodanszky, "Peptide Chemistry", Springer-Verlag 1988, p. 58–59; M. Bodanszky, "Principles of Peptide Synthesis", Springer-Verlag 1984, p. 21–27). The Vaughan variant of the mixed anhydride process is preferred (J. R. Vaughan Jr., J. Amer. Chem. Soc. 73, 3547 (1951)), in which the mixed anhydride of the carboxylic acid of general formula (III) which is to be coupled and monoisobutyl carbonate, is obtained using isobutyl chlorocarbonate in the presence of bases such as 4-methyl-morpholine or 4-ethylmorpholine. The preparation of this mixed anhydride and the coupling with amines are carried out in a one-pot process, using the abovementioned solvents and at temperatures between −20 and +25° C., preferably 0 and +25° C.

b) In order to prepare compounds of general formula (I), wherein $A^1$ and $A^2$ have the meanings given hereinbefore with the exception of an optionally alkyl-substituted amino group:

coupling a compound of general formula

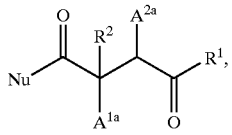

(V)

wherein
$A^{1a}$ and $A^{2a}$ have the meanings given for $A^1$ and $A^2$ hereinbefore with the exception of an optionally alkyl-substituted amino group, $R^1$ and $R^2$ are as hereinbefore defined and Nu denotes a leaving group, e.g. a halogen atom such as the chlorine, bromine or iodine atom, an alkylsulphonyloxy group with 1 to 10 carbon atoms in the alkyl moiety, a phenylsulphonyloxy or naphthylsulphonyloxy group optionally mono-, di- or trisubstituted by chlorine or bromine atoms, by methyl or nitro groups, whilst the substituents may be identical or different, a 1H-imidazol-1-yl, a 1H-pyrazol-1-yl optionally substituted by 1 or 2 methyl groups in the carbon skeleton, a 1H-1,2,4-triazol-1-yl, 1H-1,2,3-triazol-1-yl, 1H-1,2,3,4-tetrazol-1-yl, a vinyl, propargyl, p-nitrophenyl, 2,4-dinitrophenyl, trichlorophenyl, pentachlorophenyl, pentafluorophenyl, pyranyl or pyridinyl, a dimethylaminyloxy, 2(1H)-oxopyridin-1-yloxy, 2,5-dioxopyrrolidin-1-yloxy, phthalimidyloxy, 1H-benzotriazol-1-yloxy or azide group, with a compound of general formula

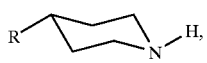

(IV)

wherein R is as hereinbefore defined.

The reaction is carried out under Schotten-Baumann or Einhorn conditions, i.e. the components are reacted in the presence of at least one equivalent of an auxiliary base at temperatures between −50° C. and +120° C., preferably −10° C. and +30° C., and optionally in the presence of solvents. The auxiliary bases used are preferably alkali metal and alkaline earth metal hydroxides, e.g. sodium hydroxide, potassium hydroxide or barium hydroxide, alkali metal carbonates, e.g. sodium carbonate, potassium carbonate or caesium carbonate, alkali metal acetates, e.g. sodium or potassium acetate, as well as tertiary amines, e.g. pyridine, 2,4,6-trimethylpyridine, quinoline, triethylamine, N-ethyl-diisopropylamine, N-ethyl-dicyclohexylamine, 1,4-diazabicyclo[2,2,2]octane or 1,8-diazabicyclo[5,4,0]undec-7-ene, the solvents used may be, for example, dichloromethane, tetrahydrofuran, 1,4-dioxane, acetonitrile, dimethyl formamide, dimethyl acetamide, N-methylpyrrolidone or mixtures thereof; if alkali metal or alkaline earth metal hydroxides, alkali metal carbonates or acetates are used as the auxiliary bases, water may also be added to the reaction mixture as cosolvent.

c) In order to prepare compounds of general formula (I) wherein one of the two groups $A^1$ and $A^2$ denotes the hydrogen atom and the other denotes the group

(II)

wherein R3 is as hereinbefore defined, $R^4$ denotes a benzo[b]furanyl or 1H-indolyl group, a phenyl group optionally substituted by a 4-alkyl-1-piperazinyl or 4-arylalkyl-1-piperazinyl group or a branched or unbranched alkyl group comprising 1 to 7 carbon atoms which may be substituted in the ω position by a pyridinyl, phenyl, phenoxy or phenylmethoxycarbonylamino group, by a dialkylamino group, by a piperidinyl or piperazinyl group optionally substituted by a phenyl, pyridinyl, dimethylamino, 4-morpholinyl, 4-alkylhexahydro-1H-1,4-diazepin-1-yl, 4-alkyl-1-piperazinyl, 4-(alkylsulphonyl)-1-piperazinyl, 4-(dialkylaminoalkyl)-1-piperazinyl, 1-alkyl-4-piperidinyl or piperidinyl group, by a 4-methyl-1-piperazinyl group, by an N-methyl-N-(1'-methyl-[1,4']bipiperidinyl-1-yl)amino or 4-(1-piperidinylmethyl)-1-piperidinyl group and independently thereof may be substituted in the α position by a tert.alkoxy-carbonylamino or {{{[1,4']bipiperidinyl-1'-yl}-acetyl}amino} group, and Z denotes the carbonyl group:

coupling a carboxylic acid of general formula

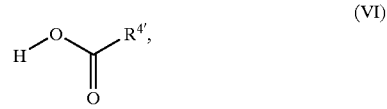

(VI)

wherein $R^{4'}$ denotes a benzo[b]furanyl or 1H-indolyl group, a phenyl group optionally substituted by a 4-alkyl-1-piperazinyl or 4-arylalkyl-1-piperazinyl group, or a branched or unbranched alkyl group comprising 1 to 7 carbon atoms which may be substituted in the o position by a pyridinyl, phenyl, phenoxy or phenylmethoxycarbonylamino group, by a dialkylamino group, by a piperidinyl or piperazinyl group optionally substituted by a phenyl, pyridinyl, dimethylamino, 4-morpholinyl, 4-alkylhexahydro-1H-1,4-diazepin-1-yl, 4-alkyl-1-piperazinyl, 4-(alkylsulphonyl)-1-piperazinyl, 4-(dialkylaminoalkyl)-1-piperazinyl, 1-alkyl-4-piperidinyl or piperidinyl group, by a 4-methyl-1-piperazinyl group, by an N-methyl-N-(1'-methyl-[1,4']bipiperidinyl-1-yl)amino or 4-(1-piperidinylmethyl)-1-piperidinyl group and independently thereof may be substituted in the α position by a tert.alkoxy-carbonylamino or {{{[1,4']bipiperidinyl-1'-yl}-acetyl}amino} group, with an amine of general formula

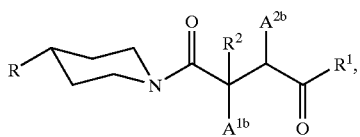
(VII)

wherein one of the groups $A^{1b}$ and $A^{2b}$ denotes the hydrogen atom and the other denotes the group

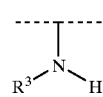
(VIII)

whilst R, $R^1$, $R^2$ and $R^3$ are as hereinbefore defined.

The coupling is preferably carried out using methods known from peptide chemistry (cf. e.g. Houben-Weyl, Methoden der Organischen Chemie, Vol. 15/2), for example using carbodiimides, such as e.g. dicyclohexylcarbodiimide (DCC), diisopropylcarbodiimide (DIC) or ethyl-(3-dimethylaminopropyl)-carbodiimide, O-(1H-benzotriazol-1-yl)-N,N-N',N'-tetramethyluronium hexafluorophosphate (HBTU) or tetrafluoroborate (TBTU) or 1H-benzotriazol-1-yl-oxy-tris-dimethylamino)-phosphonium hexafluorophosphate (BOP). By adding 1-hydroxybenzotriazole (HOBt) or 3-hydroxy-4-oxo-3,4-dihydro-1,2,3-benzotriazine (HOObt) any possible racemisation can additionally be suppressed, if desired, or the reaction speed can be increased. The couplings are normally carried out with equimolar amounts of the coupling components as well as the coupling reagent in solvents such as dichloromethane, tetrahydrofuran, acetonitrile, dimethyl formamide (DMF), dimethylacetamide (DMA), N-methylpyrrolidone (NMP) or mixtures thereof and at temperatures between −30 and +30° C., preferably −20 and +25° C. If necessary, N-ethyldiisopropylamine (DIEA) (Hünig base) is preferably used as an additional auxiliary base.

The so-called anhydride process is used as a further coupling method for synthesising compounds of general formula I (cf. also: M. Bodanszky, "Peptide Chemistry", Springer-Verlag 1988, p. 58–59; M. Bodanszky, "Principles of Peptide Synthesis", Springer-Verlag 1984, p. 21–27). The Vaughan variant of the mixed anhydride process is preferred (J. R. Vaughan Jr., J. Amer. Chem. Soc. 73, 3547 (1951)), in which the mixed anhydride of the carboxylic acid of general formula VI which is to be coupled and monoisobutyl carbonate, is obtained using isobutyl chlorocarbonate in the presence of bases such as 4-methylmorpholine or 4-ethylmorpholine. The preparation of this mixed anhydride and the coupling with amines are carried out in a one-pot process, using the abovementioned solvents and at temperatures between −20 and +25° C., preferably 0 and +25° C.

d) In order to prepare compounds of general formula (I) wherein one of the two groups $A^1$ and $A^2$ denotes the hydrogen atom and the other denotes the group

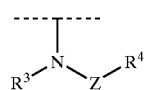
(II)

wherein $R^3$ is as hereinbefore defined, $R^4$ denotes a benzo[b]furanyl or 1H-indolyl group, a phenyl group optionally substituted by 4-alkyl-1-piperazinyl or 4-arylalkyl-1-piperazinyl-groups or a branched or unbranched alkyl group comprising 1 to 7 carbon atoms which may be substituted in the ω position by a pyridinyl, phenyl, phenoxy or phenylmethoxycarbonylamino group, by a dialkylamino group, by a piperidinyl or piperazinyl group optionally substituted by a phenyl, pyridinyl, dimethylamino, 4-morpholinyl, 4-alkylhexahydro-1H-1,4-diazepin-1-yl, 4-alkyl-1-piperazinyl, 4-(alkylsulphonyl)-1-piperazinyl, 4-(dialkylaminoalkyl)-1-piperazinyl, 1-alkyl-4-piperidinyl or piperidinyl group, by a 4-methyl-1-piperazinyl group, by an N-methyl-N-(1'-methyl-[1,4']bipiperidinyl-1-yl)amino or 4-(1-piperidinylmethyl)-1-piperidinyl group and may be substituted in the α position by a tert.alkoxy-carbonylamino or {{{[1,4']bipiperidinyl-11-yl}-acetyl}amino} group, and Z denotes the carbonyl group:

coupling a compound of general formula

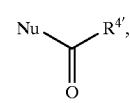
(IX)

wherein Nu denotes a leaving group, e.g. a halogen atom such as the chlorine, bromine or iodine atom, an alkylsulphonyloxy group with 1 to 10 carbon atoms in the alkyl moiety, a phenylsulphonyloxy or naphthylsulphonyloxy group optionally mono-, di- or trisubstituted by chlorine or bromine atoms or by methyl or nitro groups, whilst the substituents may be identical or different, a 1H-imidazol-1-yl, a 1H-pyrazol-1-yl optionally substituted by 1 or 2 methyl groups in the carbon skeleton, a 1H-1,2,4-triazol-1-yl, 1H-1,2,3-triazol-1-yl, 1H-1,2,3,4-tetrazol-1-yl, a vinyl, propargyl, p-nitrophenyl, 2,4-dinitrophenyl, trichlorophenyl, pentachlorophenyl, pentafluorophenyl, pyranyl or pyridinyl, a dimethylaminyloxy, 2(1H)-oxopyridin-1-yloxy, 2,5-dioxopyrrolidin-1-yloxy, phthalimidyloxy, 1H-benzotriazol-1-yloxy or azide group, and $R^{4'}$ denotes a benzo[b]furanyl or 1H-indolyl group, a phenyl group optionally substituted by 4-alkyl-1-piperazinyl or 4-arylalkyl-1-piperazinyl-groups, or a branched or unbranched alkyl group comprising 1 to 7 carbon atoms which may be substituted in the ω position by a pyridinyl, phenyl, phenoxy or phenylmethoxycarbonylamino group, by a dialkylamino group, by a piperidinyl or piperazinyl group optionally substituted by a phenyl, pyridinyl, dimethylamino, 4-morpholinyl, 4-alkylhexahydro-1H-1,4-diazepin-1-yl, 4-alkyl-1-piperazinyl, 4-(alkylsulphonyl)-1-piperazinyl, 4-(dialkylaminoalkyl)-1-piperazinyl, 1-alkyl-4-piperidinyl or piperidinyl group, by a 4-methyl-1-piperazinyl group, by an N-methyl-N-(1'-methyl-[1,4']bipiperidinyl-1-yl)amino or 4-(1-piperidinylmethyl)-1-piperidinyl group and may be substituted in the α position by a tert.alkoxy-carbonylamino or {{{[1,4']bipiperidinyl-1'-yl}-acetyl}amino} group, with an amine of general formula

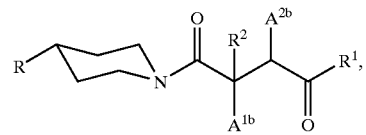
(VII)

wherein R, $R^1$ and $R^2$ are as hereinbefore defined, one of the groups $A^{1b}$ and $A^{2b}$ denotes the hydrogen atom and the other denotes the group

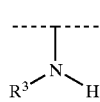
(VIII)

wherein $R^3$ denotes the hydrogen atom or an alkyl group.

The reaction is carried out under Schotten-Baumann or Einhorn conditions, i.e. the components are reacted in the presence of at least one equivalent of an auxiliary base at temperatures between −50° C. and +120° C., preferably −10° C. and +30° C., and optionally in the presence of solvents. The auxiliary bases used are preferably alkali metal and alkaline earth metal hydroxides, e.g. sodium hydroxide, potassium hydroxide or barium hydroxide, alkali metal carbonates, e.g. sodium carbonate, potassium carbonate or caesium carbonate, alkali metal acetates, e.g. sodium or potassium acetate, as well as tertiary amines, e.g. pyridine, 2,4,6-trimethylpyridine, quinoline, triethylamine, N-ethyl-diisopropylamine, N-ethyl-dicyclohexylamine, 1,4-diazabicyclo[2,2,2]octane or 1,8-diazabicyclo[5,4,0]undec-7-ene, the solvents used may be, for example, dichloromethane, tetrahydrofuran, 1,4-dioxane, acetonitrile, dimethyl formamide, dimethyl acetamide, N-methyl-pyrrolidone or mixtures thereof; if alkali metal or alkaline earth metal hydroxides, alkali metal carbonates or acetates are used as the auxiliary bases, water may also be added to the reaction mixture as cosolvent.

e) In order to prepare compounds of general formula (I) wherein one of the groups $A^1$ and $A^2$ denotes the hydrogen atom and the other denotes an optionally alkyl-substituted amino group:
acidolysis of compounds of general formula

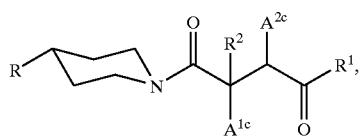
(X)

wherein one of the two groups $A^{1c}$ and $A^{2c}$ denotes the hydrogen atom and the other denotes the group

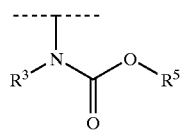
(XI)

where $R^5$ denotes a tert.alkyl group and R, $R^1$, $R^2$ and $R^3$ are as hereinbefore defined.

Acidolysis with trifluoroacetic acid is preferred, working with or without inert solvents, e.g. dichloromethane, and preferably in the absence of water. Suitable temperatures are between −50 and +90° C., preferably between 0° C. and room temperature. It has also proved satisfactory to carry out the acidolysis of compounds of general formula (X) with methanolic hydrochloric acid solution under reflux conditions, although experience has shown that an attack on carboxamide and ester functions cannot be entirely ruled out, which is why the trifluoroacetic acid variant is generally the method of choice.

f) In order to prepare compounds of general formula (I) wherein one of the two groups $A^1$ and $A^2$ denotes the hydrogen atom and the other denotes the group

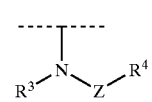
(II)

wherein $R^3$ is as hereinbefore defined, Z denotes the carbonyl group and $R^4$ denotes an alkoxy, amino, alkylamino or dialkylamino group, a 1-piperidinyl group optionally substituted by a 1-methyl-4-piperidinyl, 4-methyl-1-piperazinyl or piperidinyl group, a 1-methyl-4-piperidinyloxy group, a pyridinylamino or 1,2,4-triazol-1-yl group:
reacting an amine of general formula

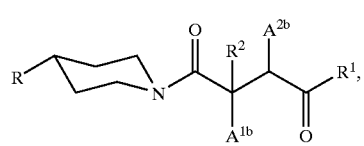
(VII)

wherein one of the groups $A^{1b}$ and $A^{2b}$ denotes the hydrogen atom and the other denotes the group

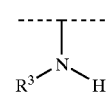
(VIII)

where R, $R^1$, $R^2$ and $R^3$ are as hereinbefore defined, with a compound of general formula

 H—$R^{4f}$ (XII), wherein
$R^{4f}$ denotes an alkoxy, amino, alkylamino or dialkylamino group, a 1-piperidinyl group optionally substituted by a 1-methyl-4-piperidinyl, 4-methyl-1-piperazinyl or piperidinyl group, a 1-methyl-4-piperidinyloxy group, a pyridinylamino or 1,2,4-triazol-1-yl group,
and with a carbonic acid derivative of general formula

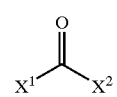
(XIII)

wherein
$X^1$ and $X^2$, which may be identical or different, denote a nucleofugic group, preferably the 1H-imidazol-1-yl, 1H-1,2,4-triazol-1-yl, trichloromethoxy, the 2,5-dioxopyrrolidin-1-yloxy group or the chlorine atom.

The reactions which are theoretically two-step reactions are usually carried out as one-pot processes, preferably by reacting one of the two components XII or VII with equimolar quantities of the carbonic acid derivative of general formula XIII in a suitable solvent at lower temperature in the first stage, then adding at least equimolar amounts of the other component VII or XII and finishing the reaction at elevated temperature. If the component of general formula XII corresponds to an alcohol, the reaction may also be accelerated using catalytic amounts of the associated alkoxide or imidazole-sodium.- but if the compound of general formula VII is a primary amine, catalysts are not generally needed. The reactions with bis-(trichloromethyl)-carbonate are preferably carried out in the presence of at least 2 equivalents (based on bis-(trichloromethyl)-carbonate) of a tertiary base, e.g. triethylamine, N-ethyl-diisopropylamine, pyridine, 1,5-diazabicyclo[4,3,0]non-5-ene, 1,4-diazabicyclo[2,2,2]octane or 1,8-diazabicyclo[5,4,0]undec-7-ene. Examples of solvents, which should be anhydrous, include tetrahydrofuran, dioxane, dimethyl formamide, dimethylacetamide, N-methyl-2-pyrrolidone, 1,3-dimethyl-2-imidazolidinone or acetonitrile; if bis(trichloromethyl)-carbonate is used as the carbonyl component anhydrous chlorohydrocarbons such as dichloromethane, 1,2-dichloroethane or trichloroethylene are preferred. The reaction temperatures for the first reaction step are between −30 and +25° C., preferably −5 and +10° C., for the second reaction step they are between +15° C. and the boiling temperature of the solvent used, preferably between +20° C. and +70° C. (cf. also: H. A. Staab and W. Rohr, "Synthesen mit heterocyclischen Amiden (Azoliden)", Neuere Methoden der Praparativen Organischen Chemie, Vol. V, p. 53–93, Verlag Chemie, Weinheim/Bergstr., 1967; P. Majer and R. S. Randad, J. Org. Chem. 59, 1937–1938 (1994); K. Takeda, Y. Akagi, A. Saiki, T. Sukahara and H. Ogura, Tetrahedron Letters 24 (42), 4569–4572 (1983)); M. Turconi, M. Nicola, L. Maiocchi, R. Micheletti, E. Giraldo and A. Donetti, J. Med. Chem. 33, 2101–2108, 2106 ff (1990)).

g) In order to prepare compounds of general formula (I) wherein one of the two groups $A^1$ and $A^2$ denotes the hydrogen atom and the other denotes the group

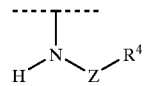
(XIV)

wherein Z denotes the carbonyl group and $R^4$ denotes an amino, alkylamino or dialkylamino group or a 1-piperidinyl group optionally substituted by a 1-methyl-4-piperidinyl, 4-methyl-1-piperazinyl or piperidinyl group: reacting an amine of general formula

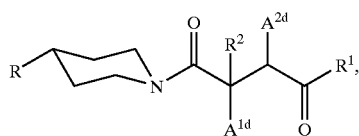
(VII')

wherein one of the groups $A^{1d}$ and $A^{2d}$ denotes the hydrogen atom, the other denotes the amino group and R and $R^1$ are as hereinbefore defined,
with a compound of general formula

H—R$^{4'}$ (XII'), wherein
R$^{4'}$ denotes an amino, alkylamino or dialkylamino group or a piperidinyl group optionally substituted by a 1-methyl-4-piperidinyl, 4-methyl-1-piperazinyl or piperidinyl group,
and with carbonic acid derivatives of general formula

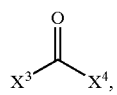
(XV)

wherein
$X^3$ denotes the phenoxy group if $X^4$ is the (1H)-1,2,3,4-tetrazol-1-yl group, the 4-nitrophenoxy group if $X^4$ is the 4-nitrophenoxy group, and the chlorine atom if $X^4$ denotes the 2,4,5-trichlorophenoxy group.

The reactions are theoretically two-step reactions with the intermediate formation of urethanes which can be isolated. However, the reactions may also be carried out as one-pot reactions. Preferably, in the first step, one of the two components XII' or VII' is reacted with equimolar amounts of the carbonic acid derivative of general formula XV in a suitable solvent at a lower temperature, then at least equimolar amounts of the other component VII' or XII' are added and the reaction is completed at a higher temperature. The reactions are preferably carried out in anhydrous solvents, for example in tetrahydrofuran, dioxane, dimethyl formamide, dimethylacetamide, N-methyl-2-pyrrolidone, 1,3-dimethyl-2-imidazolidinone, acetonitrile or anhydrous chlorohydrocarbons, for example dichloromethane, 1,2-dichloroethane or trichloroethylene. The reaction temperatures for the first reaction step are between −15 and +40° C., preferably −10 and +25° C., for the second reaction step they are between +20° C. and the boiling temperature of the solvent used, preferably between +20° C. and 100° C. (cf. also: R. W. Adamiak and J. Stawinski, Tetrahedron Letters 1977, 22, 1935–1936; A. W. Lipkowski, S. W. Tam and P. S. Portoghese, J. med. Chem. 29, 1222–1225 (1986); J. Izdebski and D. Pawlak, Synthesis 1989, 423–425).

h) In order to prepare compounds of general formula (I) wherein one of the two groups $A^1$ and $A^2$ denotes the hydrogen atom and the other denotes the group

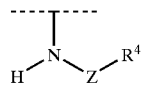
(XIV)

wherein Z denotes the sulphonyl group and $R^4$ denotes an amino, alkylamino or dialkylamino group or a piperidinyl group optionally substituted by a 1-methyl-4-piperidinyl, 4-methyl-1-piperazinyl or piperidinyl group:
reacting a compound of general formula

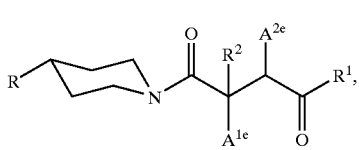
(VII")

wherein one of the groups $A^{1e}$ and $A^{2e}$ denotes the hydrogen atom and the other denotes the group

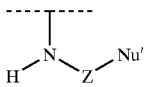
(XVI)

wherein R and $R^1$ are as hereinbefore defined, Z denotes the sulphonyl group and Nu' denotes a leaving group, for example a halogen atom such as the chlorine, bromine or iodine atom, an alkyl or arylsulphonyloxy group or an alkoxy group having up to 10 carbon atoms, e.g. the methoxy or ethoxy group, or a phenoxy or naphthoxy group optionally mono-, di- or trisubstituted by chlorine or bromine atoms, by methyl, nitro or hydroxy groups, whilst the substituents may be identical or different,
with an amine of general formula

H—R$^{4'}$ (XII'), wherein $R^{4'}$ denotes an amino, alkylamino or dialkylamino group or a piperidinyl group optionally substituted by a 1-methyl-4-piperidinyl, 4-methyl-1-piperazinyl or piperidinyl group.

If in general formula XVI Nu' denotes a halogen atom, an alkyl or arylsulphonyloxy group, the reaction is carried out under Schotten-Baumann or Einhorn conditions, i.e. the components are reacted in the presence of at least one equivalent of an auxiliary base at temperatures between −50° C. and +120° C., preferably −10° C. and +100° C., and optionally in the presence of solvents.

The auxiliary bases used are preferably alkali metal and alkaline earth metal hydroxides, e.g. sodium hydroxide, potassium hydroxide, alkali metal carbonates, e.g. sodium carbonate, potassium carbonate or caesium carbonate, alkali metal acetates, e.g. sodium or potassium acetate, as well as tertiary amines, e.g. pyridine, 2,4,6-trimethylpyridine, quinoline, triethylamine, N-ethyl-diisopropylamine, N-ethyl-dicyclohexylamine, 1,4-diazabicyclo[2,2,2]octane or 1,8-diazabicyclo[5,4,0]undec-7-ene, the solvents used may be, for example, dichloromethane, tetrahydrofuran, 1,4-dioxane, acetonitrile, dimethyl formamide, dimethyl acetamide, N-methyl-pyrrolidone or mixtures thereof; if alkali metal or alkaline earth metal hydroxides, alkali metal carbonates or acetates are used as the auxiliary bases, water may also be added to the reaction mixture as cosolvent.

The 2-hydroxyphenoxy group is preferred as the nucleofugic group Nu' in compounds of general formula XVI, while boiling dioxane is preferred as the solvent for the reaction with amines of general formula XII'.

The non-isolatable azasulphenes having the partial structure XVII are produced as intermediate products of the reaction:

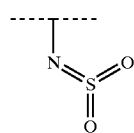

(XVII)

i) In order to prepare compounds of general formula (I) wherein one of the two groups $A^1$ and $A^2$ denotes the hydrogen atom and the other denotes the group

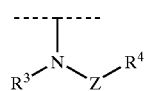

(II)

wherein $R^4$ denotes a branched or unbranched alkyl group comprising 1 to 7 carbon atoms which may be substituted in the ω position by a dialkylamino group, by a piperidinyl or piperazinyl group optionally substituted by a phenyl, pyridinyl, dimethylamino, 4-morpholinyl, 4-alkyl-hexahydro-1H-1,4-diazepin-1-yl, 4-alkyl-1-piperazinyl, 4-(alkylsulphonyl)-1-piperazinyl, 4-(dialkylaminoalkyl)-1-piperazinyl, 1-alkyl-4-piperidinyl or 1-piperidinyl group, by a 4-methyl-1-piperazinyl group, by an N-methyl-N-(1'-methyl-[1,4']bipiperidinyl-1-yl)amino or 4-(1-piperidinylmethyl)-1-piperidinyl group and in the α position by a tert.alkoxy-carbonylamino or {{{[1,4']bipiperidinyl-1'-yl}-acetyl}amino} group:

reacting a dialkylamine, a piperidine or piperazine optionally substituted by a phenyl, pyridinyl, dimethylamino, 4-morpholinyl, 4-alkyl-hexahydro-1H-1,4-diazepin-1-yl, 4-alkyl-1-piperazinyl, 4-(alkylsulphonyl)-1-piperazinyl, 4-(dialkylaminoalkyl)-1-piperazinyl, 1-alkyl-4-piperidinyl or 1-piperidinyl group but unsubstituted in the 1 position, 4-methylpiperazine, N-methyl-N-(1'-methyl-[1,4'] bipiperidinyl-1-yl)amine or 4-(1-piperidinylmethyl)-piperidine, with a compound of general formula

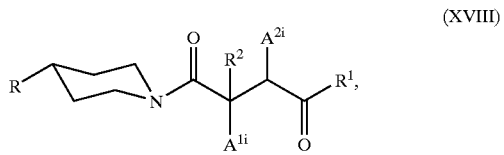

(XVIII)

wherein one of the two groups $A^{1i}$ and $A^{2i}$ denotes the hydrogen atom and the other denotes the group

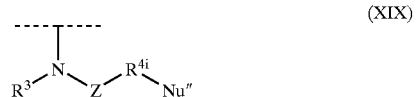

(XIX)

wherein R, $R^1$, $R^2$ and $R^3$ and Z are as hereinbefore defined, $R^{4i}$ denotes a branched or unbranched alkylene group having 1 to 7 carbon atoms which may be substituted in the α position by a tert.alkoxycarbonylamino or {{{[1,4'] bipiperidinyl-1'-yl}-acetyl}amino} group and Nu" denotes a leaving group in the ω position, for example a halogen atom such as the chlorine, bromine or iodine atom, an alkylsulphonyloxy group with 1 to 10 carbon atoms in the alkyl moiety, a phenylsulphonyloxy or naphthylsulphonyloxy group optionally mono-, di- or trisubstituted by chlorine or bromine atoms, by methyl or nitro groups, whilst the substituents may be identical or different.

The reaction is carried out with or without auxiliary bases at temperatures between 0° C. and +140° C., preferably between +20° C. and +100° C., and preferably in the presence of solvents. Suitable auxiliary bases include alkali and alkaline earth metal hydroxides, for example sodium hydroxide, potassium hydroxide or barium hydroxide, but preferably alkali metal carbonates, e.g. sodium carbonate, potassium carbonate or caesium carbonate, and also alkali metal acetates, e.g. sodium or potassium acetate, as well as tertiary amines, for example pyridine, 2,4,6-trimethylpyridine, quinoline, triethylamine, N-ethyl-diisopropylamine, N-ethyl-dicyclohexylamine, 1,4-diazabicyclo[2,2,2]octane or 1,8-diazabicyclo[5,4,0]undec-7-ene, whilst suitable solvents include for example dichloromethane, tetrahydrofuran, 1,4-dioxane, but preferably dipolar, aprotic solvents, for example acetonitrile, dimethyl formamide, dimethylacetamide, N-methylpyrrolidone, methyl-isobutylketone or mixtures thereof; if alkali or alkaline earth metal hydroxides, alkali metal carbonates or acetates are used as auxiliary bases, water may also be added to the reaction mixture as cosolvent. Moreover, to increase the reactivity of the group X in the starting materials of general formula V organic or preferably inorganic iodides, for example sodium or potassium iodide, may be added to the reaction mixture.

j) In order to prepare compounds of general formula (I), wherein $A^2$ denotes the hydrogen atom and $A^1$ denotes an optionally alkyl-substituted amino group or the [1,4'] bipiperidinyl-1'-yl group:
reacting compounds of general formula

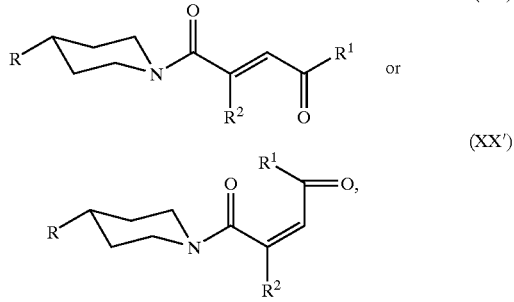

wherein R, $R^1$ and $R^2$ are as hereinbefore defined, with ammonia, an alkylamine or with [1,4']bipiperidinyl.

The reaction is generally successfully carried out under moderate conditions and without the addition of catalysts. The reaction may in general be carried out at temperatures between −10° C. and 150° C., preferably +15 to +35° C., at pressures between normal pressure and 300 bar and without or in the presence of additional solvents. Preferred solvents which may be used are alcohols such as methanol or ethanol, and ethers such as diethylether, tetrahydrofuran or 1,4-dioxane. If catalysis is needed, basic and acidic catalysts may be used. Of the basic catalysts which are preferred, alkali or alkaline earth metal hydroxides such as sodium, potassium or barium hydroxide, alkali metal alkoxides such as sodium ethoxide or potassium methoxide, as well as benzyltrimethylammonium hydroxide (Triton B) deserve a mention, while of the acidic catalysts glacial acetic acid deserves special mention.

k) In order to prepare compounds of general formula (I) wherein one of the two groups $A^1$ and $A^2$ denotes the hydrogen atom and the other denotes the group

wherein $R^3$ is as hereinbefore defined, $R^4$ denotes a branched or unbranched alkyl group comprising 1 to 7 carbon atoms which carries a {{{[1,4']bipiperidinyl-1'-yl}-acetyl}amino} group in the α position and may be substituted in the ω position by a phenyl, pyridinyl, phenoxy, phenylmethoxycarbonylamino or N-alkylphenylamino group, by a dialkylamino group, by a 1-piperidinyl or 1-piperazinyl group optionally substituted by a phenyl, pyridinyl, dimethylamino, 4-morpholinyl, 4-alkylhexahydro-1H-1,4-diazepin-1-yl, 4-alkyl-1-piperazinyl, 4-(alkylsulphonyl)-1-piperazinyl, 4-(dialkylaminoalkyl)-1-piperazinyl, 1-alkyl-4-piperidinyl or 1-piperidinyl group, by a 4-methyl-1-piperazinyl group, by an N-methyl-N-(1'-methyl-[1,4']bipiperidinyl-1-yl) amino or 4-(1-piperidinylmethyl)-1-piperidinyl group, and Z denotes the carbonyl group:

coupling [1,4']bipiperidinyl-1'-acetic acid with an amine of general formula

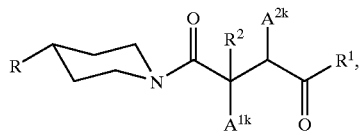

wherein one of the groups $A^{1k}$ and $A^{2k}$ denotes the hydrogen atom and the other denotes the group

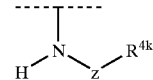

where R, $R^1$ and $R^2$ are as hereinbefore defined and $R^{4k}$ denotes a branched or unbranched alkyl group comprising 1 to 7 carbon atoms which carries an amino group in the α position and may be substituted in the ω position by a phenyl, pyridinyl, phenoxy, phenylmethoxycarbonylamino or N-alkylphenylamino group, by a dialkylamino group, by a 1-piperidinyl or 1-piperazinyl group optionally substituted by a phenyl, pyridinyl, dimethylamino, 4-morpholinyl, 4-alkyl-hexahydro-1H-1,4-diazepin-1-yl, 4-alkyl-1-piperazinyl, 4-(alkylsulphonyl)-1-piperazinyl, 4-(dialkylaminoalkyl)-1-piperazinyl, 1-alkyl-4-piperidinyl or 1-piperidinyl group, by a 4-methyl-1-piperazinyl group, a N-methyl-N-(1'-methyl-[1,4']bipiperidinyl-1-yl)amino or 4-(1-piperidinylmethyl)-1-piperidinyl group and Z denotes the carbonyl group.

The coupling is preferably carried out using methods known from peptide chemistry (cf. e.g. Houben-Weyl, Methoden der Organischen Chemie, Vol. 15/2), for example using carbodiimides, such as e.g. dicyclohexylcarbodiimide (DCC), diisopropylcarbodiimide (DIC) or ethyl-(3-dimethylaminopropyl)-carbodiimide, O-(1H-benzotriazol-1-yl)-N,N-N',N'-tetramethyluronium hexafluorophosphate (HBTU) or tetrafluoroborate (TBTU) or 1H-benzotriazol-1-yl-oxy-tris-dimethylamino)-phosphonium hexafluorophosphate (BOP). By adding 1-hydroxybenzotriazole (HOBt) or 3-hydroxy-4-oxo-3,4-dihydro-1,2,3-benzotriazine (HOObt) any possible racemisation can additionally be suppressed, if desired, or the reaction speed can be increased. The couplings are normally carried out with equimolar amounts of the coupling components as well as the coupling reagent in solvents such as dichloromethane, tetrahydrofuran, acetonitrile, dimethyl formamide (DMF), dimethylacetamide (DMA), N-methylpyrrolidone (NMP) or mixtures thereof and at temperatures between −30 and +30° C., preferably −20 and +25° C. If necessary, N-ethyl-diisopropylamine (DIEA) (Hünig base) is preferably used as an additional auxiliary base.

The so-called anhydride process is used as a further coupling method for synthesising compounds of general formula I (cf. also: M. Bodanszky, "Peptide Chemistry", Springer-Verlag 1988, p. 58–59; M. Bodanszky, "Principles of Peptide Synthesis", Springer-Verlag 1984, p. 21–27). The Vaughan variant of the mixed anhydride process is preferred (J. R. Vaughan Jr., J. Amer. Chem. Soc. 73, 3547 (1951)), in which the mixed anhydride of the carboxylic acid of general formula VI which is to be coupled and monoisobutyl carbonate, is obtained using isobutyl chlorocarbonate in the presence of bases such as 4-methylmorpholine or 4-ethylmorpholine. The preparation of this mixed anhydride and the coupling with amines are carried out in a one-pot process, using the abovementioned solvents and at temperatures between −20 and +25° C., preferably 0 and +25° C.

l) In order to prepare compounds of general formula (I) wherein one of the two groups $A^1$ and $A^2$ denotes the hydrogen atom and the other denotes the group

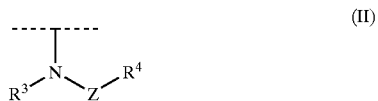

(II)

wherein $R^3$ and Z are as hereinbefore defined and $R^4$ denotes a 1,2-ethylene group which may be substituted in the ω position by an amino, [1,4']bipiperidinyl-1-yl, phenylamino or N-alkylphenylamino group, by a dialkylamino group, by a 1-piperidinyl or 1-piperazinyl group optionally substituted by a phenyl, pyridinyl, dimethylamino, 4-morpholinyl, 4-alkyl-hexahydro-1H-1,4-diazepin-1-yl, 4-alkyl-1-piperazinyl, 4-(alkylsulphonyl)-1-piperazinyl, 4-(dialkylaminoalkyl)-1-piperazinyl, 1-alkyl-4-piperidinyl or piperidinyl group, by a 4-methyl-1-piperazinyl group, a N-methyl-N-(1'-methyl-[1,4']bipiperidinyl-1-yl)amino or 4-(1-piperidinylmethyl)-1-piperidinyl group:
reacting compounds of general formula

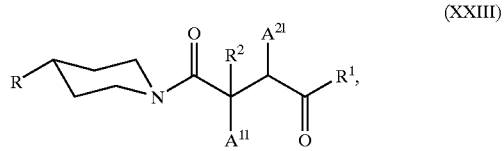

(XXIII)

wherein R, $R^1$ and $R^2$ are as hereinbefore defined and one of the groups $A^{11}$ and $A^{21}$ denotes the hydrogen atom and the other denotes the group

(XXIV)

wherein $R^3$ and Z have the meanings given hereinbefore, with ammonia, a phenylamine or N-alkyl-phenylamine, with [1,4']bipiperidinyl, with a dialkylamine, a piperidine or piperazine optionally substituted by a phenyl, pyridinyl, dimethylamino, 4-morpholinyl, 4-alkyl-hexahydro-1H-1,4-diazepin-1-yl, 4-alkyl-1-piperazinyl, 4-(alkylsulphonyl)-1-piperazinyl, 4-(dialkylaminoalkyl)-1-piperazinyl, 1-alkyl-4-piperidinyl or piperidinyl group, with 1-methylpiperazine, N-methyl-N-(1'-methyl-[1,4']bipiperidinyl-1-yl)amine or 4-(1-piperidinylmethyl)piperidine.

The reaction is generally successfully carried out under moderate conditions and without the addition of catalysts. The reaction may in general be carried out at temperatures between −10° C. and 150° C., preferably +15 to +35° C., at pressures between normal pressure and 300 bar and without or in the presence of additional solvents. Preferred solvents which may be used are alcohols such as methanol or ethanol, and ethers such as diethylether, tetrahydrofuran or 1,4-dioxane. If catalysis is needed, basic and acidic catalysts may be used. Of the basic catalysts which are preferred, alkali or alkaline earth metal hydroxides such as sodium, potassium or barium hydroxide, alkali metal alkoxides such as sodium ethoxide or potassium methoxide, as well as benzyltrimethylammonium hydroxide (Triton B) deserve a mention, while of the acidic catalysts glacial acetic acid deserves special mention.

m) In order to prepare compounds of general formula (I), wherein one of the two groups $A^1$ and $A^2$ denotes the hydrogen atom and the other denotes the group

(II)

wherein $R^3$ and Z are as hereinbefore defined and $R^4$ denotes a branched or unbranched alkyl group comprising 1 to 7 carbon atoms which is amino-substituted in the α position and may be substituted in the ω position by an amino, phenyl, pyridinyl, phenoxy, phenylamino, phenylmethoxycarbonylamino or N-alkylphenylamino group, by a dialkylamino group, by a piperidinyl or piperazinyl group optionally substituted by a phenyl, pyridinyl, dimethylamino, 4-morpholinyl, 4-alkylhexahydro-1H-1,4-diazepin-1-yl, 4-alkyl-1-piperazinyl, 4-(alkylsulphonyl)-1-piperazinyl, 4-(dialkylaminoalkyl)-1-piperazinyl, 1-alkyl-4-piperidinyl or piperidinyl group, by a 4-methyl-1-piperazinyl group, a N-methyl-N-(1'-methyl-[1,4']bipiperidinyl-1-yl)amino or 4-(1-piperidinylmethyl)-1-piperidinyl group:
acidolysis of compounds of general formula

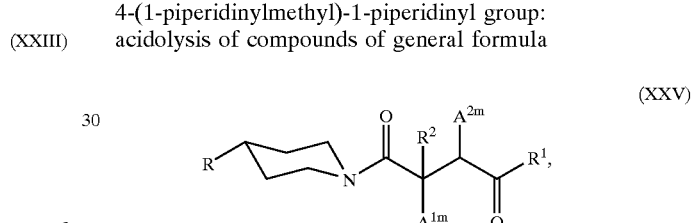

(XXV)

wherein one of the two groups $A^{1m}$ and $A^{2m}$ denotes the hydrogen atom and the other denotes the group

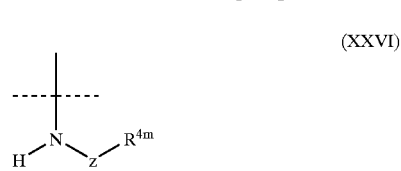

(XXVI)

where R, $R^1$ and $R^2$ and Z are as hereinbefore defined and $R^{4m}$ denotes a branched or unbranched alkyl group comprising 1 to 7 carbon atoms which carries a tert.alkoxycarbonylamino group in the α position and may be substituted in the ω position by an amino, phenyl, pyridinyl, phenoxy, phenylamino, phenylmethoxycarbonylamino or N-alkylphenylamino group, by a dialkylamino group, by a piperidinyl or piperazinyl group optionally substituted by a phenyl, pyridinyl, dimethylamino, 4-morpholinyl, 4-alkyl-hexahydro-1H-1,4-diazepin-1-yl, 4-alkyl-1-piperazinyl, 4-(alkylsulphonyl)-1-piperazinyl, 4-(dialkylaminoalkyl)-1-piperazinyl, 1-alkyl-4-piperidinyl or piperidinyl group, by a 4-methyl-1-piperazinyl group, a N-methyl-N-(1'-methyl-[1,4']bipiperidinyl-1-yl)amino or 4-(1-piperidinylmethyl)-1-piperidinyl group.

Acidolysis with trifluoroacetic acid is preferred, working with or without inert solvents, e.g. dichloromethane, and preferably in the absence of water. Suitable temperatures are between −50 and +90° C., preferably between 0° C. and room temperature. It has also proved satisfactory to carry out the acidolysis of compounds of general formula (XXVI) with methanolic hydrochloric acid solution under reflux conditions, although experience has shown that an attack on carboxamide and ester functions cannot be entirely ruled out, which is why the trifluoroacetic acid variant is generally the method of choice.

n) In order to prepare compounds of general formula (I) wherein one of the two groups $A^1$ and $A^2$ denotes the hydrogen atom and the other denotes the group

(II)

wherein $R^3$ and Z are as hereinbefore defined and $R^4$ denotes a branched or unbranched alkyl group comprising 1 to 7 carbon atoms which is substituted in the α position by an amino or an {{{[1,4']bipiperidinyl-1'-yl}-acetyl}amino} group and in the ω position by a free amino group: acidolysis of compounds of general formula

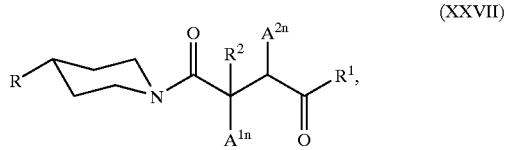

(XXVII)

wherein one of the two groups $A^{1n}$ and $A^{2n}$ denotes the hydrogen atom and the other denotes the group

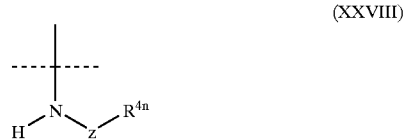

(XXVIII)

where R, $R^1$, $R^2$ and Z are as hereinbefore defined and $R^{4n}$ denotes a branched or unbranched alkyl group comprising 1 to 7 carbon atoms which is substituted in the α position by an amino or {{{[1,4']bipiperidinyl-1'-yl}-acetyl}amino} group and in the ω position by a phenylmethoxycarbonylamino group.

The acidolysis is carried out with hydrogen bromide in organic acids, such as trifluoroacetic acid, pivalic acid, isobutyric acid, isovaleric acid, but preferably in acetic acid, and at temperatures between 0 and 40° C., but preferably at room temperature, and preferably in the presence of excipients such as anisole, thioanisole, pentamethylbenzene or dimethylsulphide.

The new substituted piperidines of general formula (I) according to the invention contain at least one chiral centre. If one of the groups R, $A^1$ or $A^2$ is also chiral, the compounds may occur in the form of two diastereomeric pairs of antipodes. The invention includes the individual isomers and the mixtures thereof.

The diastereomers may be separated on the basis of their different physico-chemical properties, e.g. by fractional crystallisation from suitable solvents, by high pressure liquid or column chromatography, using chiral or preferably non-chiral stationary phases.

Racemates covered by general formula (I) may be separated for example by HPLC on suitable chiral stationary phases (e.g. Chiral AGP, Chiralpak AD). Racemates which contain a basic or acidic function can also be separated via the diastereomeric, optically active salts which are produced on reacting with an optically active acid, for example (+) or (−)-tartaric acid, (+) or (−)-diacetyl tartaric acid, (+) or (−)-monomethyl tartrate or (+)-camphorsulphonic acid, or an optically active base, for example with (R)-(+)-1-phenylethylamine, (S)-(−)-1-phenylethylamine or (S)-brucine.

According to a conventional method of separating isomers, the racemate of a compound of general formula (I) is reacted with one of the abovementioned optically active acids or bases in equimolar amounts in a solvent and the resulting crystalline, diastereomeric, optically active salts thereof are separated using their different solubilities. This reaction may be carried out in any type of solvent provided that it is sufficiently different in terms of the solubility of the salts. Preferably, methanol, ethanol or mixtures thereof, for example in a ratio by volume of 50:50, are used. Then each of the optically active salts is dissolved in water, neutralised with a base such as sodium carbonate or potassium carbonate, sodium hydroxide solution or potassium hydroxide solution and in this way the corresponding free compound is obtained in the (+) or (−) form.

The (R) or (S) enantiomer alone or a mixture of two optically active diastereomeric compounds covered by general formula I may also be obtained by performing the syntheses described above with a suitable reaction component in the (R) or (S) configuration.

The starting compounds of general formula (III) may be obtained analogously to methods known from the literature from α-amino-γ-oxo-arenobutanoic acids (cf. for example: J. E. Nordlander, M. J. Payne, F. G. Njoroge, V. M. Vishwanath, G. R. Han, G. D. Laikos and M. A. Balk, J. Org. Chem. 50, 3619 (1985)) or β-amino-γ-oxo-arenobutanoic acids (cf. e.g.: M. Seki, H. Kubota, T. moriya, M. Yamagishi, S. Nishimoto and K. Matsumoto, Chem. pharm. Bull. (Japan) 34, 4516–4522 (1986); K. Basheeruddin, A. A. Siddiqui, N. H: Khan and S. Saleha, Synth. Commun. 9, 705–712 (1979); S. Ceriani and G. Tarzia, Ann. Chim. (Rom) 63, 457–466 (1973)) or the derivatives thereof. The starting compounds of general formula (IV) which are not known from the literature or even commercially obtainable, may be obtained according to the processes described in WO 98/11128 and DE 199 52 146. Starting compounds of general formula (V) may be prepared from compounds of general formula (III) by derivatisation in the usual way. The carboxylic acids of general formula (VI) required as starting compounds are commercially obtainable or may be prepared by known methods. The starting compounds of general formulae VII and VII' may be obtained by the process e) described hereinbefore. The carboxylic acid derivatives of general formula (IX) are either known or may be obtained analogously to methods known from the literature from the starting compounds of general formula (VI). The starting compounds of general formula X may be prepared from corresponding precursor products according to the processes a) and b) given hereinbefore. The starting compounds of general formulae (XII) and (XII') are either commercially obtainable or may be prepared by methods known from the literature. The starting compounds of general formulae (XIII) and (XV) are also commercially obtainable or known from the literature. The compounds of general formula VII" required as starting compounds may be prepared from amines of general formulae VII or VII' by reacting with sulphates of general formula

Nu'—SO$_2$—Nu"  (XXI)

wherein Nu' is defined as in h) and Nu", which may be different from Nu' or may assume the same meanings as Nu'. The preferred sulphate is the cyclic compound XXII

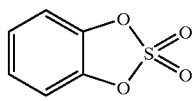

(XXII)

(cf. also: G. E. DuBois and R. A. Stephenson, J. Org. Chem. 45, 5371–5373 [1980]). The starting materials of general formula XVIII may be obtained from the compounds of general formulae VII or VII' described hereinbefore by reaction, in the presence of triethylamine, for example, with mainly commercially obtainable compounds of general formula

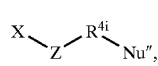

(XXIII)

wherein X denotes a halogen atom, such as chlorine, bromine or iodine. The starting compounds of general formulae (XX) and (XX') may be obtained by the methods given in DE 199 52 146, but may also be formed in situ from suitably substituted 4-aryl-4-oxobutyric acid piperidides which all carry an amino, alkylamino or dialkylamino group in the 2 position. The starting compounds of general formulae (XXI) and (XXVII) come under the definition of general formula (I) and can be prepared using the processes described hereinbefore. The starting compounds of general formula (XXIII) may easily be prepared, for example, from those compounds of general formula (I) wherein $A^1$ or $A^2$ denotes an optionally alkyl-substituted amino group, by reacting with suitable acid chlorides or bromides in known manner. The starting compounds of general formula (XXV) are also prepared from compounds of general formula (I) by reaction with suitably substituted carboxylic acids or carboxylic acid derivatives which are commercially obtainable or easily produced by known methods under the conditions of process c) or d).

The compounds of general formula I obtained may, if they contain basic functions, be converted, particularly for pharmaceutical use, into their physiologically acceptable salts with inorganic or organic acids. Suitable acids include for example hydrochloric acid, hydrobromic acid, phosphoric acid, nitric acid, sulphuric acid, methanesulphonic acid, p-toluenesulphonic acid, acetic acid, fumaric acid, succinic acid, lactic acid, mandelic acid, malic acid, citric acid, tartaric acid or maleic acid.

Moreover, the new compounds of formula (I), if they contain an acid function, for example a carboxy group, may if desired be converted into the addition salts thereof with inorganic or organic bases, particularly for pharmaceutical use into the physiologically acceptable addition salts thereof. Suitable bases for this include, for example, sodium hydroxide, potassium hydroxide, ammonia, cyclohexylamine, dicyclohexylamine, ethanolamine, diethanolamine and triethanolamine.

The new compounds of general formula I and the physiologically acceptable salts thereof have CGRP-antagonistic properties and exhibit good affinities in CGRP receptor binding studies. The compounds display CGRP-antagonistic properties in the pharmacological test systems described hereinafter.

The following experiments were carried out to demonstrate the affinity of compounds of general formula I for human CGRP-receptors and their antagonistic properties:
A. Binding Studies with SK-N-MC Cells (Expressing the Human CGRP Receptor)

SK-N-MC cells are cultivated in "Dulbecco's modified Eagle medium". The medium is removed from confluent cultures. The cells are washed twice with PBS buffer (Gibco 041-04190 M), detached by the addition of PBS buffer, mixed with 0.02% EDTA, then detached again and isolated by centrifuging. After resuspension in 20 ml of "Balanced Salts Solution" [BSS (in mM): NaCl 120, KCl 5.4, NaHCO$_3$ 16.2, MgSO$_4$ 0.8, NaHPO$_4$ 1.0, CaCl$_2$ 1.8, D-glucose 5.5, HEPES 30, pH 7.40] the cells are centrifuged twice at 100×g and resuspended in BSS. After the number of cells has been determined, the cells are homogenised using an Ultra-Turrax and centrifuged for 10 minutes at 3000×g. The supernatant is discarded and the pellet is recentrifuged in Tris buffer (10 mM Tris, 50 mM NaCl, 5 mM MgCl$_2$, 1 mM EDTA, pH 7.40), enriched with 1% bovine serum albumin and 0.1% bacitracin) and resuspended (1 ml/1000000 cells). The homogenised product is frozen at −80° C. The membrane preparations are stable for more than 6 weeks under these conditions.

After thawing, the homogenised product is diluted 1:10 with assay buffer (50 mM Tris, 150 mM NaCl, 5 mM MgCl$_2$, 1 mM EDTA, pH 7.40) and homogenised for 30 seconds with an Ultra-Turrax. 230 µl of the homogenised product are incubated for 180 minutes at ambient temperature with 50 pM $^{125}$I-iodotyrosyl-Calcitonin-Gene-Related Peptide (Amersham) and increasing concentrations of the test substances in a total volume of 250 µl. The incubation is ended by rapid filtration through GF/B-glass fibre filters treated with polyethyleneimine (0.1%) using a cell harvester. The protein-bound radioactivity is measured using a gamma counter. Non-specific binding is defined as the bound radioactivity in the presence of 1 µM human CGRP-alpha during incubation.

The concentration binding curves are analysed using computer-aided non-linear curve matching.

The compounds of general formula I show IC$_{50}$ values ≦10000 nM in the test described.
B. CGRP Antagonism in SK-N-MC Cells SK-N-MC cells (1 million cells) are washed twice with 250 µl incubation buffer (Hanks' HEPES, 1 mM 3-isobutyl-1-methylxanthine, 1% BSA, pH 7.4) and pre-incubated at 37° C. for 15 minutes. After the addition of CGRP (10 µl) as agonist in increasing concentrations ($10^{-11}$ to $10^{-6}$ M), or additionally the substance in 3 to 4 different concentrations, the mixture is incubated for another 15 minutes.

Intracellular cAMP is then extracted by the addition of 20 µl of 1M HCl and centrifugation (2000×g, 4° C., for 15 minutes). The supernatants are frozen in liquid nitrogen and stored at −20° C.

The cAMP contents of the samples are determined by radioimmunoassay (Messrs. Amersham) and the pA$_2$ values of antagonistically acting substances are determined graphically.

The compounds of general formula I exhibit CGRP-antagonistic properties in the in vitro test model described, in a dosage range of between $10^{-11}$ to $10^{-5}$ M.

In view of their pharmacological properties the compounds of general formula I and the salts thereof with physiologically acceptable acids or bases are thus suitable for the acute and prophylactic treatment of headaches, particularly migraine or cluster headaches. Moreover, the compounds of general formula I also have a positive effect on the following diseases: non-insulin-dependent diabetes mellitus ("NIDDM"), cardiovascular diseases, morphine tolerance, skin diseases, particularly thermal and radiation-induced skin damage including sunburn, inflammatory diseases, e.g. inflammatory diseases of the joints (arthritis), inflammatory lung diseases, allergic rhinitis, asthma, diseases accompanied by excessive vasodilatation and consequent reduced circulation of blood through the tissues, e.g. shock and sepsis. The symptoms of menopausal hot flushes in oestrogen-deficient women caused by vasodilatation and increased blood flow are favourably affected by the CGRP-antagonists of the present application in a preventive and acute-therapeutic capacity, this therapeutic approach being distinguished from hormone replacement by the absence of side effects. Furthermore, the compounds of general formula I have an alleviating effect on pain in general.

The dosage required to achieve a corresponding effect is conveniently 0.001 to 30 mg/kg of body weight, preferably 0.01 to 5 mg/kg of body weight, when administered intravenously or subcutaneously and 0.01 to 50 mg/kg of body weight, preferably 0.1 to 30 mg/kg of body weight when administered orally, nasally or by inhalation, 1 to 3× a day in each case.

For this, the compounds of general formula I prepared according to the invention, optionally combined with other active substances such as e.g. antiemetics, prokinetics, neuroleptics, antidepressants, neurokinine antagonists, anticonvulsants, histamine-H1 receptor antagonists, antimuscarinics, β-blockers, α-agonists and α-antagonists, ergot alkaloids, mild analgesics, non-steroidal antiinflammatories, corticosteroids, calcium antagonists, 5-$HT_{1D}$ agonists or other anti-migraine agents, together with one or more inert conventional carriers and/or diluents, e.g. with corn starch, lactose, glucose, microcrystalline cellulose, magnesium stearate, polyvinyl pyrrolidone, citric acid, tartaric acid, water, water/ethanol, water/glycerol, water/sorbitol, water/polyethyleneglycol, propyleneglycol, cetylstearyl alcohol, carboxymethylcellulose or fatty substances such as hard fat or suitable mixtures thereof, may be formulated into conventional galenic preparations such as plain or coated tablets, capsules, powders, suspensions, solutions, metere dose aerosols or suppositories.

The active substances which may be used for the above-mentioned combinations thus include, for example, meloxicam, ergotamine, dihydroergotamine, metoclopramide, domperidone, diphenhydramine, cyclizine, promethazine, chlorpromazine, dexamethasone, flunarizine, dextropropoxyphene, meperidine, propranolol, nadolol, atenolol, clonidine, indoramine, carbamazepine, phenytoin, valproate, amitryptilin, lidocaine, diltiazem or sumatriptan and other 5-$HT_{1D}$-agonists such as, for example, naratriptan, zolmitriptan, avitriptan, rizatriptan and eletriptan. The dosage of these active substances is expediently ⅕ of the lowest recommended dose to ¼ of the normally recommended dose, i.e. for example 20 to 100 mg of sumatriptan.

The invention further relates to the use of the compounds of general formula I as valuable adjuvants for the production and purification (by affinity chromatography) of antibodies as well as, after suitable radioactive labelling, for example by direct labelling with $^{125}I$ or $^{131}I$ or by tritiation of suitable precursors, for example by replacing halogen atoms with tritium, in RIA and ELISA assays and as a diagnostic or analytical adjuvant in neurotransmitter research.

The Examples which follow are intended to illustrate the invention:

Preliminary Remarks:

Satisfactory elementary analyses, IR, UV, $^1$H-NMR and generally also mass spectra have been obtained for all the compounds. Unless otherwise stated, $R_f$ values were obtained using ready-made silica gel TLC plates 60 $F_{254}$ (E. Merck, Darmstadt, Item no. 1.05714) without chamber saturation. If no detailed information is given as to the configuration, it is not clear whether it is a pure enantiomer or whether partial or even complete racemisation has occurred. The following eluants or mixtures of eluants were used for the chromatography:

FM A=ethyl acetate/methanol 100/5 v/v

FM B=ethyl acetate/methanol 80/20 v/v

FM C=ethyl acetate/methanol/conc. ammonia 80/20/1 v/v/v

FM D=dichloromethane/cyclohexane/methanol/conc. ammonia 70/15/15/2 v/v/v/v

FM E=ethyl acetate/glacial acetic acid 99/1 v/v

FM F=ethyl acetate/methanol/glacial acetic acid 90/10/1 v/v/v

FM G=dichloromethane/methanol/conc. ammonia 90/10/1 v/v/v

FM H=petroleum ether/ethyl acetate 1/1 v/v

FM I=dichloromethane/methanol/glacial acetic acid 90/10/1.5 v/v/v

FM K=dichloromethane/isopropanol 9/1 v/v

FM L=ethyl acetate/methanol 9/1 v/v

FM M=dichloromethane/methanol/conc. ammonia 75/25/0.5 v/v/v

FM N=dichloromethane/ethyl acetate 1/1 v/v

FM O=dichloromethane/methanol 95/5 v/v

FM P=dichloromethane/ethyl acetate/cyclohexane/methanol/conc. ammonia 60/16/5/5/0.6 v/v/v/v/v FM Q=dichloromethane/methanol/conc. ammonia 90/10/0.5 v/v/v FM R=dichloromethane/methanol/glacial acetic acid 80/20/1 v/v/v The following abbreviations are used in the description of the experiments:

Mp.: melting point (D): (decomposition)

DIEA: N,N-diisopropyl-ethylamine

Boc: (1,1-dimethylethoxy)carbonyl

TBTU: 2-(1H-benzotriazol-1-yl)-1,1,3,3-tetramethyluronium-tetrafluoroborate

HOBt: 1-hydroxybenzotriazole-hydrate

CDT: 1,1'-carbonyldi-(1,2,4-triazole)

THF: tetrahydrofuran

DMF: dimethyl formamide

EE: ethyl acetate

PE: petroleum ether

LM: solvents

RT room temperature

I. No.: Item number

The meanings of the symbols consisting of letters and numbers used in the Examples are shown in the following summary:

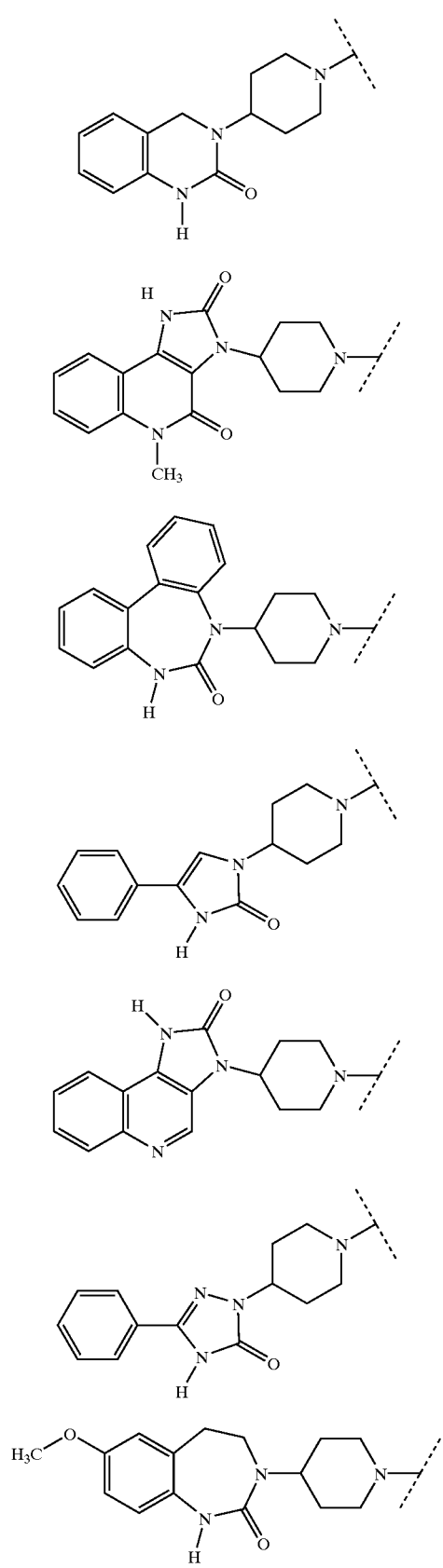
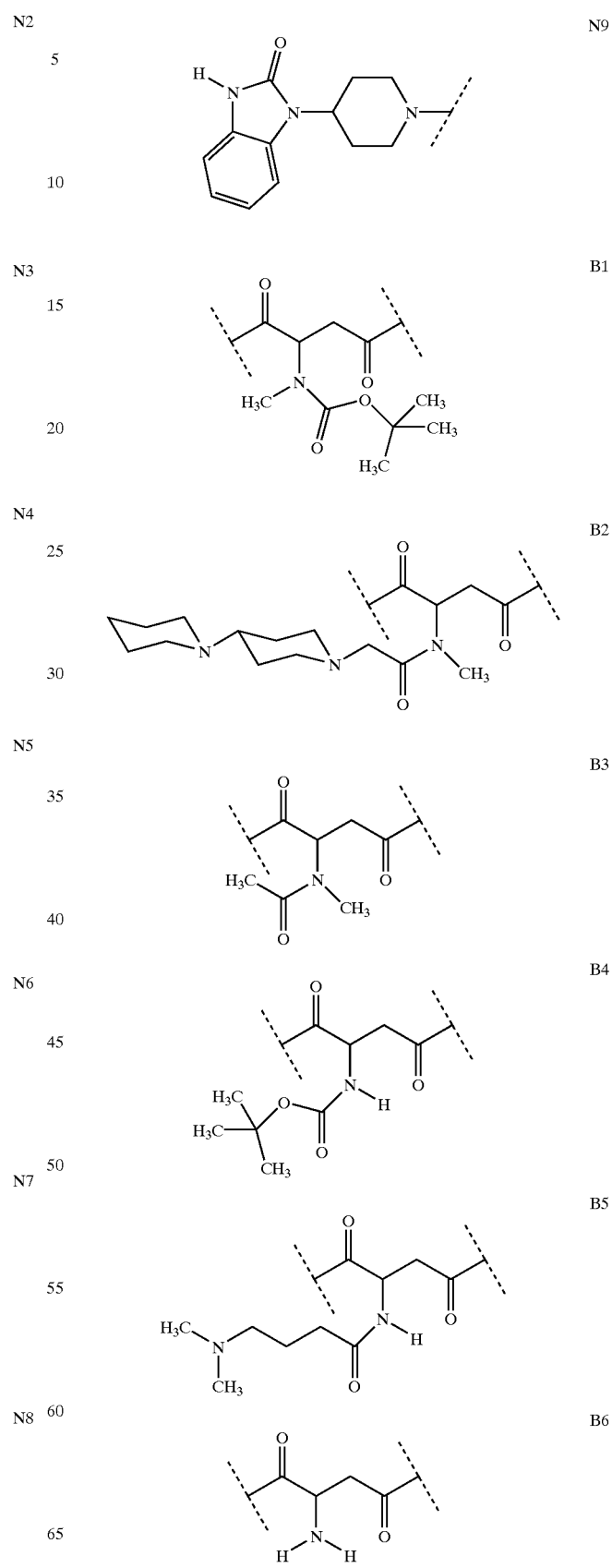

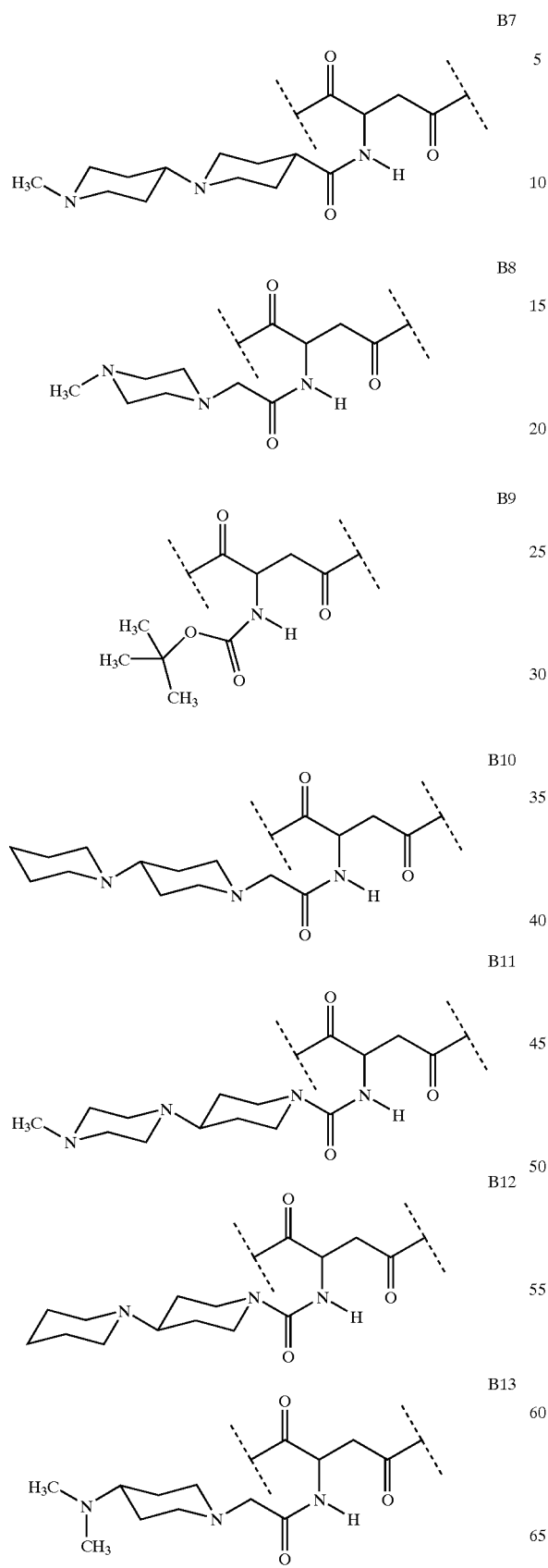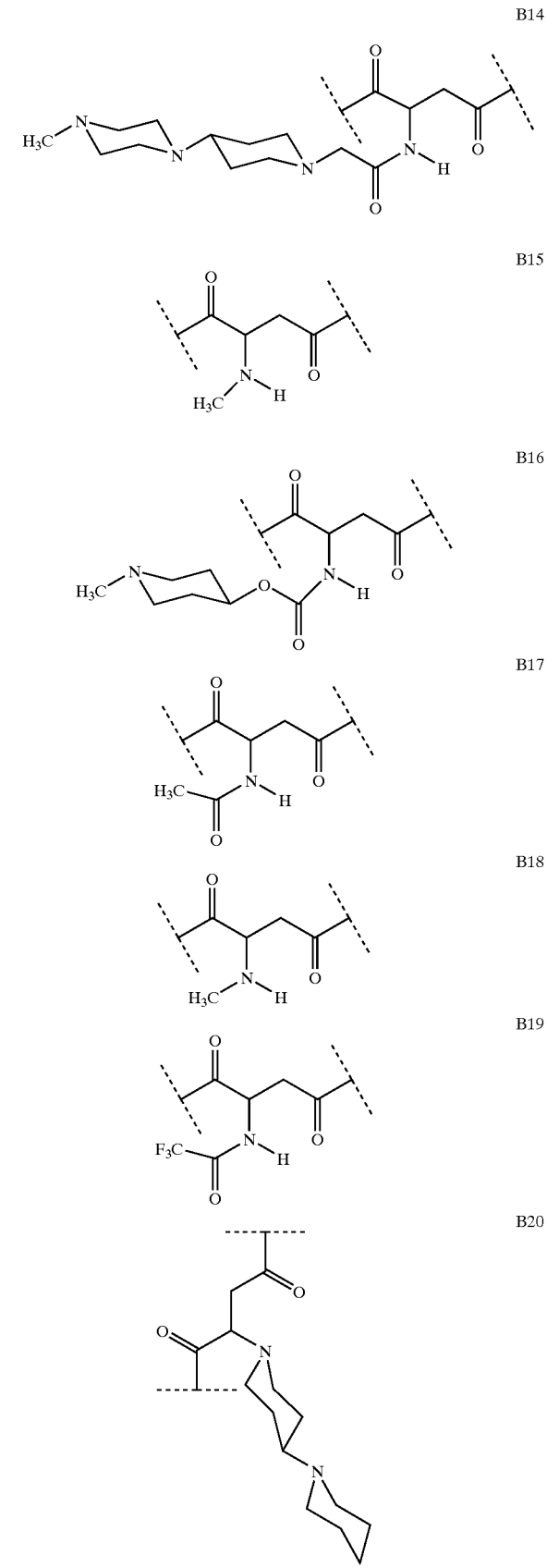

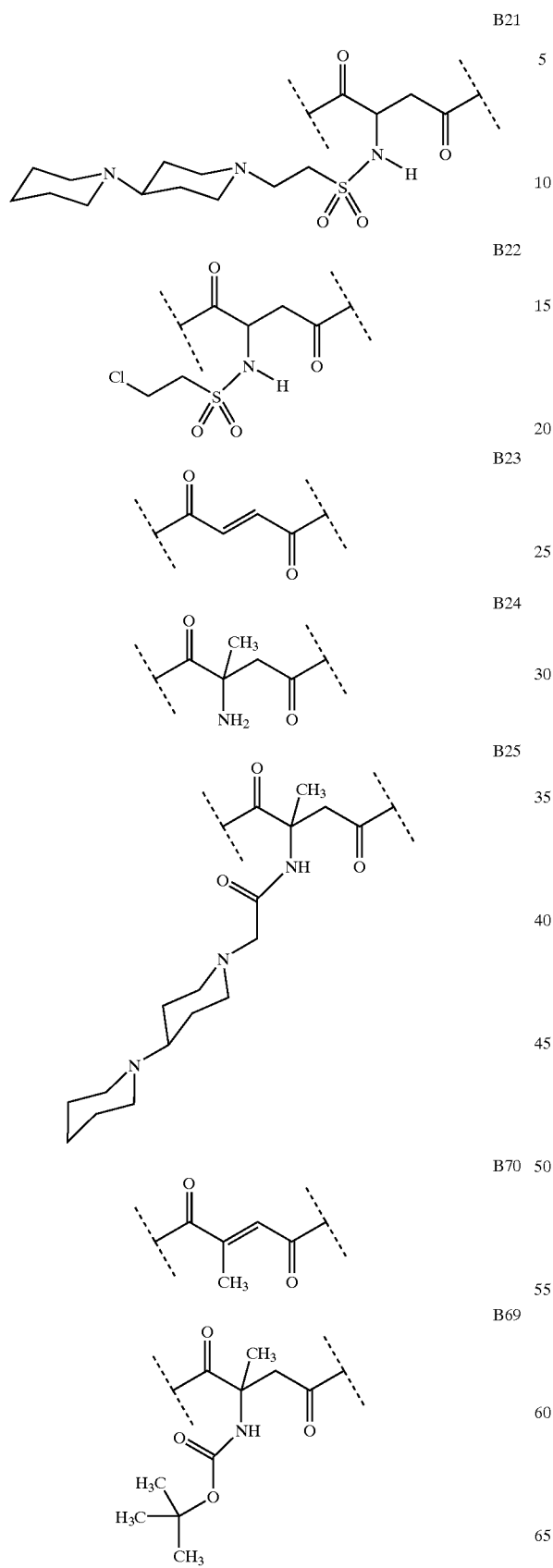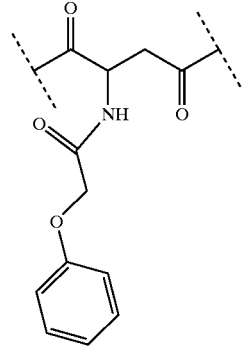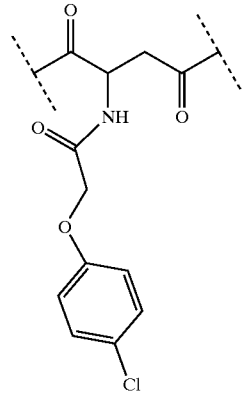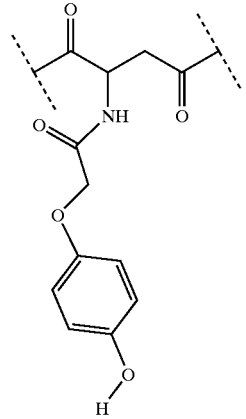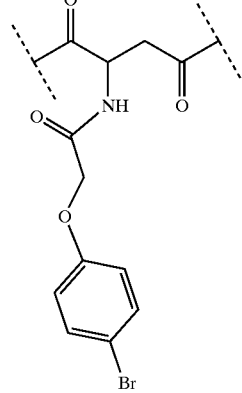

B30 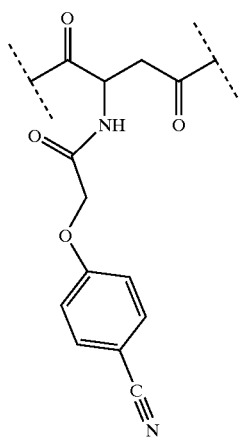
B31 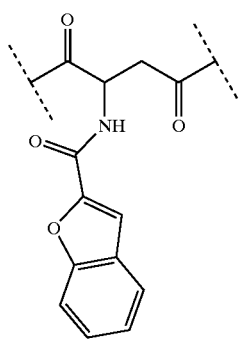
B32 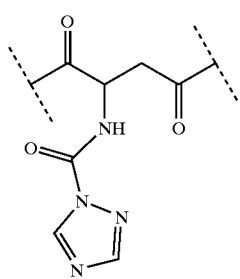
B33 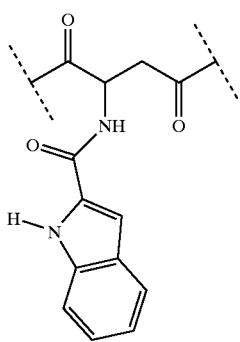
B34 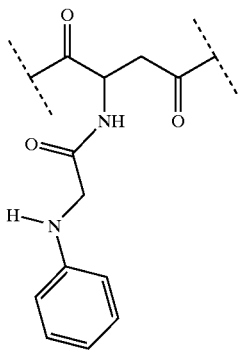
B35 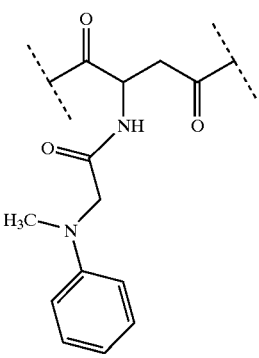
B36 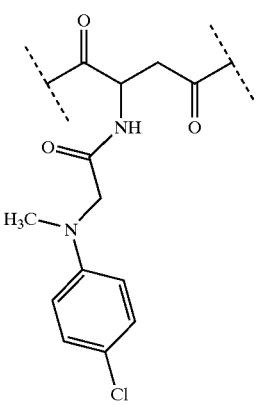
B37 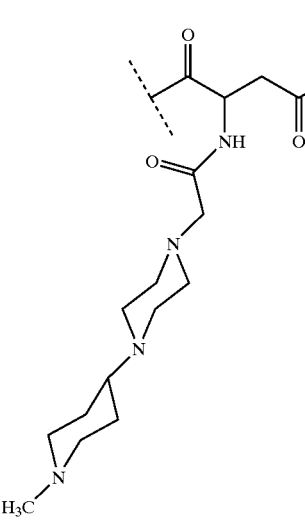

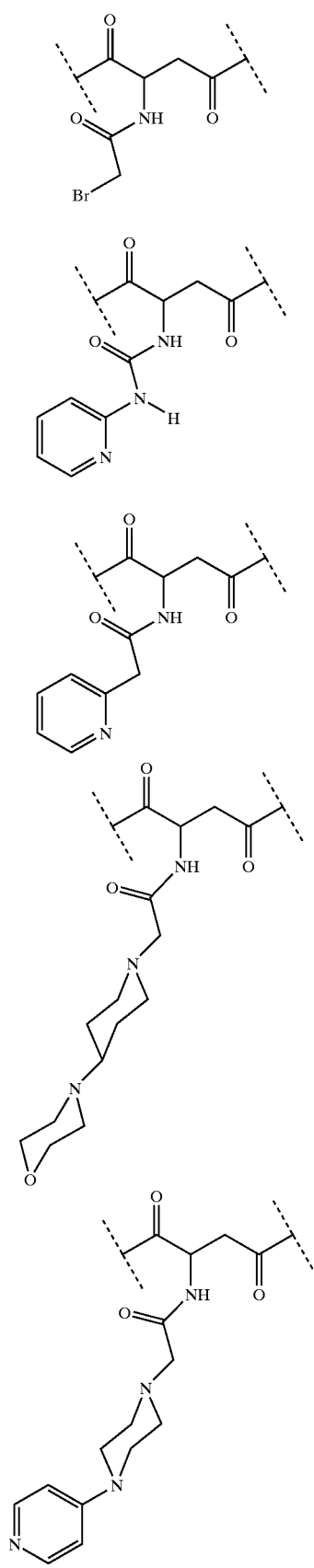
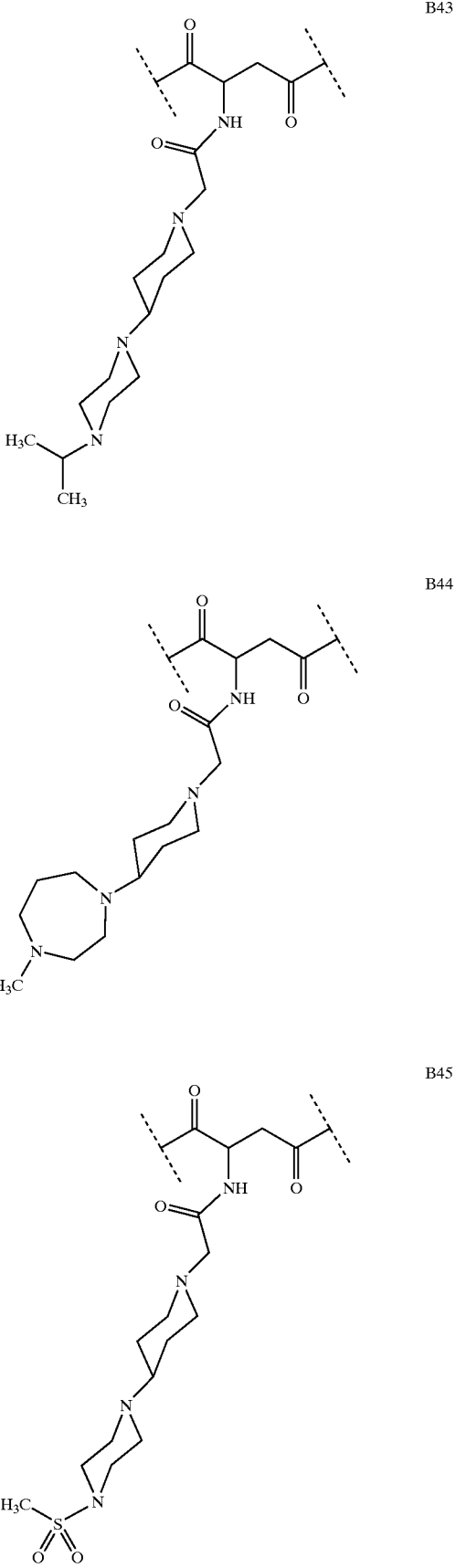

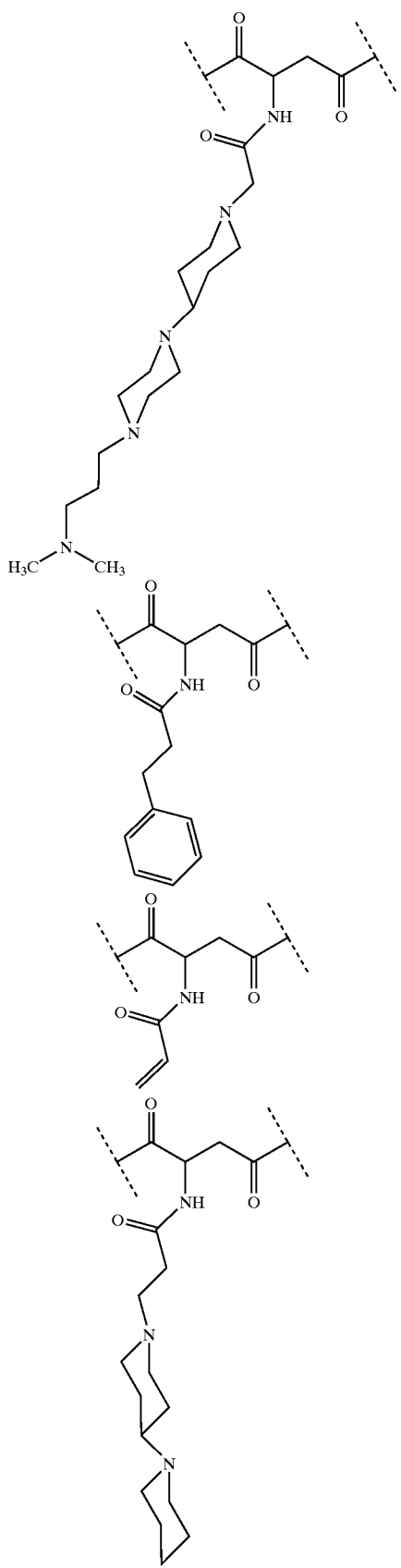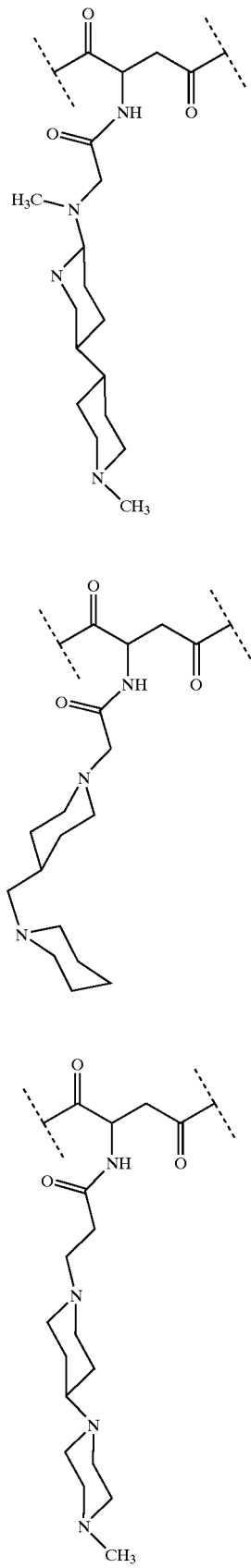

B53
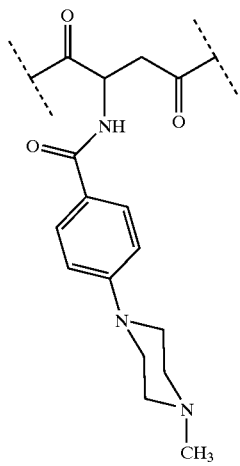
B54
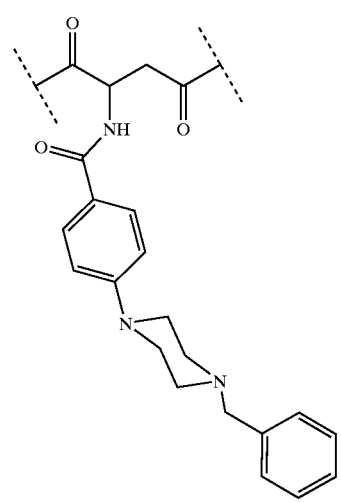
B55
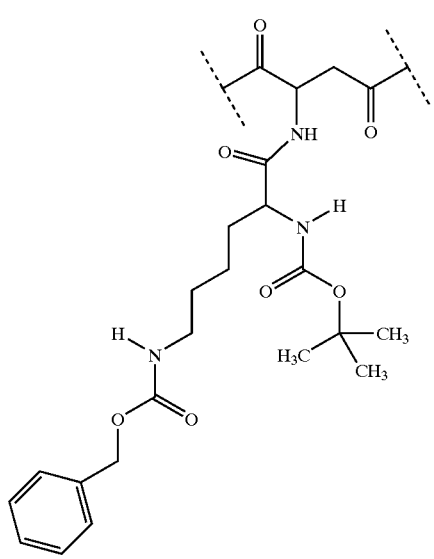
B56
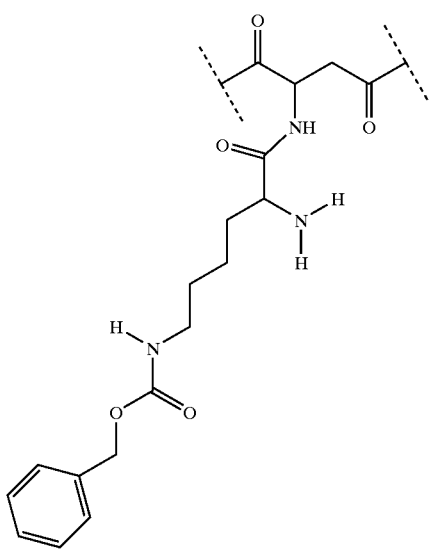
B57
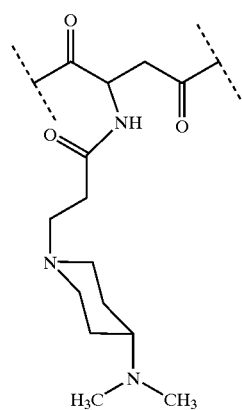
B58
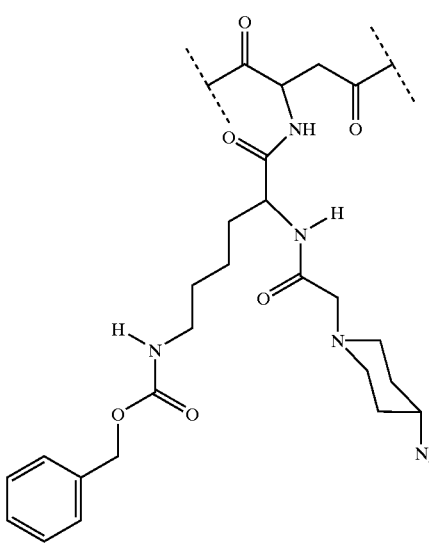

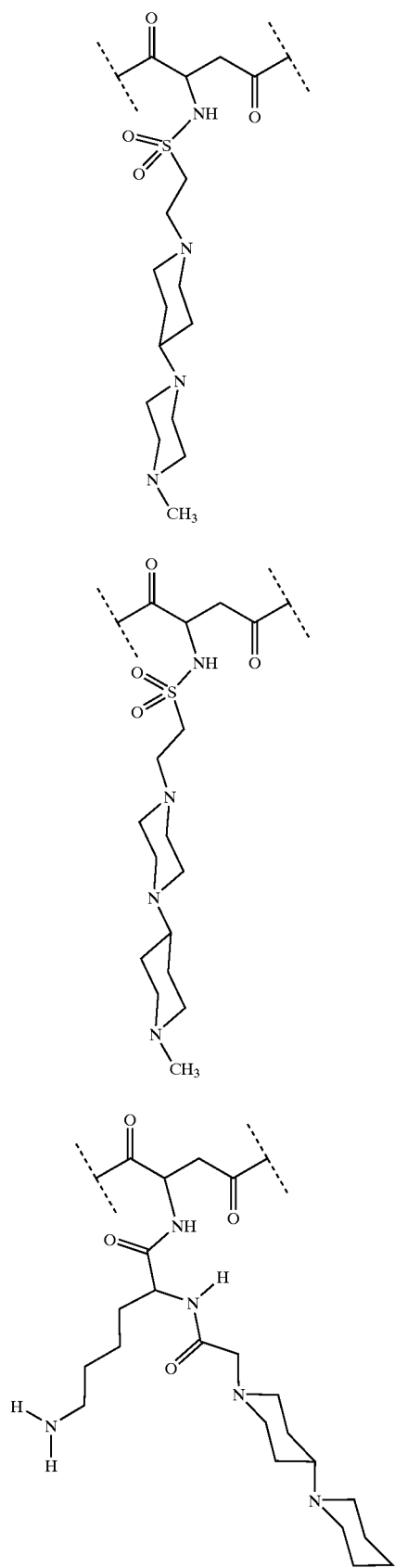
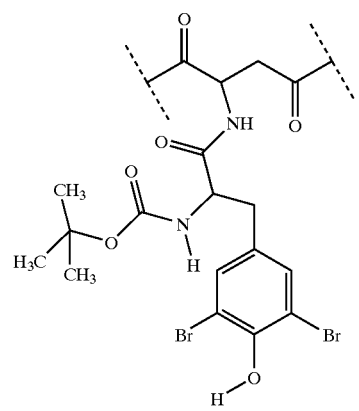
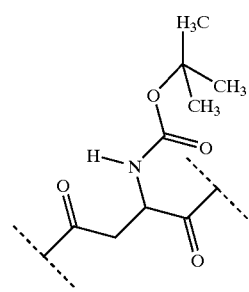
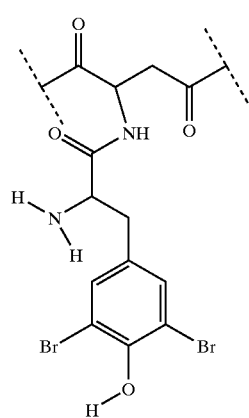
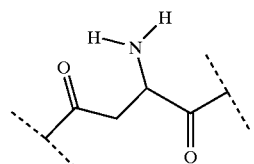
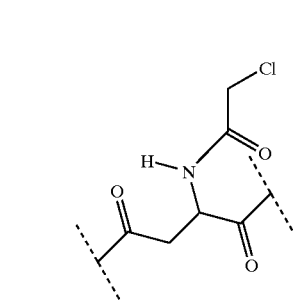

| | |
|---|---|
| B66 | 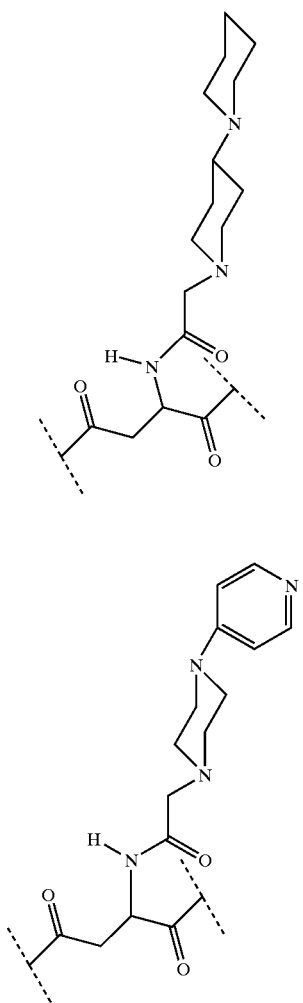 |
| B67 | |
| B68 | |
| C1 | 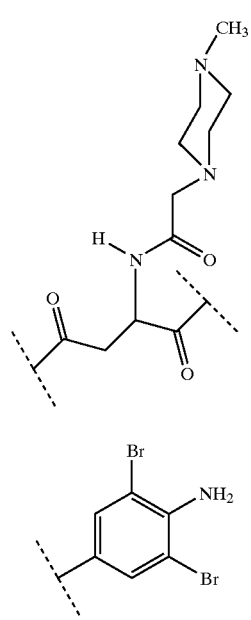 |

| | |
|---|---|
| C2 | 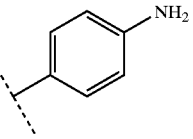 |
| C3 | 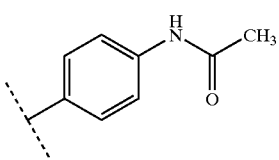 |
| C4 | 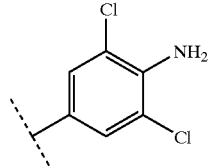 |
| C5 | 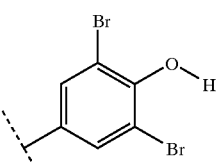 |
| C6 | 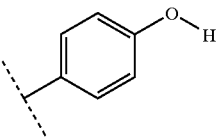 |

A. Preparation of Intermediate Compounds

EXAMPLE A1

(R,S)-4-amino-3,5-dibromo-α-[(1,1-dimethylethoxycarbonyl)-amino]-γ-oxo-benzenebutanoic acid 3.492 g (0.016 mol) of di-t-butyl-dicarbonate were added to the mixture of 6.5 g (0.01454 mol) of (R,S)-α,4-diamino-3,5-dibromo-γ-oxo-benzenebutanoic acid-hydrobromide, 100 ml of dioxane, 50 ml water and 1.59 g (0.015 mol) of anhydrous sodium carbonate and the mixture was stirred overnight at room temperature. The dioxane was eliminated in vacuo, the residue was acidified with 1 M aqueous potassium hydrogen sulphate solution and exhaustively extracted with ethyl acetate. The combined ethyl acetate extracts were dried over sodium sulphate and evaporated down in vacuo. The residue remaining was thoroughly triturated with diethylether, suction filtered and dried in vacuo. 5.0 g (74% of theory) of colourless crystals were obtained.

IR (KBr): 1704, 1691 cm$^{-1}$ (C=O)

ESI-MS: (M+H)$^+$=463/465/467 (Br$_2$).

The following were prepared analogously:

| N | B | C | Remarks | % yield | FM | $R_f$ | MS | IR [cm$^{-1}$] | Mp. [° C.] |
|---|---|---|---------|---------|-----|------|-----|----------------|------------|
| HO | B9 | C4 | from HO-B6-C4, Boc$_2$O and Na$_2$CO$_3$ in dioxan/H$_2$O | 52 | | | ESI: (M − H)$^-$ = 375/377/379 (Cl$_2$) | 3471, 3379 (NH, NH$_2$); 1716, 1689, 1672 (C=O) | Colourless crystals |
| EtO | B69 | C1 | from EtO-B24-C1, Boc$_2$O and NEt$_3$ in THF | 80 | FM G | 0.89 | ESI: (M − H)$^-$ = 505/507/509 (Br$_2$) | 3481, 3429, 3361 (NH, NH$_2$); 1738, 1697, 1678 (C=O) | Colourless crystals |
| HO | B71 | C5 | from HO-B64-C5, Boc$_2$O and Na$_2$CO$_3$ in dioxan/H$_2$O | 55 | | | ESI: (M + H)$^+$ = 464/466/468 (Br$_2$) | 1707, 1691 (C=O) | Colourless crystals |

EXAMPLE A2
(R,S)-α,4-diamino-3,5-dibromo-γ-oxo-benzenebutanoic acid-hydrobromide 5.822 ml (0.1067 mol) of bromine were added dropwise to a solution of 14.7 g (0.0523 mol) of (R,S)-α,4-diamino-γ-oxo-benzenebutanoic acid-dihydrochloride in 150 ml of 70% aqueous acetic acid and the mixture was stirred for 2 hours at a reaction temperature of 70° C. The mixture was evaporated down in vacuo, the residue was triturated with diethylether, suction filtered and dried in vacuo. 21.5 g (92% of theory) of a colourless, crystalline substance.

IR (KBr): 1664 cm$^{-1}$ (C=O)
ESI-MS: (M+H)$^+$=365/367/369 (Br$_2$).

The following were prepared accordingly:

| N | B | C | Remarks | % yield | FM | $R_f$ | MS | IR [cm$^{-1}$] | Mp. [° C.] |
|---|---|---|---------|---------|-----|------|-----|----------------|------------|
| HO | B64 | C5 | from HO-B6-C6*HBr and Br$_2$ in 70% aq. acOH | 71 | | | ESI: (M + H)$^+$ = 366/368/370 (Br$_2$) | 1665 (C=O) | hydrobromide: colourless crystals |

EXAMPLE A3
(R,S)-α,4-diamino-γ-oxo-benzenebutanoic acid-dihydrochloride

The mixture of 18.1 g (0.0523 mol) (R,S)-4-acetylamino-α-trifluoroacetylamino-γ-oxo-benzenebutanoic acid and 200 ml of semi-concentrated hydrochloric acid was refluxed for 2 hours, then evaporated down in vacuo. The residue was triturated thoroughly with tetrahydrofuran, suction filtered and dried in vacuo. 14.1 g (96% of theory) of colourless crystals were obtained.

IR (KBr) 1709, 1678 cm$^{-1}$ (C=O)
ESI-MS: (M+H)$^+$=209.

EXAMPLE A4
(R,S)-4-acetylamino-α-trifluoroacetylamino-γ-oxo-benzenebutanoic acid The mixture of 13.517 g (0.1 mol) of acetanilide and 21.11 g (0.1 mol) of α-trifluoroacetylaminosuccinic anhydride was added to the mixture of 133.341 g (1.0 mol) of anhydrous aluminium chloride and 21.591 ml (0.28 mol) of anhydrous dimethyl formamide whilst maintaining a maximum reaction temperature of 40° C. and the mixture was then kept for 2 hours at 80° C. The cooled reaction mixture was stirred into a mixture of 500 g of crushed ice and 60 ml of conc. hydrochloric acid and extracted exhaustively with ethyl acetate. The combined ethyl acetate extracts were extracted five times with 200 ml of semi-saturated aqueous sodium hydrogen carbonate solution. These aqueous extracts were combined, carefully acidified with hydrochloric acid and again extracted exhaustively with ethyl acetate. The ethyl acetate extracts thus obtained were combined, dried over sodium sulphate, filtered through activated charcoal and evaporated down in vacuo. The residue crystallised out during trituration with diethylether.

Yield: 22.2 g (64% of theory) of colourless crystals, $R_f$ 0.35 (FM F).

IR (KBr): 1741, 1714, 1648 cm$^{-1}$ (C=O).

EXAMPLE A5
[1,4']bipiperidinyl-1'-acetic acid

The mixture of 3.86 g (0.012 mol) of benzyl [1,4'] bipiperidinyl-1'-acetate, 100 ml methanol and 1.0 g palladium black was hydrogenated until the uptake of hydrogen had ceased. The catalyst was filtered off, the filtrate was evaporated down in vacuo and the residue remaining was triturated with diethylether, suction filtered and dried in vacuo.

Yield: 2.13 g (78% of theory).
IR (KBr): 1674 cm$^{-1}$ (C=O)
ESI-MS: (M+H)$^+$=227; (M−H)$^-$=225; (M+Na)$^+$=249.

EXAMPLE A6
4-(4-methyl-1-piperazinyl)-1-piperidinoacetic acid 500 mg of p-toluenesulphonic acid and 12 ml (0.21 mol) of glacial acetic acid were added to a solution of 10.0 g (135.069 mmol) of anhydrous glyoxylic acid and 24.76 g (135.08 mmol) of 4-(4-methyl-1-piperazinyl)piperidine in 500 ml tetrahydrofuran, then 37.2 g (175.555 mmol) of sodium triacetoxyborohydride were added in small portions and the mixture was stirred overnight at room temperature. 60 ml of water were added dropwise with further stirring, the tetrahydrofuran solution was decanted off and the product remaining was digested several times with 20 ml of fresh dichloromethane which was then discarded The product was dissolved in 50 ml water, the resulting solution was extracted three times with 30 ml of dichloromethane and evaporated down in vacuo. The residue was thoroughly washed three times with 20 ml of an acetone-dichloromethane mixture (1/1 v/v) and dried in vacuo. The desired product was obtained in the form of colourless crystals in a yield of 18.8 g (58% of theory).
IR (KBr): 1630 cm$^{-1}$ (C=O)
ESI-MS: (M+H)$^+$=242; (M−H)$^−$=240.

EXAMPLE A7

(R,S)-4-amino-3,5-dibromo-α-{[(4-methyl-1-piperazinyl) acetyl]amino}-γ-oxo-benzenebutanoic acid 18 ml of 1M sodium hydroxide solution were added to a solution of 8.7 g (0.01672 mol) of methyl (R,S)-4-amino-3,5-dibromo-α-{[(4-methyl-1-piperazinyl) acetyl]amino}-γ-oxo-benzenebutanoate in 200 ml of methanol and the mixture was stirred overnight at room temperature. Then 18 ml of 1M hydrochloric acid were added dropwise and the mixture was evaporated down in vacuo. The residue was suspended in a mixture of dichloromethane and isopropanol (5/1 v/v) and filtered and the residue was washed thoroughly with the same mixture of solvents. The combined filtrates were freed from the solvent in vacuo, the residue remaining was triturated with diethylether, suction filtered and dried in vacua. 5.6 g (66% of theory) of the desired compound were obtained in the form of colourless crystals.
IR (KBr): 1670 cm$^{-1}$ (C=O)
ESI-MS: (M−H)$^−$=503/505/507 (Br$_2$).
The following was obtained analogously:

| N | B | C | Remarks | % yield | FM | R$_f$ | MS | IR [cm$^{-1}$] | Mp. [° C.] |
|---|---|---|---------|---------|----|----|----|----|----|
| HO | B69 | C1 | from EtO-B69-C1 by saponification with LiOH in H$_2$O/THF 1/4 (v/v) | 88 | FM R | 0.74 | ESI: (M − H)$^−$ = 477/479/481 (Br$_2$) | 3477, 3384 (NH, NH$_2$); 1703 (C=O) | colourless, amorphous substance |

EXAMPLE A8

Benzyl [1,4']bipiperidinyl-1'-acetate

A solution of 3.264 ml (0.019 mol) of DIEA in 50 ml of THF was added dropwise to a solution of 4.0 g (0.01746 mol) of [1,4']bipiperidinyl and 2.08 ml (0.018 mol) of benzyl bromoacetate in 100 ml tetrahydrofuran. The mixture was stirred overnight, then evaporated down in vacuo and the residue was divided between a saturated aqueous sodium hydrogen carbonate solution and ethyl acetate. The organic phase was dried over sodium sulphate and freed from solvent, the residue was taken up in diisopropyl ether and evaporated down again. 3.86 g (70% of theory) of the desired colourless compound were obtained.

IR (KBr): 1751 cm$^{-1}$ (C=O)

ESI-MS: (M+H)$^+$=317.

EXAMPLE A9

Methyl (R,S)-4-amino-3,5-dibromo-α-{[(4-methyl-1-piperazinyl)acetyl]amino}-γ-oxo-benzenebutanoate Prepared analogously to Example 1 from methyl (R,S)-α,4-diamino-3,5-dibromo-γ-oxo-benzenebutanoate hydrobromide, 4-methyl-1-piperazinacetic acid dihydrochloride, TBTU and HOBt in the presence of triethylamine and DMF in a yield of 43% of theory. Colourless crystals, R$_f$ 0.65 (FM D)
IR (KBr): 1751, 1672 cm$^{-1}$ (C=O)
MS: M$^+$=518/520/522 (Br$_2$).
The following were prepared analogously:

| N | B | C | Remarks | % yield | FM | R$_f$ | MS | IR [cm$^{-1}$] | Mp. [° C. |
|---|---|---|---------|---------|----|----|----|----|----|
| N1 | B9 | C4 | from N1-H, HO-B9-C4, TBTU, HOBt and NEt$_3$ in THF | 98 | FM G | 0.45 | ESI: (M − H)$^−$ = 602/604/606 (Cl$_2$); (M + H)$^+$ = 604/606/608 (Cl$_2$); (M + Na)$^+$ = 626/628/630 (Cl$_2$); EI: M$^+$ = 603/605/607 (Cl$_2$) weak | 3336 (NH, NH$_2$); 1709, 1657 (C=O) | colourless crystals |
| N1 | B69 | C1 | from N1-H, HO-B69-C1, TBTU, HOBt and NEt$_3$ in THF | 25 | FM G | 0.55 | ESI: (M − H)$^−$ = 704/706/708 (Br$_2$); (M + Na)$^+$ = 728/730/732 (Br$_2$); | 3348 (NH, NH$_2$); 1707 (C=O) | Colourless amorphous substance |
| N2 | B71 | C5 | from N2-H, HO-B71-C5, TBTU, HOBt and NEt$_3$ in THF | 12 | FM G | 0.51 | ESI: (M − H)$^−$ = 677/679/681 (Br$_2$); (M + Na)$^+$ = 701/703/705 (Br$_2$); | 3348, 3180 (OH, NH); 1710 (C=O) | Colourless amorphous substance |

EXAMPLE A10
(R,S)-2-amino-4-(4-amino-3,5-dichlorophenyl)-1-{4-[2(2H)-oxo-1,3,4,5-tetrahydro-1,3-benzodiazepin-3-yl]-1-piperidinyl}-1,4-butanedione-trifluoroacetate Prepared analogously to Example 2 from (R,S)-4-(4-amino-3,5-dichlorophenyl)-2-[(1,1-dimethylethoxycarbonyl)amino]-1-{4-[2(2H)-oxo-1,3,4,5-tetrahydro-1,3-benzodiazepin-3-yl]-1-piperidinyl}-1,4-butanedione and trifluoroacetic acid in dichloromethane in a quantitative yield. Colourless crystals, $R_f$ 0.41 (FM G).

IR (KBr): 1657 (C=O); 1203, 1176 (trifluoroacetate) cm$^{-1}$

ESI-MS: (M−H)$^-$=502/504/506 (Cl$_2$); (M+H)$^+$=504/506/508 (Cl$_2$).

The following were obtained analogously:

mixture was left to stand overnight at room temperature, the crystals precipitated were suction filtered, washed thoroughly with water and dried at 70° C. in a circulating air drier until a constant weight was achieved. 24.0 g (27% of theory) of pale yellow crystals were obtained.

IR (KBr): 3485, 3365 (NH$_2$); 1711 (C=O) cm$^{-1}$
ESI-MS: (M−H)$^-$=258/260/262 (Cl$_2$)

EXAMPLE A13
(R,S)-4-(4-amino-3,5-dibromophenyl)-2-(2-chloroethanesulphonylamino)-1-{4-[2(2H)-oxo-1,3,4,5-tetrahydro-1,3-benzodiazepin-3-yl]-1-piperidinyl}-1,4-butanedione 0.152 ml (1.414 mmol) of 97% 2-chloroethanesulphonic acid chloride were added dropwise to a mixture of 1.00 g

| N | B | C | Remarks | % yield | FM | $R_f$ | MS | IR [cm$^{-1}$] | Mp. [° C.] |
|---|---|---|---|---|---|---|---|---|---|
| N1 | B24 | C1 | from N1-B69-C1 and CF$_3$CO$_2$H in CH$_2$Cl$_2$ | 100 | FM D | 0.53 | ESI: (M − H)$^-$ = 604/606/608 (Br$_2$); (M + H)$^+$ = 606/608/610 (Br$_2$); (M + Na)$^+$ = 628/630/632 (Br$_2$) | 3460, 3381 (NH, NH$_2$); 1653 (C=O) | trifluoroacetate: Colourless amorphous substance |
| N2 | B64 | C5 | from N1-B71-C5 and CF$_3$CO$_2$H in CH$_2$Cl$_2$ | 98 | FM G | 0.38 | ESI: (M − H)$^-$ = 577/579/581 (Br$_2$); (M + H)$^+$ = 579/581/583 (Br$_2$) | 1660 (C=O) | trifluoroacetate: Colourless amorphous substance |

EXAMPLE A11
(R,S)-α,4-diamino-3,5-dichloro-γ-oxo-benzenebutanoic acid 4.0 g (15.38 mmol) of (E)-4-amino-3,5-dichloro-γ-oxo-benzenebutenoic acid and 100 ml of methanol saturated with ammonia were kept at 30° C. for 4 hours using an intensive cooler packed with dry ice and methanol. The mixture was then freed from solvent, the residue was stirred with diisopropyl ether, suction filtered and dried in vacuo. 3.69 g (87% of theory) of colourless crystals were obtained.

IR (KBr): 3460, 3392, 3338, 3184, 3072 (NH$_2$, OH); 1668 (C=O) cm$^{-1}$

ESI-MS: (M−H)$^-$=275/277/279 (Cl$_2$); (M+H)$^+$=277/279/281 (Cl$_2$).

The following was obtained accordingly:

(1.414 mmol) of (R,S)-2-amino-4-(4-amino-3,5-dibromophenyl)-1-{4-[2(2H)-oxo-1,3,4,5-tetrahydro-1,3-benzodiazepin-3-yl]-1-piperidinyl}-1,4-butanedione-trifluoroacetate (I. No. 18), 0.418 ml (3.0 mmol) of triethylamine and 20 ml dichloromethane while maintaining a reaction temperature of not more than 10° C., the mixture was stirred overnight at room temperature, another 0.3 ml of 2-chloroethanesulphonic acid chloride were added and the mixture was stirred for another 24 hours at room temperature. The solvent was eliminated in vacuo, the residue was divided between 100 ml of water and 100 ml of dichloromethane, the insoluble matter was filtered off, the dichloromethane phase was dried over sodium sulphate and

| N | B | C | Remarks | % yield | FM | $R_f$ | MS | IR [cm$^{-1}$] | Mp. [° C.] |
|---|---|---|---|---|---|---|---|---|---|
| EtO | B24 | C1 | from EtO-B70-C1 and methanolic ammonia solution | 26 | FM G | 0.54 | (M + H)$^+$ = 407/409/411 (Br$_2$); | 3429, 3359, 3317 (NH$_2$); 1736, 1678, (C=O) | Colourless crystals |

EXAMPLE A12
(E)-4-(4-amino-3,5-dichlorophenyl)-4-oxo-2-butenoic acid

The mixture of 69.583 g (0.341 mol) of 1-(4-amino-3,5-dichlorophenyl)-1-ethanone, 47.038 g (0.511 mol) of glyoxylic acid hydrate, 0.8 g of p-toluenesulphonic acid and 500 ml of glacial acetic acid was refluxed for 7 hours. The again evaporated down in vacuo. The residue was purified by column chromatography on silica gel using FM G as eluant. From the appropriate fractions 200 mg (20% of theory) of colourless crystals (diisopropylether) were obtained, $R_f$ 0.52 (FM G) ESI-MS: (M−H)$^-$=716/718/720 (Br$_2$).

The following were obtained accordingly:

| N | B | C | Remarks | % yield | FM | $R_f$ | MS | IR [cm$^{-1}$] | Mp. [° C.] |
|---|---|---|---------|---------|----|----|-----|----------------|------------|
| N1 | B38 | C1 | from N1-B6-C1, bromoacetyl-bromide and NEt$_3$ in CH$_2$Cl$_2$ | 27 | FM G | 0.43 | ESI: (M − H)$^-$ = 710/712/714/716 (Br$_3$); (M + Na)$^+$ = 734/736/738/740 (Br$_3$) | 3331 (NH, NH$_2$); 1653 (C=O) | Colourless crystals |
| N1 | B48 | C1 | from N1-B6-C1, acryloyl chloride and NEt$_3$ in CH$_2$Cl$_2$ | 87 | FM G | 0.34 | ESI: (M − H)$^-$ = 644/646/648 (Br$_2$); (M + Na)$^+$ = 668/670/672 (Br$_2$) | 3327 (NH, NH$_2$); 1657 (C=O) | Colourless crystals |

EXAMPLE A14
Ethyl 4-(4-amino-3,5-dibromophenyl)-2-methyl-4-oxo-2-butenoate

A mixture of 20.0 g (61.546 mmol) of 4-amino-3,5-dibromo-α-oxo-phenylacetaldehyde-hydrate and 22.305 g (61.546 mmol) of ethyl 2-(triphenylphosphylene)-propanoate in 300 ml of THF was prepared with external cooling and while maintaining an internal temperature of 0° C., the mixture was then allowed to come up to RT within 2 hours, stirred overnight at RT, the solvent was eliminated in vacuo and the residue was chromatographed using petroleum ether/ethyl acetate 1/1 (v/v) as eluant on a silica gel column. After the appropriate eluates had been worked up in the usual way, 12.8 g (53% of theory) of colourless crystals were obtained, $R_f$ 0.79 (FM petroleum ether/ethyl acetate 1/1 (v/v).

IR (KBr): 3429, 3330 (NH$_2$); 1712, 1658, (C=O) cm$^{-1}$
ESI-MS: (M−H)$^-$=388/390/392 (Br$_2$); (M+Na)$^+$=412/414/416 (Br$_2$).

EXAMPLE A15
4-Amino-3,5-dibromo-α-oxo-phenylacetaldehyde-hydrate 72.1 g (0.246 mol) of 4-amino-3,5-dibromo-acetophenone was added batchwise to a solution of 27.2 g (0.245 mol) of selenium dioxide in the mixture of 240 ml of dioxane and 8 ml of water and the mixture was then refluxed for 4 hours. While still hot the reaction mixture was clarified with activated charcoal, filtered and diluted with 240 ml water. The pale yellow crystals precipitated after the filtrate had been stirred for one hour were suction filtered, washed thoroughly with water, then suspended in diethylether, suction filtered again and dried in vacuo. Yield: 40.02 g (53% of theory). $R_f$ 0.65 (petroleum ether/ethyl acetate 1/1 v/v).

IR (KBr): 3462, 3354 (NH$_2$); 1676, (C=O) cm$^{-1}$
MS: M$^+$=305/307/309 (Br$_2$).

EXAMPLE A16
(R,S)-β-amino-4-hydroxy-γ-oxobenzenebutanoic acid-hydrobromide

The mixture of 8.0 g (14.5 mmol) of dibenzyl α-(4-benzyloxybenzoyl)-α-formylaminosuccinate and 42 ml of a 33% hydrogen bromide solution in glacial acetic acid was stirred overnight at RT and then for 3 hours at an internal temperature of 50° C. The solvent was eliminated, the residue was dissolved in water and the resulting solution was washed once with ethyl acetate. After evaporation, the aqueous solution left a crystalline product which was used in the following step without further purification.

Yield: 1.0 g (24% of theory).
IR (KBr): 1710, 1680 cm$^{-1}$ (C=O)
ESI-MS: (M+H)$^+$=210.

EXAMPLE A17
Dibenzyl α-(4-benzyloxybenzoyl)-α-formylaminosuccinate 5.3 g (0.02 mol) of crude 4-benzyloxybenzoylchloride were added dropwise to the solution of 6.468 g (0.02 mol) of dibenzyl α-isocyanosuccinate (M. Seki, H. Kubota, T. Moriya, M. Yamagishi, S. Nishimoto and K. Matsumoto, Chem. pharm. Bull. 34, 4516–4522 (1986)) and 6 ml of triethylamine in 15 ml THF, with vigorous stirring and while maintaining a reaction temperature of 27 to 34° C. After it had all been added the mixture was stirred for a further 2 hours at RT and then the volatile substances were eliminated in vacuo. The residue was taken up in 30 ml of ethyl acetate, the suspension obtained was washed three times with 15 ml of water, dried over sodium sulphate and evaporated down. The residue was taken up in 20 ml of 98% formic acid and the resulting mixture was stirred for 3 hours at a temperature of between 40 and 50° C. The formic acid was eliminated in vacuo, the residue was taken up in ethyl acetate, the solution obtained was washed with water, dried over sodium sulphate and evaporated down again. The residue crystallised when triturated with n-hexane. Yield: 8.6 g (78% of theory).

IR (KBr): 3340 (NH$_2$); 1735, 1690, 1640 (C=O) cm$^{-1}$
ESI-MS: (M+H)$^+$=550/552/554.

B. Preparation of the End Compounds

Example 1
(R,S)-4-(4-amino-3,5-dibromophenyl)-2-[(1,1-dimethylethoxycarbonyl)methylamino]-1-{4-[2(2H)-oxo-1,3,4,5-tetrahydro-1,3-benzodiazepin-3-yl]-1-piperidinyl}-1,4-butanedione (I. No. 1)

The mixture of 1.5 g (3.124 mmol) of (R,S)-4-(4-amino-3,5-dibromophenyl)-2-[(1,1-dimethylethoxycarbonyl)methylamino]-4-oxo-butanoic acid, 0.7664 g (3.124 mmol) of 3-(4-piperidinyl)-1,3,4,5-tetrahydro-1,3-benzodiazepin-2 (2H)-one, 1.044 g (3.25 mmol) of TBTU, 0.4304 g (3.18 mmol) of HOBt, 0.479 ml (3.44 mmol) of triethylamine and 50 ml THF was stirred overnight at ambient temperature. The reaction mixture was freed from solvent in vacuo, the residue was taken up in 200 ml of ethyl acetate and the resulting solution was extracted successively with 50 ml of saturated sodium hydrogen carbonate solution, 5% citric acid solution and saturated sodium hydrogen carbonate solution, dried over sodium sulphate and again evaporated down in vacuo. The product obtained was purified by column chromatography on silica gel using dichloromethane/methanol/conc. ammonia (90/10/1 v/v/v) as eluant. After the appropriate eluates had been worked up in the usual way, 1.05 g (48% of theory) of a colourless crystalline product were obtained, $R_f$ 0.65 (FM ethyl acetate)

IR (KBr): 3465, 3329 (NH, NH$_2$); 1652 (C=O) cm$^{-1}$
MS: M$^+$=705/707/709 (Br$_2$);
ESI: (M−H)$^-$=704/706/708 (Br$_2$)
(M+Na)$^+$=728/730/732 (Br$_2$)

The following were prepared analogously:

| Item no. | N | B | C | Remarks | % yield | FM | $R_f$ | MS | IR [cm$^{-1}$] | Mp. [° C.] |
|---|---|---|---|---|---|---|---|---|---|---|
| 2 | N1 | B2 | C1 | From N1-B15-C1, [1,4']bipiperidinyl-1'-acetic acid, TBTU, HOBt and NEt$_3$ in THF | 44 | FM G FM Q | 0.46 0.43 | ESI: (M + H)$^+$ = 814/816/818 (Br$_2$); (M − H)$^-$ = 812/814/816 (Br2) | 1649 (C=O) | colourless crystals |
| 3 | N1 | B3 | C1 | From N1-B18-C1, acetic acid, TBTU, HOBt and NEt$_3$ in THF | 37 | FM G FM Q | 0.48 0.62 | ESI: (M + Na)$^+$ = 670/672/674 (Br$_2$); (M − H)$^-$ = 646/648/650 (Br$_2$) | 1653 (C=O) | colourless crystals |
| 4 | N2 | B4 | C1 | From N2-H, HO-B4-C1, TBTU, HOBt and NEt$_3$ in THF | 69 | AcOEt FM Q | 0.50 0.62 | ESI: (M − H)$^-$ = 676/678/680 (Br$_2$) | 1709, 1666 (C=O) | colourless crystals |
| 5 | N2 | B5 | C1 | From N2-B5-C1, 4-dimethylamino-butanoic acid, TBTU, HOBt and NEt$_3$ in DMF | 38 | FM D FM Q | 0.30 0.20 | ESI: (M + H)$^+$ = 691/693/695 (Br$_2$) | 1666 (C=O) | colourless crystals |
| 7 | N2 | B7 | C1 | From N2-B6-C1, 1'-methyl-[1,4']bipiperidinyl-4-carboxylic acid, TBTU, HOBt and NEt$_3$ in DMF | 22 | FM D FM Q | 0.38 0.15 | ESI: (M + H)$^+$ = 786/788/790 (Br$_2$) | 1664 (C=O) | colourless crystals |
| 8 | N2 | B8 | C1 | From N2-B6-C1, 4-methyl-1-piperazinoacetic acid, TBTU, HOBt and NEt$_3$ in DMF | 50 | FM D FM Q | 0.50 0.34 | ESI: (M + H)$^+$ = 718/720/722 (Br$_2$) | 1668 (C=O) | colourless crystals |
| 9 | N3 | B8 | C1 | From N3-H, HO-B8-C1, TBTU, HOBt and NEt$_3$ in DMF | 30 | FM Q | 0.30 | ESI: (M + H)$^+$ = 785/787/789 (Br$_2$) | 1705 (C=O) | colourless crystals |
| 10 | N4 | B8 | C1 | From N4-H, HO-B8-C1, TBTU, HOBt and NEt$_3$ in DMF | 29 | FM Q | 0.35 | EI: M$^+$ = 779/781/783 (Br$_2$); ESI: (M − H)$^-$ = 778/780/782 (Br$_2$); (M + Na)$^+$ = 802/804/806 (Br$_2$); (M + H)$^+$ = 780/782/784 (Br2) | 1677 (C=O) | colourless crystals |
| 11 | N5 | B8 | C1 | From N5-H, HO-B8-C1, TBTU, HOBt and NEt$_3$ in DMF | 13 | FM Q | 0.28 | ESI: (M + H)$^+$ = 730/732/734 (Br$_2$) | 1680 (C=O) | colourless crystals |
| 12 | N6 | B8 | C1 | From N6-H, HO-B8-C1, TBTU, HOBt and NEt$_3$ in DMF | 22 | FM Q | 0.27 | ESI: (M + H)$^+$ = 755/757/759 (Br$_2$) | 1685 (C=O) | colourless crystals |
| 13 | N7 | B8 | C1 | From N7-H, HO-B8-C1, TBTU, HOBt and NEt$_3$ in DMF | 28 | FM Q | 0.29 | ESI: (M + H)$^+$ = 731/733/735 (Br$_2$) | 1680 (C=O) | colourless crystals |
| 14 | N8 | B8 | C1 | From N8-H, HO-B8-C1, TBTU, HOBt and NEt$_3$ in DMF | 34 | FM Q | 0.36 | ESI: (M + H)$^+$ = 762/764/766 (Br$_2$) | 1653 (C=O) | colourless crystals |
| 15 | N1 | B8 | C1 | From N1-H, HO-B8-C1, TBTU, HOBt and NEt$_3$ in DMF | 14 | FM Q | 0.36 | ESI: (M + H)$^+$ = 732/734/736 (Br$_2$) | 1662 (C=O) | colourless crystals |
| 16 | N9 | B8 | C1 | From N9-H, HO-B8-C1, TBTU, HOBt and NEt$_3$ in DMF | 24 | FM Q | 0.32 | ESI: (M + H)$^+$ = 704/706/708 (Br$_2$) | 1697 (C=O) | colourless crystals |
| 17 | N1 | B9 | C1 | From N1-H, HO-B9-C1, TBTU, HOBt and NEt$_3$ in THF | 53 | acOEt FM Q | 0.65 0.64 | ESI: (M − H)$^-$ = 690/692/694 (Br$_2$) | 1714, 1666 (C=O) | colourless crystals |

| Item no. | N | B | C | Remarks | % yield | FM | $R_f$ | MS | IR [cm$^{-1}$] | Mp. [°C.] |
|---|---|---|---|---|---|---|---|---|---|---|
| 19 | N1 | B10 | C1 | From N1-B6-C1, [1,4']bipiperidinyl-1'-acetic acid, TBTU, HOBt and NEt$_3$ in THF | 67 | FM D FM Q | 0.50 0.43 | ESI: (M + H)$^+$ = 800/802/804 (Br$_2$) | 1653 (C=O) | colourless crystals |
| 22 | N1 | B13 | C1 | From N1-B6-C1, 4-dimethylamino-piperidine-1-acetic acid, TBTU, HOBt and DIEA in THF | 22 | FM Q | 0.36 | ESI: (M − H)$^-$ = 758/760/762 (Br$_2$); (M + H)$^+$ = 760/762/764 (Br$_2$) | 1660 (C=O) | colourless crystals |
| 23 | N1 | B14 | C1 | From N1-B6-C1, 4-(4-methyl-1-piperazinyl)-piperidine-1-acetic acid, TBTU, HOBt and DIEA in THF | 14 | FM Q | 0.47 | ESI: (M − H)$^-$ = 813/815/817 (Br$_2$); (M + H)$^+$ = 815/817/819 (Br$_2$) | 1660 (C=O) | colourless crystals |
| 25 | N1 | B17 | C1 | From N1-B6-C1, acetic acid, TBTU, HOBt and NEt$_3$ in THF | 100 | FM Q | 0.56 | EI: M$^+$ = 633/635/637 (Br$_2$); ESI: (M − H)$^-$ = 632/634/636 (Br$_2$); (M + Na)$^+$ = 656/658/660 (Br$_2$) | 3327 (NH, NH$_2$); 1662 (C=O) | colourless crystals |
| 26 | N1 | B10 | C4 | from N1-B6-C4*CF$_3$CO$_2$H, [1,4']bipiperidinyl-1'-acetic acid, TBTU, HOBt and NEt$_3$ in THF | 52 | FM G FM Q | 0.38 0.37 | ESI: (M + H)$^+$ = 712/714/716 (Cl$_2$); | | colourless crystals |
| 27 | N1 | B14 | C4 | from N1-B6-C4*CF$_3$CO$_2$H, 4-(4-methyl-1-piperazinyl)-1-piperidinoacetic acid, TBTU, HOBt and NEt$_3$ in THF | 16 | FM G FM Q | 0.27 0.26 | ESI: (M − H)$^-$ = 725/727/729 (Cl$_2$); | | colourless crystals |
| 30 | N1 | B25 | C1 | From N1-B24-C1*CF3CO2H, [1,4']bipiperidinyl-1'-acetic acid, TBTU, HOBt and NEt$_3$ in THF | 57 | FM G | 0.38 | ESI: (M − H)$^-$ = 812/814/816 (Br$_2$); (M + H)$^+$ = 814/816/818 (Br$_2$) | 3444, 3344 (NH, NH$_2$); 1664 (C=O) | Colourless Amorphous substance |
| 31 | N1 | B26 | C1 | From N1-B6-C1*CF3CO2H, phenoxyacetic acid, TBTU and NEt$_3$ in THF | 46 | FM G | 0.38 | ESI: (M − H)$^-$ = 724/726/728 (Br$_2$); (M + Na)$^+$ = 748/750/752 (Br$_2$) | 3460, 3329 (NH, NH$_2$); 1660 (C=O) | colourless crystals |
| 32 | N1 | B27 | C1 | From N1-B6-C1*CF3CO2H, 4-chlorophenoxy-acetic acid, TBTU and NEt$_3$ in DMF/THF(1/2) | 32 | FM G | 0.55 | ESI: (M − H)$^-$ = 758/760/762 (Br$_2$); (M + Na)$^+$ = 782/784/786 (Br$_2$) | 3421, 3329 (NH, NH$_2$); 1660 (C=O) | Colourless Amorphous substance |
| 33 | N1 | B28 | C1 | From N1-B6-C1*CF3CO2H, 4-hydroxyphenoxy-acetic acid, TBTU and NEt$_3$ in THF | 38 | FM G | 0.51 | ESI: (M − H)$^-$ = 740/742/744 (Br$_2$); (M + Na)$^+$ = 764/766/768 (Br$_2$) | 3446, 3344, 3072 (OH, NH, NH$_2$); 1653 (C=O) | Colourless Amorphous substance |
| 34 | N1 | B29 | C1 | From N1-B6-C1*CF3CO2H, 4-bromophenoxy-acetic acid, TBTU and NEt$_3$ in DMF/THF (1/2) | 51 | FM G | 0.53 | ESI: (M − H)$^-$ = 802/804/806 (Br$_2$); (M + Na)$^+$ = 826/828/830/832 (Br$_3$) | 3329 (NH, NH$_2$); 1659 (C=O) | Colourless Amorphous substance |
| 35 | N1 | B30 | C1 | From N1-B6-C1*CF3CO2H, 4-cyanophenoxy-acetic acid, TBTU and NEt$_3$ in DMF/THF (1/2) | 44 | FM G | 0.53 | ESI: (M − H)$^-$ = 749/751/753 (Br$_2$); (M + Na)$^+$ = 773/775/777 (Br$_2$) | 3481, 3323 (NH, NH$_2$); 2216 (ar. CN); 1684, 1655 (C=O) | Colourless Amorphous substance |
| 36 | N1 | B31 | C1 | From N1-B6-C1*CF3CO2H, | 55 | FM G | 0.52 | ESI: (M − H)$^-$ = 734/736/738 | 3394, 3278 (NH, NH$_2$); | Colourless amorphous |

| Item no. | N | B | C | Remarks | % yield | FM | $R_f$ | MS | IR [cm$^{-1}$] | Mp. [° C.] |
|---|---|---|---|---|---|---|---|---|---|---|
| | | | | benzo[b]furan-2-carboxylic acid, TBTU and NEt$_3$ in THF/DMF(2/1) | | | | (Br$_2$); (M + Na)$^+$ = 758/760/762 (Br$_2$) | 1676, 1660 (C=O) | substance |
| 38 | N1 | B33 | C1 | From N1-B6-C1* CF3CO2H, 1 H-indole-2-carboxylic acid, TBTU and NEt$_3$ in DMF | 40 | FM G | 0.55 | ESI: (M − H)$^-$ = 733/735/737 (Br$_2$); (M + Na)$^+$ = 757/759/761 (Br$_2$) | 3377, 3331 (NH, NH$_2$); 1660 (C=O) | Colourless Amorphous substance |
| 39 | N1 | B34 | C1 | From N1-B6-C1* CF3CO2H, N-phenylglycine, TBTU and NEt$_3$ in DMF | 31 | FM G | 0.55 | ESI: (M − H)$^-$ = 723/725/727 (Br$_2$); (M + Na)$^+$ = 747/749/751 (Br$_2$) | 3377 (NH, NH$_2$); 1653 (C=O) | colourless amorphous substance |
| 40 | N1 | B35 | C1 | From N1-B6-C1* CF3CO2H, N-phenylsarcosine, TBTU and NEt$_3$ in DMF | 69 | FM G | 0.55 | ESI: (M − H)$^-$ = 737/739/741 (Br$_2$); (M + Na)$^+$ = 761/763/765 (Br$_2$) | 3440, 3321 (NH, NH$_2$); 1659, 1630 (C=O) | colourless amorphous substance |
| 41 | N1 | B36 | C1 | From N1-B6-C1* CF3CO2H, N-4-chlorophenyl-sarcosine, TBTU and NEt$_3$ in DMF | 36 | FM G | 0.55 | ESI: (M − H)$^-$ = 773/775; (M + Na)$^+$ = 795/797/799/801 (ClBr$_2$) | 3331 (NH, NH$_2$); 1653 (C=O) | colourless amorphous substance |
| 44 | N1 | B40 | C1 | From N1-B6-C1* CF3CO2H, 2-pyridineacetic acid, TBTU and NEt$_3$ in DMF | 44 | FM G | 0.53 | ESI: (M − H)$^-$ = 709/711/713 (Br$_2$); (M + H)$^+$ = 711/713/715 (Br$_2$); (M + Na)$^+$ = 733/735/737 (Br$_2$) | 3326 (NH, NH$_2$); 1657 (C=O) | colourless amorphous substance |
| 51 | N1 | B47 | C1 | From N1-B6-C1* CF3CO2H, benzenepropanoic acid, TBTU and NEt$_3$ in DMF | 90 | FM G | 0.55 | ESI: (M − H)$^-$ = 724; (M + Na)$^+$ = 746/748/750 (Br$_2$) | 3327 (NH, NH$_2$); 1660 (C=O) | colourless amorphous substance |
| 56 | N1 | B53 | C1 | From N1-B6-C1* CF3CO2H, 4-(4-methyl-1-piperazinyl)-benzoic acid, TBTU and NEt$_3$ in DMF | 59 | FM G | 0.38 | ESI: (M − H)$^-$ = 792/794/796 (Br$_2$); (M + H)$^+$ = 794/796/798 (Br$_2$) | 3452, 3329 (NH, NH$_2$); 1653 (C=O) | colourless amorphous substance |
| 57 | N1 | B54 | C1 | From N1-B6-C1* CF3CO2H, 4-[4-(phenylmethyl)-1-piperazinyl]-benzoic acid, TBTU and NEt$_3$ in DMF | 26 | FM G | 0.55 | ESI: (M + H)$^+$ = 870/872/874 (Br$_2$); (M + Na)$^+$ = 892/894/896 (Br$_2$) | | Colourless amorphous substance |
| 58 | N1 | B55 | C1 | from N1-B6-C1*CF$_3$CO$_2$H, (R,S)-N$^2$-(1,1-dimethyl-ethoxycarbonyl)-N$^6$-(phenylmethoxy-carbonyl)-norleucine, TBTU, HOBt and NEt$_3$ in THF | 93 | FM G | 0.39 | | 3329 (NH, NH$_2$); 1707 (C=O) | Colourless amorphous substance |
| 61 | N1 | B58 | C1 | From N1-B56-C1*CF$_3$CO$_2$H, [1,4']bipiperidinyl-1'-acetic acid, TBTU, HOBt and NEt$_3$ in THF | 50 | FM G | 0.28 | ESI: (M − H)$^-$ = 1060/1062/1064 (Br$_2$); (M + H)$^+$ = 1062/1064/1066 (Br$_2$) | | Colourless amorphous substance |
| 65 | N1 | B62 | C1 | from N1-B6-C1*CF$_3$CO$_2$H, (R,S)-3,5-dibromo-N-(1,1- | 72 | FM G | 0.34 | ESI: (M − H)$^-$ = 1013; (M + Na)$^+$ = 1037 | 1653 (C=O) | Colourless amorphous Substance |

| Item no. | N | B | C | Remarks | % yield | FM | $R_f$ | MS | IR [cm$^{-1}$] | Mp. [° C.] |
|---|---|---|---|---|---|---|---|---|---|---|
| | | | | dimethylethoxy-carbonyl)-tyrosine, TBTU, HOBt and NEt$_3$ in THF | | | | | | |
| 67 | N2 | B66 | C5 | From N2-B64-C5*CF$_3$CO$_2$H, [1,4']bipiperidinyl-1'-acetic acid, TBTU and NEt$_3$ in DMF | 28 | FM G | 0.43 | ESI: (M − H)$^−$ = 785/787/789 (Br$_2$); (M + Na)$^+$ = 809/811/813 (Br$_2$) | 1657 (C=O) | Colourless amorphous Substance |
| 68 | N2 | B67 | C5 | From N2-B64-C5*CF$_3$CO$_2$H, 4-(4-pyridinyl)-1-piperazinoacetic acid, TBTU and NEt$_3$ in DMF | 32 | FM G | 0.44 | ESI: (M − H)$^−$ = 780/782/784 (Br$_2$); (M + Na)$^+$ = 804/806/808 (Br$_2$) | 1660 (C=O) | Colourless Amorphous substance |
| 69 | N2 | B68 | C5 | From N2-B64-C5*CF$_3$CO$_2$H, 4-methyl-1-piperazinoacetic acid, TBTU and NEt$_3$ in DMF | 35 | FM D | 0.47 | ESI: (M − H)$^−$ = 717/719/721 (Br$_2$); (M + Na)$^+$ = 741/743/745 (Br$_2$) | 1665 (C=O) | Colourless amorphous substance |

Example 2

(R,S)-2-amino-4-(4-amino-3,5-dibromophenyl)-1-{4-[2(2H)-oxo-1,3,4,5-tetrahydro-1,3-benzodiazepin-3-yl]-1-piperidinyl}-1,4-butanedione-trifluoroacetate (I. No. 18)

50 ml of trifluoroacetic acid were added to the ice-cooled solution of 38.0 g (0.055 mol) of (R,S)-4-(4-amino-3,5-dibromophenyl)-2-[(1,1-dimethylethoxycarbonyl)amino]-1-{4-[2(2H)-oxo-1,3,4,5-tetrahydro-1,3-benzodiazepin-3-yl]-1-piperidinyl}-1,4-butanedione (I. No. 17) in 500 ml of dichloromethane, the mixture was stirred for 6 hours at ambient temperature and for 5 hours at 40° C. and then evaporated down in vacuo. The residue was triturated with diethylether, suction filtered and dried in vacuo. 38.5 g (99% of theory) of colourless crystals were obtained, $R_f$ 0.46 (FM Q) or 0.70 (FM D).

IR (KBr): 1670 (C=O) cm$^{-1}$
ESI-MS: (M+H)$^+$=592/594/596 (Br$_2$).

The following were obtained accordingly:

Example 3

(R,S)-4-(4-amino-3,5-dibromophenyl)-2-{{{[1,4']bipiperidinyl-1'-yl}carbonyl}amino}-1-{(4-[2(2H)-oxo-1,3,4,5-tetrahydro-1,3-benzodiazepin-3-yl]-1-piperidinyl}-1,4-butanedione (I. No. 21)

A tetrahydrofuran solution (50 ml) of 1.0 g (1.414 mmol) of (R,S)-2-amino-4-(4-amino-3,5-dibromophenyl)-1-{4-[2(2H)-oxo-1,3,4,5-tetrahydro-1,3-benzodiazepin-3-yl]-1-piperidinyl}-1,4-butanedione-trifluoroacetate (I. No. 18) and 0.222 ml (1.6 mmol) of triethylamine was added dropwise within 40 minutes to a suspension of 0.249 g (1.52 mmol) of CDT in 50 ml tetrahydrofuran, which was stirred and cooled to −10° C. The reaction mixture was then stirred for 1 hour while being cooled externally with ice and for 30 minutes at ambient temperature and then mixed with 0.239 g (1.420 mmol) of [1,4']bipiperidinyl. The mixture was then refluxed for 6 hours. The reaction mixture was evaporated down in vacuo, the residue was purified by column chromatography using a gradient system comprising dichloromethane, methanol and conc. ammonia. Corresponding fractions were freed from solvent, the residue was

| Item no. | N | B | C | Remarks | % yield | FM | $R_f$ | MS | IR [cm$^{-1}$] | Mp. [° C.] |
|---|---|---|---|---|---|---|---|---|---|---|
| 6 | N2 | B6 | C1 | From N2-B4-C1 and ethanolic HCl | 99 | FM Q | 0.43 | ESI: (M + H)$^+$ = 578/580/582 (Br$_2$) | 1653 (C=O) | Colourless crystals |
| 59 | N1 | B56 | C1 | From N1-B55-C1 and CF$_3$CO$_2$H in CH$_2$Cl$_2$ | 99 | FM G | 0.38 | ESI: (M + H)$^+$ = 854/856/858 (Br$_2$) | 3336 (NH, NH$_2$); 1676 (C=O) | Trifluoro acetate: Colourless amorphous substance |
| 66 | N1 | B63 | C1 | From N1-B62-C1 and CF$_3$CO$_2$H in CH$_2$Cl$_2$ | 79 | FM G | 0.36 | ESI: (M − H)$^−$ = 909/911/913 (Br$_2$) | 3381 (NH, NH$_2$); 1674 (C=O) | Trifluoro-acetate: Colourless amorphous substance | triturated with ether and the solid obtained (0.41 g; 37% of theory) was suction filtered and dried.

$R_f$=0.48 (FM Q)
IR (KBr): 1676 cm$^{-1}$ (C=O)
ESI-MS: (M+H)$^+$=786/788/790 (Br$_2$).
The following were prepared analogously:

| Item no. | N | B | C | Remarks | % yield | FM | $R_f$ | MS | IR [cm$^{-1}$] | Mp. [° C.] |
|---|---|---|---|---|---|---|---|---|---|---|
| 20 | N1 | B11 | C1 | From N1-B6-C1* CF$_3$CO$_2$H, CDT, 4-(4-methyl-1-piperazinyl)-piperidine and NEt$_3$ in THF | 35 | FM Q | 0.36 | ESI: (M + H)$^+$ = 801/803/805 (Br$_2$) | 1660 (C=O) | colourless crystals |
| 37 | N1 | B32 | C1 | from N1-B6-C1* CF3CO2H, N,N'-carbonyldiazole and NEt$_3$ in THF at RT | 76 | FM G | 0.36 | (M + Na)$^+$ = 709/711/713 (Br$_2$) | 3329 (NH, NH$_2$); 1732, 1637 (C=O) | Colourless Amorphous substance |
| 43 | N1 | B39 | C1 | from N1-B6-C1* CF3CO2H, N,N'-carbonyldiazole, 2-pyridinamine and NEt$_3$ in THF | 38 | FM G | 0.48 | ESI: (M − H)$^-$ = 710/712/714 (Br$_2$); (M + Na)$^+$ = 734/736/738 (Br$_2$) | 3460, 3329 (NH, NH$_2$); 1659 (C=O) | Colourless Amorphous substance |

Example 4

(R,S)-4-(4-amino-3,5-dibromophenyl)-2-{{[(1-methyl-4-piperidinyl)oxy]carbonyl}amino}-1-{4-[2(2H)-oxo-1,3,4,5-tetrahydro-1,3-benzodiazepin-3-yl]-1-piperidinyl}-1,4-butanedione (I. No. 24)

2.657 ml (0.022 mol) of diphosgene was added dropwise to the suspension of 2.4 g (0.016 Mol) of 1-methyl-4-piperidinol-hydrochloride in 20 ml of acetonitrile, whilst cooling eternally with ice water, the resulting mixture was stirred for 30 minutes at a reaction temperature of 0° C. and overnight at room temperature, whereupon a clear solution was formed which was freed from solvent in vacuo. The residue was triturated with diethylether, suction filtered and dried. This product was added to the mixture of 0.8 g (1.131 mmol) of (R,S)-2-amino-4-(4-amino-3,5-dibromophenyl)-1-{4-[2(2H)-oxo-1,3,4,5-tetrahydro-1,3-benzodiazepin-3-yl]-1-piperidinyl}-1,4-butanedione-trifluoroacetate (I. No. 18), 0.175 ml DIEA and 100 ml THF and it was stirred at room temperature until a clear solution had formed. The solvent was eliminated and the residue was added to a mixture of 10 ml of conc. ammonia and 100 ml of water. It was extracted exhaustively with diethylether, the combined ether extracts were dried over sodium sulphate and evaporated down. 0.10 g (12% of theory) of colourless crystals were obtained, $R_f$=0.27 (FM Q)
IR (KBr): 1716, 1655 cm$^{-1}$ (C=O)
ESI-MS: (M−H)$^-$=731/733/735 (Br$_2$); (M+H)$^+$=733/735/737 (Br$_2$).

Example 5

(R,S)-4-(4-amino-3,5-dibromophenyl)-2-{[1,4']bipiperidinyl-1'-yl}-1-{4-[2(2H)-oxo-1,3,4,5-tetrahydro-1,3-benzodiazepin-3-yl]-1-piperidinyl}-1,4-butanedione (I. No. 28)

246.6 mg (1.244 mmol) of N,N'-sulphonyldiimidazole were added to the mixture of 800 mg (1.131 mmol) of (R,S)-2-amino-4-(4-amino-3,5-dibromophenyl)-1-{4-[2 (2H)-oxo-1,3,4,5-tetrahydro-1,3-benzodiazepin-3-yl]-1-piperidinyl}-1,4-butanedione-trifluoroacetate (I. No. 18), 2.0 ml triethylamine and 40 ml tetrahydrofuran and the mixture was stirred for 2 hours at room temperature and for 5 hours under reflux conditions. After the addition of 211.5 mg (1.131 mmol) of 90% [1,4']bipiperidinyl the mixture was refluxed for another 4 hours, the solvent was eliminated from the mixture and the residue was purified on silica gel using FM G as eluant. After the appropriate fractions had been worked up 420 mg (50% of theory) of a colourless crystalline product (diisopropylether) were obtained, $R_f$ 0.39 (FM G) or 0.40 (FM Q), having the structure given in the title, according to $^1$H-NMR, IR and MS.

IR (KBr): 3464, 3379, 3334 (NH, NH$_2$); 1664, 1643 (C=O) cm$^{-1}$

ESI-MS: (M−H)$^-$=741/743/745 (Br$_2$); (M+H)$^+$=743/745/747 (Br$_2$).

Example 6

(R,S)-4-(4-amino-3,5-dibromophenyl)-2-{{{2-{[1,4']-bipiperidinyl-1'-yl}ethyl}sulphonyl}amino}-1-{4-[2(2H)-oxo-1,3,4,5-tetrahydro-1,3-benzodiazepin-3-yl]-1-piperidinyl}-1,4-butanedione (I. No. 29)

51.98 mg (0.278 mmol) of 90% [1,4']bipiperidinyl were added to the mixture of 200 mg (0.278 mmol) of (R,S)-4-(4-amino-3,5-dibromophenyl)-2-(2-chloroethanesulphonylamino)-1-{4-[2 (2H)-oxo-1,3,4,5-tetrahydro-1,3-benzodiazepin-3-yl]-1-piperidinyl}-1,4-butanedione, 0.1 ml of triethylamine and 20 ml of dichloromethane, while maintaining a reaction temperature of not more than +10° C., the mixture was kept overnight at room temperature, freed from solvent in vacuo and the residue was purified on silica gel using FM G as eluant. After the appropriate fractions had been worked up, 57.0 mg (24% of theory) of a colourless, crystalline product (diisopropylether) were obtained, $R_f$ 0.33 (FM G) or 0.35 (FM Q).

IR (KBr): 3462, 3346, 3126 (NH, NH$_2$); 1653 (C=O) cm$^{-1}$

ESI-MS: (M+H)$^+$=850/852/854 (Br$_2$).

The following were obtained analogously:

| Item no. | N | B | C | Remarks | % yield | FM | $R_f$ | MS | IR [cm$^{-1}$] | Mp. [° C.] |
|---|---|---|---|---|---|---|---|---|---|---|
| 42 | N1 | B37 | C1 | From N1-B38-C1, 1-methyl-4-(1-piperazinyl)-piperidine-trihydrochloride-hydrate and NEt$_3$ in CH$_2$Cl$_2$ | 26 | FM G | 0.61 | ESI: (M − Cl)$^-$ = 849/851/853 (Br$_2$); (M + H)$^+$ = 815/817/819 (Br$_2$) | 3427 (NH, NH$_2$); 1649 (C=O) | colourless crystals |
| 45 | N1 | B41 | C1 | From N1-B38-C1, 4-(4-morpholinyl)-piperidine and NEt$_3$ in CH$_2$Cl$_2$ | 22 | FM G | 0.47 | ESI: (M − H)$^-$ = 802; (M + H)$^+$ = 802/804/806 (Br$_2$); (M + Na)$^+$ = 824/826/828 (Br$_2$) | 3460, 3327 (NH, NH$_2$); 1655 (C=O) | colourless crystals |
| 46 | N1 | B42 | C1 | From N1-B38-C1, 4-(4-pyridinyl)-piperazine and NEt$_3$ in CH$_2$Cl$_2$ | 9 | FM G | 0.47 | ESI: (M + H)$^+$ = 795/797/799 (Br$_2$) | 1645 (C=O) | colourless crystals |
| 47 | N1 | B43 | C1 | From N1-B38-C1, 1-methylethyl-4-(4-piperidinyl)-piperazine-tris-(trifluoroacetate) and NEt$_3$ in CH$_2$Cl$_2$ | 9 | FM G | 0.43 | ESI: (M − H)$^-$ = 843; (M + H)$^+$ = 843/845/847 (Br$_2$) | 3329 (NH, NH$_2$); 1647 (C=O) | Colourless amorphous Substance |
| 48 | N1 | B44 | C1 | From N1-B38-C1, hexahydro-1-methyl-4-(4-piperidinyl)-1H-1,4-diazepine and NEt$_3$ in CH$_2$Cl$_2$ | 9 | FM G | 0.34 | ESI: (M − H)$^-$ = 829; (M + H)$^+$ = 829/831/833 (Br$_2$) | 3329 (NH, NH$_2$); 1647 (C=O) | Colourless amorphous substance |
| 49 | N1 | B45 | C1 | From N1-B38-C1, 1-(methylsulphonyl)-4-(4-piperidinyl)-piperazine-bis-(trifluoroacetate) and NEt$_3$ in CH$_2$Cl$_2$ | 34 | FM G | 0.55 | ESI: (M − H)$^-$ = 879; (M + H)$^+$ = 879/881/883 (Br$_2$); (M + Na)$^+$ = 901/903/905 (Br$_2$) | 3334 (NH, NH$_2$); 1653 (C=O) | Colourless amorphous substance |
| 50 | N1 | B46 | C1 | From N1-B38-C1, 1-(3-dimethylamino-propyl)-4-(4-piperidinyl)-piperazine and NEt$_3$ in CH$_2$Cl$_2$ | 18 | FM G | 0.31 | ESI: (M + H)$^+$ = 886/888/890 (Br$_2$) | 3466, 3304 (NH, NH$_2$); 1662, 1637 (C=O) | Colourless amorphous substance |
| 53 | N1 | B50 | C1 | From N1-B38-C1, 1-methyl-4-[4-(methylamino)-1-piperidinyl]-piperidine and NEt$_3$ in CH$_2$Cl$_2$ | 2.2 | FM G | 0.18 | ESI: (M + H)$^+$ = 843/845/847 (Br$_2$) | 3446, 3331 (NH, NH$_2$); 1653(C=O) | Colourless amorphous substance |
| 54 | N1 | B51 | C1 | From N1-B38-C1, 4-(1-piperidinyl-methyl)piperidine and NEt$_3$ in CH$_2$Cl$_2$ | 30 | FM G | 0.30 | ESI: (M + H)$^+$ = 814/816/818 (Br$_2$) | 3456, 3336 (NH, NH$_2$); 1662 (C=O) | Colourless Amorphous substance |
| 62 | N1 | B59 | C1 | From N1-B22-C1, 4-(1-methyl-4-piperazinyl)-piperidine and NEt$_3$ in CH$_2$Cl$_2$ | 4 | FM G | 0.55 | ESI: (M − H)$^-$ = 863/865/867 (Br$_2$); (M + H)$^+$ = 865/867/869 (Br$_2$) | 3458, 3350 (NH, NH$_2$); 1656 (C=O) | Colourless Amorphous substance |
| 63 | N1 | B60 | C1 | From N1-B22-C1, 1-methyl-4-(1-piperazinyl)-piperidine and NEt$_3$ in CH$_2$Cl$_2$ | 6 | FM G | 0.30 | ESI: (M + H)$^+$ = 865/867/869 (Br$_2$) | 1647 (C=O) | Colourless Amorphous substance |

Example 7

(R,S)-4-(4-amino-3,5-dibromophenyl)-2-{{3-{[1,4']bipiperidinyl-1'-yl}-1-oxopropyl}amino}-1-{4-[2(2H)-oxo-1,3,4,5-tetrahydro-1,3-benzodiazepin-3-yl]-1-piperidinyl}-1,4-butanedione (I. No. 52)

The mixture of 370 mg (0.572 mmol) of (R,S)-4-(4-amino-3,5-dibromophenyl)-2-(1-oxo-2-propen-1-ylamino)-1-{4-[2(2H)-oxo-1,3,4,5-tetrahydro-1,3-benzodiazepin-3-yl]-1-piperidinyl}-1,4-butanedione and 96.256 mg (0.572 mmol) of [1,4']bipiperidinyl in 20 ml dichloromethane was stirred overnight at RT. The mixture was shaken twice with 20 ml of dichloromethane, dried over sodium sulphate and evaporated down in vacuo. The residue was purified by column chromatography on silica gel using FM G as eluant. The colourless amorphous substance obtained after further working up in the usual way was stirred with a little diisopropylether. Yield: 170 mg (36% of theory).

IR (KBr): 1657 (C=O) cm$^{-1}$

ESI: (M+H)$^+$=814/816/818 (Br$_2$).

The following were prepared analogously:

| Item no. | N | B | C | Remarks | % yield | FM | R$_f$ | MS | IR [cm$^{-1}$] | Mp. [° C.] |
|---|---|---|---|---|---|---|---|---|---|---|
| 55 | N1 | B52 | C1 | From N1-B48-C1 and 4-(1-methyl-4-piperazinyl)-piperidine in CH$_2$Cl$_2$ | 13 | | | ESI: (M + H)$^+$ = 829/831/833 (Br$_2$) | 3421 (NH, NH$_2$); 1684 (C=O) | Colourless amorphous-substance |
| 60 | N1 | B57 | C1 | From N1-B48-C1 and 4-(dimethylamino)-piperidine in CH$_2$Cl$_2$ | 7 | FM G | 0.38 | ESI: (M + H)$^+$ = 774/776/778 (Br$_2$) | 3331 (NH, NH$_2$); 1649 (C=O) | Colourless amorphous substance |

Example 8

2-{[6-amino-2-{{{[1,4']bipiperidinyl-1'-yl}-acetyl}amino}-1-oxo-hexyl]amino}-4-(4-amino-3,5-dibromophenyl)-1-{4-[2(2H)-oxo-1,3,4,5-tetrahydro-1,3-benzodiazepin-3-yl]-1-piperidinyl}-1,4-butanedione (I. No. (64))

The mixture of 480 mg (0.451 mmol) of 4-(4-amino-3,5-dibromophenyl)-2-{[2-{{{[1,4']bipiperidinyl-1'-yl}-acetyl}amino}-1-oxo-6-(phenylmethoxycarbonylamino) hexyl]amino}-1-{4-[2(2H)-oxo-1,3,4,5-tetrahydro-1,3-benzodiazepin-3-yl]-1-piperidinyl}-1,4-butanedione, 25 ml of glacial acetic acid, 10 ml of 48% hydrobromic acid in glacial acetic acid and 0.9 ml of anisole was stirred overnight at RT. The mixture was carefully neutralised, first with 5% sodium hydroxide solution, then with solid sodium hydrogen carbonate, and the greasy product precipitated was taken up in methanol, the solution formed was evaporated down in vacuo, the residue was taken up in diisopropyl ether and the product obtained was purified on silica gel using dichloromethane/methanol/conc. ammonia (80/20/1) as eluant. After further working up of the eluates in the usual way, 200 mg (48% of theory) of a colourless amorphous product were obtained, Rf 0.14 (FM dichloromethane/methanol/conc. ammonia (80/20/1)).

IR (KBr): 3437 (NH, NH$_2$); 1641 (C=O) cm$^{-1}$

ESI: (M+H)$^+$=928/930/932 (Br$_2$); (M+Na)$^+$=950/952/954 (Br$_2$).

The Examples which follow illustrate the preparation of some pharmaceutical formulations which contain any desired compound of general formula I as active ingredient:

Example I

Capsules for Powder Inhalation Containing 1 mg of Active Ingredient

Composition:

1 capsule for powder inhalation contains:

| | |
|---|---|
| active ingredient | 1.0 mg |
| lactose | 20.0 mg |
| hard gelatine capsules | 50.0 mg |
| | 71.0 mg |

Method of Preparation:

The active ingredient is ground to the particle size required for inhaled substances. The ground active ingredient is homogeneously mixed with the lactose. The mixture is transferred into hard gelatine capsules.

Example II

Inhalable Solution for Respimat® Containing 1 mg of Active Ingredient

Composition:

1 puff contains:

| | |
|---|---|
| active ingredient | 1.0 mg |
| benzalkonium chloride | 0.002 mg |
| disodium edetate | 0.0075 mg |
| purified water ad | 15.0 μl |

Method of Preparation:

The active ingredient and benzalkonium chloride are dissolved in water and transferred into Respimat® cartridges.

Example III

Inhalable Solution for Nebulisers Containing 1 mg of Active Ingredient

Composition:

1 vial contains:

| | |
|---|---|
| active ingredient | 0.1 g |
| sodium chloride | 0.18 g |
| benzalkonium chloride | 0.002 g |
| purified water ad | 20.0 ml |

Method of Preparation:

The active ingredient, sodium chloride and benzalkonium chloride are dissolved in water.

Example IV

Propellent Gas-operated Metering Aerosol Containing 1 mg of Active Ingredient

Composition:

1 puff contains:

| | |
|---|---|
| active ingredient | 1.0 mg |
| lecithin | 0.1% |
| propellent gas ad | 50.0 μl |

Method of Preparation:

The micronised active ingredient is homogeneously suspended in the mixture of lecithin and propellent gas. The suspension is transferred into a pressurised contained with a metering valve.

Example V
Nasal Spray Containing 1 mg of Active Ingredient
Composition:

| | |
|---|---|
| active ingredient | 1.0 mg |
| sodium chloride | 0.9 mg |
| benzalkonium chloride | 0.025 mg |
| disodium edetate | 0.05 mg |
| purified water ad | 0.1 ml |

Method of Preparation:
The active ingredient and the excipients are dissolved in water and transferred into a suitable container.

Example VI
Injectable Solution Containing 5 mg of Active Substance per 5 ml
Composition:

| | |
|---|---|
| active substance | 5 mg |
| glucose | 250 mg |
| human serum albumin | 10 mg |
| glycofurol | 250 mg |
| water for injections ad | 5 ml |

Preparation:
Glycofurol and glucose are dissolved in water for injections (WfI); human serum albumin is added; active ingredient is dissolved with heating; made up to specified volume with WfI; transferred into ampoules under nitrogen gas.

Example VII
Injectable Solution Containing 100 mg of Active Substance per 20 ml
Composition:

| | |
|---|---|
| active substance | 100 mg |
| monopotassium dihydrogen phosphate = $KH_2PO_4$ | 12 mg |
| disodium hydrogen phosphate = $Na_2HPO_4.2H_2O$ | 2 mg |
| sodium chloride | 180 mg |
| human serum albumin | 50 mg |
| Polysorbate 80 | 20 mg |
| water for injections ad | 20 ml |

Preparation:
Polysorbate 80, sodium chloride, monopotassium dihydrogen phosphate and disodium hydrogen phosphate are dissolved in water for injections (WfI); human serum albumin is added; active ingredient is dissolved with heating; made up to specified volume with WfI; transferred into ampoules.

Example VIII
Lyophilisate Containing 10 mg of Active Substance
Composition:

| | |
|---|---|
| Active substance | 10 mg |
| Mannitol | 300 mg |
| human serum albumin | 20 mg |

Preparation:
Mannitol is dissolved in water for injections (WfI); human serum albumin is added; active ingredient is dissolved with heating; made up to specified volume with WfI; transferred into vials; freeze-dried.
Solvent for Lyophilisate:

| | |
|---|---|
| Polysorbate 80 = Tween 80 | 20 mg |
| mannitol | 200 mg |
| water for injections ad | 10 ml |

Preparation:
Polysorbate 80 and mannitol are dissolved in water for injections (WfI); transferred into ampoules.

Example IX
Tablets Containing 20 mg of Active Substance
Composition:

| | |
|---|---|
| active substance | 20 mg |
| lactose | 120 mg |
| maize starch | 40 mg |
| magnesium stearate | 2 mg |
| Povidon K 25 | 18 mg |

Preparation:
Active substance, lactose and maize starch are homogeneously mixed; granulated with an aqueous solution of Povidone; mixed with magnesium stearate; compressed in a tablet press; weight of tablet 200 mg.

Example X
Capsules Containing 20 mg Active Substance
Composition:

| | |
|---|---|
| active substance | 20 mg |
| maize starch | 80 mg |
| highly dispersed silica | 5 mg |
| magnesium stearate | 2.5 mg |

Preparation:
Active substance, maize starch and silica are homogeneously mixed; mixed with magnesium stearate; the mixture is packed into size 3 hard gelatine capsules in a capsule filling machine.

Example XI
Suppositories Containing 50 mg of Active Substance
Composition:

| | |
|---|---|
| active substance | 50 mg |
| hard fat (Adeps solidus) q.s. ad | 1700 mg |

Preparation:
Hard fat is melted at about 38° C.; ground active substance is homogeneously dispersed in the molten hard fat; after cooling to about 35° C. it is poured into chilled moulds.

Example XII
Injectable Solution Containing 10 mg of Active Substance per 1 ml
Composition:

| active substance | 10 mg |
|---|---|
| mannitol | 50 mg |
| human serum albumin | 10 mg |
| water for injections ad | 1 ml |

Preparation:

Mannitol is dissolved in water for injections (WfI); human serum albumin is added; active ingredient is dissolved with heating; made up to specified volume with WfI; transferred into ampoules under nitrogen gas.

What is claimed is:

1. A compound of the formula

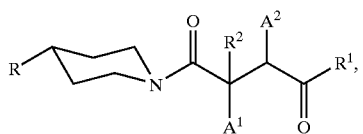

wherein

R denotes a saturated, mono- or di-unsaturated 5- to 7-membered aza, diaza, triaza, oxaza, thiaza, thiadiaza or S,S-dioxido-thiadiaza heterocyclic group, whilst the abovementioned heterocyclic groups are linked via a carbon or nitrogen atom and contain one or two carbonyl groups adjacent to a nitrogen atom, may be substituted by an alkyl group at one of the nitrogen atoms, may be substituted at one or two carbon atoms by an alkyl group, by a phenyl, phenylmethyl, naphthyl, biphenylyl, pyridinyl, diazinyl, furyl, thienyl, pyrrolyl, 1,3-oxazolyl, 1,3-thiazolyl, isoxazolyl, pyrazolyl, 1-methylpyrazolyl, imidazolyl or 1-methylimidazolyl groups, whilst the substituents may be identical or different, and wherein a double bond of one of the above-mentioned unsaturated heterocyclic groups may be fused with a benzene, pyridine, diazine, 1,3-oxazole, thiophene, furan, thiazole, pyrrole, N-methyl-pyrrole or quinoline ring, with a 2(1H)-oxoquinoline ring optionally substituted at the nitrogen atom by an alkyl group or with an imidazole or N-methylimidazole ring or two olefinic double bonds of one of the abovementioned unsaturated heterocyclic groups may each be fused to a benzene ring, whilst the phenyl, pyridinyl, diazinyl, furyl, thienyl, pyrrolyl, 1,3-oxazolyl, 1,3-thiazolyl, isoxazolyl, pyrazolyl, 1-methylpyrazolyl, imidazolyl or 1-methylimidazolyl groups contained in R as well as benzo-, thieno-, pyrido- and diazino-fused heterocyclic groups may additionally be mono-, di- or trisubstituted in the carbon skeleton by fluorine, chlorine or bromine atoms, by alkyl, alkoxy, nitro, alkylthio, alkylsulphinyl, alkylsulphonyl, alkylsulphonylamino, phenyl, trifluoromethyl, alkoxycarbonyl, carboxy, dialkylamino, hydroxy, amino, acetylamino, propionylamino, aminocarbonyl, alkylaminocarbonyl, dialkylaminocarbonyl, (4-morpholinyl)carbonyl, (1-pyrrolidinyl)carbonyl, (1-piperidinyl)carbonyl, (hexahydro-1-azepinyl)carbonyl, (4-methyl-1-piperazinyl)carbonyl, methylenedioxy, aminocarbonylamino, alkanoyl, cyano, trifluoromethoxy, trifluoromethylthio, trifluoromethylsulphinyl or trifluoromethylsulphonyl groups, whilst the substituents may be identical or different, $R^1$ denotes a phenyl, 1-naphthyl, 2-naphthyl, 1H-indol-3-yl, 1-methyl-1H-indol-3-yl, 1-formyl-1H-indol-3-yl, 4-imidazolyl, 1-methyl-4-imidazolyl, 2-thienyl, 3-thienyl, thiazolyl, 1H-indazol-3-yl, 1-methyl-1H-indazol-3-yl, benzo[b]fur-3-yl, benzo[b]thien-3-yl, pyridinyl, quinolinyl or isoquinolinyl group, whilst the abovementioned aromatic and heteroaromatic groups in the carbon skeleton may additionally be mono-, di- or trisubstituted by fluorine, chlorine or bromine atoms, by alkyl groups, cycloalkyl groups with 3 to 8 carbon atoms, phenylalkyl groups, alkenyl, alkoxy, phenyl, phenylalkoxy, trifluoromethyl, alkoxycarbonyl, carboxy, dialkylamino, nitro, hydroxy, amino, alkylamino, acetylamino, propionylamino, methylsulphonyloxy, aminocarbonyl, alkylaminocarbonyl, dialkylaminocarbonyl, alkanoyl, cyano, tetrazolyl, phenyl, pyridinyl, thiazolyl, furyl, trifluoromethoxy, trifluoromethylthio, trifluoromethylsulphinyl or trifluoromethylsulphonyl groups and the substituents may be identical or different, $R^2$ denotes the hydrogen atom or a $C_{1-3}$-alkyl group, one of the groups $A^1$ and $A^2$ denotes the hydrogen atom and the other denotes the amino, the [1,4']bipiperidinyl-1'-yl or an alkylamino group or the group

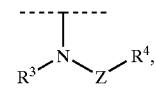

wherein $R^3$ denotes the hydrogen atom or an alkyl group,

Z denotes the carbonyl or the sulphonyl group and $R^4$ denotes an alkoxy, amino, alkylamino or dialkylamino group, a piperidinyl group optionally substituted by a 1-methyl-4-piperidinyl, 4-methyl-1-piperazinyl or piperidinyl group, a 1-methyl-4-piperidinyloxy group, a pyridinylamino, benzo[b]furanyl, 1,2,4-triazol-1-yl or 1H-indolyl group, a phenyl group optionally substituted by a 4-alkyl-1-piperazinyl or 4-arylalkyl-1-piperazinyl group or a branched or unbranched alkyl group comprising 1 to 7 carbon atoms, which may be substituted in the ω position by an amino, phenyl, pyridinyl, phenoxy, phenylamino, phenylmethoxycarbonylamino or N-alkylphenylamino group, by a dialkylamino group, by a piperidinyl or piperazinyl group optionally substituted by a phenyl, pyridinyl, dimethylamino, 4-morpholinyl, 4-alkyl-hexahydro-1H-1,4-diazepin-1-yl, 4-alkyl-1-piperazinyl, 4-(alkylsulphonyl)-1-piperazinyl, 4-(dialkylaminoalkyl)-1-piperazinyl, 1-alkyl-4-piperidinyl or piperidinyl group, by a 4-methyl-1-piperazinyl group, by an N-($C_{1-3}$-alkyl)-N-(1'-$C_{1-3}$-alkyl-[1,4']bipiperidinyl-1-yl)amino or 4-(1-piperidinylmethyl)-1-piperidinyl group and independently thereof in the α position by an amino, tert.alkoxycarbonylamino or {{{[1,4']bipiperidinyl-1'-yl}-acetyl}amino} group, whilst the abovementioned alkyl and alkenyl groups or the alkyl groups contained in the abovementioned groups, unless otherwise specified, contain 1 to 5 carbon atoms and may be branched or unbranched and the abovementioned aromatic and heteroaromatic groups may additionally be mono-, di- or trisubstituted by fluorine, chlorine or bromine atoms, by cyano or hydroxy groups and the substituents may be identical or different, or a tautomer or salt thereof.

2. A compound of the formula I according to claim 1, wherein

R denotes a mono- or di-unsaturated 5- to 7-membered aza, diaza, triaza or thiaza heterocyclic group, whilst the abovementioned heterocyclic groups are linked via a carbon or nitrogen atom and contain one or two carbonyl groups adjacent to a nitrogen atom, may be substituted at a carbon atom by a phenyl, pyridinyl, diazinyl, thienyl, pyrrolyl, 1,3-thiazolyl, isoxazolyl, pyrazolyl or 1-methylpyrazolyl group, and wherein an olefinic double bond of one of the abovementioned unsaturated heterocyclic groups may be fused to a benzene, pyridine, diazine or quinoline ring or to a 2(1H)-oxoquinoline ring optionally substituted at the nitrogen atom by a methyl group, or two olefinic double bonds of one of the abovementioned unsaturated heterocyclic groups may each be fused to a benzene ring, whilst the phenyl, pyridinyl, diazinyl, thienyl, pyrrolyl, 1,3-thiazolyl, isoxazolyl, pyrazolyl or 1-methylpyrazolyl groups contained in R as well as benzo-, pyrido- and diazino-fused heterocyclic groups may additionally be mono-, di- or trisubstituted in the carbon skeleton by fluorine, chlorine or bromine atoms, by alkyl, alkoxy, nitro, trifluoromethyl, hydroxy, amino, acetylamino, acetyl, cyano or trifluoromethoxy groups, whilst the substituents may be identical or different, $R^1$ denotes a phenyl, 1-naphthyl or 2-naphthyl group, whilst these aromatic groups may be mono-, di- or trisubstituted by fluorine, chlorine or bromine atoms, by branched or unbranched alkyl groups, by alkoxy, trifluoromethyl, nitro, hydroxy, amino or acetylamino groups, whilst the substituents may be identical or different, $R^2$ denotes the hydrogen atom or the methyl group, one of the groups $A^1$ and $A^2$ denotes the hydrogen atom and the other denotes the amino, methylamino or ethylamino group, the [1,4']bipiperidinyl-1'-yl group or the group

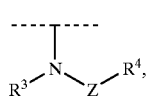 (II)

wherein $R^3$ denotes the hydrogen atom, the methyl or the ethyl group,

Z denotes the carbonyl or sulphonyl group and $R^4$ denotes an alkoxy, amino, alkylamino or dialkylamino group, a 1- or 4-piperidinyl group optionally substituted by a 1-methyl-4-piperidinyl, 4-methyl-1-piperazinyl or 1-piperidinyl group, a 1-methyl-4-piperidinyloxy group, a pyridinylamino, benzo[b]furanyl, 1,2,4-triazol-1-yl or 1H-indolyl group, a phenyl group optionally substituted by a 4-methyl-1-piperazinyl or 4-phenylmethyl-1-piperazinyl group, or a branched or unbranched alkyl group comprising 1 to 7 carbon atoms which may be substituted in the ω position by an amino, phenyl, pyridinyl, phenoxy, phenylamino, phenylmethoxycarbonylamino or N-methylphenylamino group, by a dimethylamino group, by a 1-piperidinyl or 1-piperazinyl group optionally substituted by a phenyl, pyridinyl, dimethylamino, 4-morpholinyl, 4-methyl-hexahydro-1H-1,4-diazepin-1-yl, 4-methyl-1-piperazinyl, 4-(methylsulphonyl)-1-piperazinyl, 4-(dimethylamino-alkyl)-1-piperazinyl, 1-methyl-4-piperidinyl or 1-piperidinyl group, by a 4-methyl-1-piperazinyl group, by a N-methyl-N-(1'-methyl-[1,4']bipiperidinyl-1-yl)amino or 4-(1-piperidinylmethyl)-1-piperidinyl group and independently thereof in the α position by an amino, tert.butoxycarbonylamino or {{{[1,4']bipiperidinyl-1'-yl}-acetyl}amino} group, whilst the abovementioned alkyl groups or the alkyl groups contained in the abovementioned groups, unless otherwise specified, contain 1 to 4 carbon atoms and may be branched or unbranched and the abovementioned aromatic and heteroaromatic groups may additionally be mono-, di- or trisubstituted by fluorine, chlorine or bromine atoms, by cyano or hydroxy groups and the substituents may be identical or different, or tautomer or salt thereof.

3. A compounds of the formula I according to claim 1, wherein

R denotes a mono-unsaturated 5- to 7-membered diaza or triaza heterocyclic group, whilst the abovementioned heterocyclic groups are linked via a nitrogen atom, contain a carbonyl group adjacent to a nitrogen atom and may additionally be substituted at a carbon atom by a phenyl group, and wherein an olefinic double bond of one of the abovementioned unsaturated heterocyclic groups may be substituted by a benzene or quinoline ring or by a 2(1H)-oxoquinoline ring optionally substituted at the nitrogen atom by a methyl group, or two olefinic double bonds of one of the abovementioned unsaturated heterocyclic groups may each be fused to a benzene ring, whilst the phenyl groups contained in R as well as benzo-fused heterocyclic may additionally be mono-, di- or trisubstituted groups in the carbon skeleton by fluorine, chlorine or bromine atoms, by methyl, methoxy, nitro, trifluoromethyl, hydroxy, amino, acetylamino, acetyl, cyano or trifluoromethoxy groups, whilst the substituents may be identical or different, and are preferably unsubstituted or monosubstituted by a fluorine, chlorine or bromine atom or by a methyl or methoxy group, $R^1$ denotes a phenyl group optionally mono-, di- or trisubstituted by fluorine, chlorine or bromine atoms, by methyl, methoxy, trifluoromethyl, nitro, hydroxy or amino groups, whilst the substituents may be identical or different, $R^2$ denotes the hydrogen atom or the methyl group and one of the groups $A^1$ and $A^2$ denotes the hydrogen atom and the other denotes the amino or methylamino group, the [1,4']bipiperidinyl-1'-yl group or the group

(II)

wherein $R^3$ denotes the hydrogen atom or the methyl group,

Z denotes the carbonyl or sulphonyl group and $R^4$ denotes a branched or unbranched $C_{1-5}$-alkoxy group, a 1- or 4-piperidinyl group optionally substituted by a 1-methyl-4-piperidinyl, 4-methyl-1-piperazinyl or 1-piperidinyl group, a 1-methyl-4-piperidinyloxy group, a 2-pyridinylamino, benzo[b]furan-2-yl, 1,2,4-triazol-1-yl or 1H-indol-2-yl group, a phenyl group optionally substituted by a 4-methyl-1-piperazinyl or 4-phenylmethyl-1-piperazinyl group or a branched or unbranched alkyl group comprising 1 to 7 carbon atoms which is substituted in the ω position by an amino, phenyl, 2-pyridinyl, phenoxy, phenylamino, phenylmethoxycarbonylamino or N-methylphenylamino group, by a dimethylamino group, by a piperidinyl or 1-piperazinyl group optionally substituted by a phenyl, pyridinyl, dimethylamino, 4-morpholinyl, 4-methyl-hexahydro-1H-1,4-diazepin-1-yl, 4-methyl-1-piperazinyl, 4-(methylsulphonyl)-1-piperazinyl, 4-(3-dimethylaminopropyl)-1-piperazinyl, (2-dimethylaminoethyl)-1-piperazinyl, 1-methyl-4-piperidinyl or 1-piperidinyl group, by a 4-methyl-1-piperazinyl group, by a N-methyl-N-(1'-methyl-[1,4'] bipiperidinyl-1-yl)amino or 4-(1-piperidinylmethyl)-1-piperidinyl group or is substituted in the α position by an amino, tert.butoxycarbonylamino or {{{[1,4']bipiperidinyl-1'-yl}-acetyl}amino} group or is substituted in the ω position by an amino, phenyl or phenylmethoxycarbonylamino group and in the α position by an amino, tert.butoxycarbonylamino or {{{[1,4']bipiperidinyl-1'-yl}-acetyl}amino} group, whilst the abovementioned alkyl groups or the alkyl groups contained in the abovementioned groups, unless otherwise specified, contain 1 to 4 carbon atoms and may be branched or unbranched and the abovementioned aromatic and heteroaromatic groups may additionally be mono-, di- or trisubstituted by fluorine, chlorine or bromine atoms, by cyano or hydroxy groups, or a tautomer or salt thereof.

4. A compounds of the formula I according to claim 1, wherein

R denotes a 3,4-dihydro-2(1H)-oxoquinazolin-3-yl, 1,3-dihydro-4-phenyl-2H-2-oxoimidazol-1-yl, 2,4-dihydro-5-phenyl-3(3H)-oxo-1,2,4-triazol-2-yl, 1,3-dihydro-2(2H)-oxoimidazo[4,5-c]quinolin-3-yl, 1,3,4,5-tetrahydro-2-oxo-1,3-benzodiazepin-3-yl, 1,3-dihydro-5-methyl-2,4(2H,5H)-dioxoimidazo[4,5-c]quinolin-3-yl, 5,7-dihydro-6-oxo-1,3-dibenzodiazepin-5-yl or 1,3-dihydro-2-oxobenzimidazol-1-yl group, whilst the abovementioned bicyclic heterocyclic groups may additionally be monosubstituted in the carbon skeleton by methoxy groups, $R^1$ denotes a phenyl group optionally mono-, di- or trisubstituted by fluorine, chlorine or bromine atoms or by hydroxy or amino groups, whilst the substituents may be identical or different, $R^2$ denotes the hydrogen atom or the methyl group one of the groups $A^1$ and $A^2$ denotes the hydrogen atom and the other denotes the amino or methylamino group, the [1,4']-bipiperidinyl-1'-yl group or the group

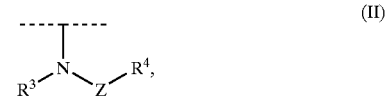

(II)

wherein $R^3$ denotes the hydrogen atom or the methyl group,

Z denotes the carbonyl or sulphonyl group and $R^4$ denotes a branched or unbranched $C_{1-4}$-alkoxy group, a 1- or 4-piperidinyl group optionally substituted by a 1-methyl-4-piperidinyl, 4-methyl-1-piperazinyl or 1-piperidinyl group, a 1-methyl-4-piperidinyloxy group, a 2-pyridinylamino, benzo[b]furan-2-yl, 1,2,4-triazol-1-yl or 1H-indol-2-yl group, a phenyl group optionally substituted by a 4-methyl-1-piperazinyl or 4-phenylmethyl-1-piperazinyl group, or a branched or unbranched alkyl group having 1 to 7 carbon atoms, preferably 1 to 5 carbon atoms, which is substituted in the ω position by an amino, 2-pyridinyl, phenoxy, phenylamino, phenylmethoxycarbonylamino or N-methylphenylamino group, by a dimethylamino group, by a 1-piperidinyl or 1-piperazinyl group optionally substituted by a phenyl, 4-pyridinyl, dimethylamino, 4-morpholinyl, 4-methyl-hexahydro-1H-1,4-diazepin-1-yl, 4-methyl-1-piperazinyl, 4-(methylsulphonyl)-1-piperazinyl, 4-(3-dimethylaminopropyl)-1-piperazinyl, 1-methyl-4-piperidinyl or 1-piperidinyl group, by a 4-methyl-1-piperazinyl group, by an N-methyl-N-(11-methyl-[1,4'] bipiperidinyl-1-yl)amino or 4-(1-piperidinylmethyl)-1-piperidinyl group or is substituted in the ω position by an amino, phenyl or phenylmethoxycarbonylamino group and in the α position by an amino, tert.butoxycarbonylamino or {{{[1,4']-bipiperidinyl-1'-yl}-acetyl}amino} group, whilst the abovementioned alkyl groups or the alkyl groups contained in the abovementioned groups, unless otherwise specified, contain 1 to 4 carbon atoms and may be branched or unbranched and the abovementioned aromatic and heteroaromatic groups may additionally be mono-, di- or trisubstituted by fluorine, chlorine or bromine atoms, by cyano or hydroxy groups, or a tautomer or salt thereof.

5. A compounds selected from the group consisting of:

(1) (R,S)-4-(4-amino-3,5-dibromophenyl)-2-[(1,1-dimethylethoxycarbonyl)methylamino]-1-{4-[2(2H)-oxo-1,3,4,5-tetrahydro-1,3-benzodiazepin-3-yl]-1-piperidinyl}-1,4-butanedione;

(2) (R,S)-4-(4-amino-3,5-dibromophenyl)-2-{{{[1,4']-bipiperidinyl-1'-yl}acetyl}methylamino}-1-{4-[2(2H)-oxo-1,3,4,5-tetrahydro-1,3-benzodiazepin-3-yl]-1-piperidinyl}-1,4-butanedione;

(3) (R,S)-2-[(acetyl)methylamino]-4-(4-amino-3,5-dibromo-phenyl)-1-{4-[2(2H)-oxo-1,3,4,5-tetrahydro-1,3-benzodiazepin-3-yl]-1-piperidinyl}-1,4-butanedione;

(4) (R,S)-4-(4-amino-3,5-dibromophenyl)-1-{4-[1,4-dihydro-2(2H)-oxoquinazolin-3-yl]-1-piperidinyl}-2-[(1,1-dimethylethoxycarbonyl)amino]-1,4-butanedione;

(5) (R,S)-4-(4-amino-3,5-dibromophenyl)-1-{4-[1,4-dihydro-2(2H)-oxoquinazolin-3-yl]-1-piperidinyl}-2-{[4-(dimethylamino)-1-oxobutyl]amino}-1,4-butanedione;

(6) (R,S)-2-amino-4-(4-amino-3,5-dibromophenyl)-1-{4-[1,4-dihydro-2(2H)-oxoquinazolin-3-yl]-1-piperidinyl}-1,4-butanedione;

(7) (R,S)-4-(4-amino-3,5-dibromophenyl)-1-{4-[1,4-dihydro-2(2H)-oxoquinazolin-3-yl]-1-piperidinyl}-2-{{{1'-methyl-[1,4']bipiperidinyl-4-yl}carbonyl}-amino}-1,4-butanedione;

(8) (R,S)-4-(4-amino-3,5-dibromophenyl)-1-{4-[1,4-dihydro-2(2H)-oxoquinazolin-3-yl]-1-piperidinyl}-2-{[(4-methyl-1-piperazinyl)acetyl]amino}-1,4-butanedione;

(9) (R,S)-4-(4-amino-3,5-dibromophenyl)-1-{4-[5-methyl-2,4-dioxo-2,3,4,5-tetrahydro-1H-imidazo[4,5-c]quinolin-3-yl]-1-piperidinyl}-2-{[(4-methyl-1-piperazinyl)acetyl]amino}-1,4-butanedione;

(10) (R,S)-4-(4-amino-3,5-dibromophenyl)-1-{4-[5,7-dihydro-6(6H)-oxodibenzo[d,f][1,3]diazepin-5-yl]-1-piperidinyl}-2-{[(4-methyl-1-piperazinyl)acetyl]amino}-1,4-butanedione;

(11) (R,S)-4-(4-amino-3,5-dibromophenyl)-1-{4-[1,3-dihydro-2(2H)-oxo-4-phenyl-1-imidazolyl]-1-piperidinyl}-2-{[(4-methyl-1-piperazinyl)acetyl]amino}-1,4-butanedione;

(12) (R,S)-4-(4-amino-3,5-dibromophenyl)-1-{4-[1,3-dihydro-2(2H)-oxo-imidazo[4,5-c]quinolin-3-yl]-1-piperidinyl}-2-{[(4-methyl-1-piperazinyl)acetyl]amino}-1,4-butanedione;

(13) (R,S)-4-(4-amino-3,5-dibromophenyl)-1-{4-[1,4-dihydro-5(5H)-oxo-3-phenyl-[1,2,4]triazole-1-yl]-1-piperidinyl}-2-{[(4-methyl-1-piperazinyl)acetyl]amino}-1,4-butanedione;

(14) (R,S)-4-(4-amino-3,5-dibromophenyl)-1-{4-[7-methoxy-2(2H)-oxo-1,3,4,5-tetrahydro-1,3-benzodiazepin-3-yl]-1-piperidinyl}-2-{[(4-methyl-1-piperazinyl)acetyl]amino}-1,4-butanedione;

(15) (R,S)-4-(4-amino-3,5-dibromophenyl)-2-{[(4-methyl-1-piperazinyl)acetyl]amino}-1-{4-[2(2H)-oxo-1,3,4,5-tetrahydro-1,3-benzodiazepin-3-yl]-1-piperidinyl}-1,4-butanedione;

(16) (R,S)-4-(4-amino-3,5-dibromophenyl)-1-{4-[2(2H)-oxo-1,3-dihydrobenzimidazol-1-yl]-1-piperidinyl}-2-{[(4-methyl-1-piperazinyl)acetyl]amino}-1,4-butanedione;

(17) (R,S)-4-(4-amino-3,5-dibromophenyl)-2-[(1,1-dimethyl-ethoxycarbonyl)amino]-1-{4-[2(2H)-oxo-1,3,4,5-tetrahydro-1,3-benzodiazepin-3-yl]-1-piperidinyl}-1,4-butanedione;

(18) (R,S)-2-amino-4-(4-amino-3,5-dibromophenyl)-1-{4-[2(2H)-oxo-1,3,4,5-tetrahydro-1,3-benzodiazepin-3-yl]-1-piperidinyl}-1,4-butanedione;

(19) (R,S)-4-(4-amino-3,5-dibromophenyl)-2-{{{[1,4']-bipiperidinyl-1'-yl}acetyl}amino}-1-{4-[2(2H)-oxo-1,3,4,5-tetrahydro-1,3-benzodiazepin-3-yl]-1-piperidinyl}-1,4-butanedione;

(20) (R,S)-4-(4-amino-3,5-dibromophenyl)-2-{{[4-(4-methyl-1-piperazinyl)-1-piperidinyl]carbonyl}amino}-1-{4-[2(2H)-oxo-1,3,4,5-tetrahydro-1,3-benzodiazepin-3-yl]-1-piperidinyl}-1,4-butanedione;

(21) (R,S)-4-(4-amino-3,5-dibromophenyl)-2-{{{[1,4']-bipiperidinyl-1'-yl}carbonyl}amino}-1-{4-[2(2H)-oxo-1,3,4,5-tetrahydro-1,3-benzodiazepin-3-yl]-1-piperidinyl}-1,4-butanedione;

(22) (R,S)-4-(4-amino-3,5-dibromophenyl)-2-{{[4-(dimethylamino)-1-piperidinyl]acetyl}amino}-1-{4-[2(2H)-oxo-1,3,4,5-tetrahydro-1,3-benzodiazepin-3-yl]-1-piperidinyl}-1,4-butanedione;

(23) (R,S)-4-(4-amino-3,5-dibromophenyl)-2-{{[4-(4-methyl-1-piperazinyl)-1-piperidinyl]acetyl}amino}-1-{4-[2(2H)-oxo-1,3,4,5-tetrahydro-1,3-benzodiazepin-3-yl]-1-piperidinyl}-1,4-butanedione;

(24) (R,S)-4-(4-amino-3,5-dibromophenyl)-2-{{[(1-methyl-4-piperidinyl)oxy]carbonyl}amino}-1-{4-[2(2H)-oxo-1,3,4,5-tetrahydro-1,3-benzodiazepin-3-yl]-1-piperidinyl}-1,4-butanedione;

(25) (R,S)-2-(acetylamino)-4-(4-amino-3,5-dibromophenyl)-1-{4-[2(2H)-oxo-1,3,4,5-tetrahydro-1,3-benzodiazepin-3-yl]-1-piperidinyl}-1,4-butanedione;

(26) (R,S)-4-(4-amino-3,5-dichlorophenyl)-2-{{{[1,4']-bipiperidinyl-1'-yl}acetyl}amino}-1-{4-[2(2H)-oxo-1,3,4,5-tetrahydro-1,3-benzodiazepin-3-yl]-1-piperidinyl}-1,4-butanedione;

(27) (R,S)-4-(4-amino-3,5-dichlorophenyl)-2-{{[4-(4-methyl-1-piperazinyl)-1-piperidinyl]acetyl}amino}-1-{4-[2(2H)-oxo-1,3,4,5-tetrahydro-1,3-benzodiazepin-3-yl]-1-piperidinyl}-1,4-butanedione;

(28) (R,S)-4-(4-amino-3,5-dibromophenyl)-2-{[1,4']-bipiperidinyl-1'-yl}-1-{4-[2(2H)-oxo-1,3,4,5-tetrahydro-1,3-benzodiazepin-3-yl]-1-piperidinyl}-1,4-butanedione;

(29) (R,S)-4-(4-amino-3,5-dibromophenyl)-2-{{{2-{[1,4']-bipiperidinyl-1'-yl}ethyl}sulphonyl}amino}-1-{4-[2(2H)-oxo-1,3,4,5-tetrahydro-1,3-benzodiazepin-3-yl]-1-piperidinyl}-1,4-butanedione;

(30) (R,S)-4-(4-amino-3,5-dibromophenyl)-2-{{{[1,4']-bipiperidinyl-1'-yl}-acetyl}amino}-2-methyl-1-{4-[2(2H)-oxo-1,3,4,5-tetrahydro-1,3-benzodiazepin-3-yl]-1-piperidinyl}-1,4-butanedione;

(31) (R,S)-4-(4-amino-3,5-dibromophenyl)-1-{4-[2(2H)-oxo-1,3,4,5-tetrahydro-1,3-benzodiazepin-3-yl]-1-piperidinyl}-2-(phenoxyacetylamino)-1,4-butanedione;

(32) (R,S)-4-(4-amino-3,5-dibromophenyl)-2-(4-chlorophenoxy-acetylamino)-1-{4-[2(2H)-oxo-1,3,4,5-tetrahydro-1,3-benzodiazepin-3-yl]-1-piperidinyl}-1,4-butanedione;

(33) (R,S)-4-(4-amino-3,5-dibromophenyl)-2-(4-hydroxyphenoxy-acetylamino)-1-{4-[2(2H)-oxo-1,3,4,5-tetrahydro-1,3-benzodiazepin-3-yl]-1-piperidinyl}-1,4-butanedione;

(34) (R,S)-4-(4-amino-3,5-dibromophenyl)-2-(4-bromophenoxy-acetylamino)-1-{4-[2(2H)-oxo-1,3,4,5-tetrahydro-1,3-benzo-diazepin-3-yl]-1-piperidinyl}-1,4-butanedione;

(35) (R,S)-4-(4-amino-3,5-dibromophenyl)-2-(4-cyanophenoxy-acetylamino)-1-{4-[2(2H)-oxo-1,3,4,5-tetrahydro-1,3-benzodiazepin-3-yl]-1-piperidinyl}-1,4-butanedione;

(36) (R,S)-4-(4-amino-3,5-dibromophenyl)-2-(benzo[b]furan-2-carbonylamino)-1-{4-[2(2H)-oxo-1,3,4,5-tetrahydro-1,3-benzo-diazepin-3-yl]-1-piperidinyl}-1,4-butanedione;

(37) (R,S)-4-(4-amino-3,5-dibromophenyl)-2-(1,2,4-triazole-1-carbonylamino)-1-{4-[2(2H)-oxo-1,3,4,5- tetrahydro-1,3-benzo-diazepin-3-yl]-1-piperidinyl}-1,4-butanedione;

(38) (R,S)-4-(4-amino-3,5-dibromophenyl)-2-(1H-indole-2-carbonyl-amino)-1-{4-[2(2H)-oxo-1,3,4,5-tetrahydro-1,3-benzodiazepin-3-yl]-1-piperidinyl}-1,4-butanedione;

(39) (R,S)-4-(4-amino-3,5-dibromophenyl)-2-(phenylaminoacetyl-amino)-1-{4-[2(2H)-oxo-1,3,4,5-tetrahydro-1,3-benzodiazepin-3-yl]-1-piperidinyl}-1,4-butanedione;

(40) (R,S)-4-(4-amino-3,5-dibromophenyl)-2-[(N-methylphenylamino)acetylamino]-1-{4-[2(2H)-oxo-1,3,4,5-tetrahydro-1,3-benzo-diazepin-3-yl]-1-piperidinyl}-1,4-butanedione;

(41) (R,S)-4-(4-amino-3,5-dibromophenyl)-2-[(N-methyl-4-chlorophenylamino)acetylamino]-1-{4-[2(2H)-oxo-1,3,4,5-tetrahydro-1,3-benzodiazepin-3-yl]-1-piperidinyl}-1,4-butanedione;

(42) (R,S)-4-(4-amino-3,5-dibromophenyl)-2-{{[4-(1-methyl-4-piperidinyl)-1-piperazinyl]acetyl}amino}-1-{4-[2(2H)-oxo-1,3,4,5-tetrahydro-1,3-benzodiazepin-3-yl]-1-piperidinyl}-1,4-butanedione;

(43) (R,S)-4-(4-amino-3,5-dibromophenyl)-2-(2-pyridinylacetyl-amino)-1-{4-[2(2H)-oxo-1,3,4,5-tetrahydro-1,3-benzodiazepin-3-yl]-1-piperidinyl}-1,4-butanedione;

(44) (R,S)-4-(4-amino-3,5-dibromophenyl)-2-(2-pyridinylamino-carbonylamino)-1-{4-[2(2H)-oxo-1,3,4,5-tetrahydro-1,3-benzo-diazepin-3-yl]-1-piperidinyl}-1,4-butanedione;

(45) (R,S)-4-(4-amino-3,5-dibromophenyl)-2-{{[4-(4-morpholinyl)-1-piperidinyl]acetyl}amino}-1-4-[2(2H)-oxo-1,3,4,5-tetrahydro-1,3-benzodiazepin-3-yl]-1-piperidinyl)-1,4-butanedione;

(46) (R,S)-4-(4-amino-3,5-dibromophenyl)-2-{{[4-(4-pyridinyl)-1-piperazinyl]acetyl}amino}-1-{4-[2(2H)-oxo-1,3,4,5-tetrahydro-1,3-benzodiazepin-3-yl]-1-piperidinyl}-1,4-butanedione;

(47) (R,S)-4-(4-amino-3,5-dibromophenyl)-2-{{{4-[4-(1-methylethyl)-1-piperazinyl]-1-piperidinyl}acetyl}-amino}-1-{4-[2(2H)-oxo-1,3,4,5-tetrahydro-1,3-benzodiazepin-3-yl]-1-piperidinyl}-1,4-butanedione;

(48) (R,S)-4-(4-amino-3,5-dibromophenyl)-2-{{[4-(hexahydro-4-methyl-1H-1,4-diazepin-1-yl)-1-piperidinyl]acetyl}amino}-1-{4-[2(2H)-oxo-1,3,4,5-tetrahydro-1,3-benzodiazepin-3-yl]-1-piperidinyl}-1,4-butanedione;

(49) (R,S)-4-(4-amino-3,5-dibromophenyl)-2-{{{4-[4-(methylsulphonyl)-1-piperazinyl]-1-piperidinyl}-acetyl}amino}-1-{4-[2(2H)-oxo-1,3,4,5-tetrahydro-1,3-benzodiazepin-3-yl]-1-piperidinyl}-1,4-butanedione;

(50) (R,S)-4-(4-amino-3,5-dibromophenyl)-2-{{{4-[4-(3-dimethyl-aminopropyl)-1-piperazinyl]-1-piperidinyl}acetyl}amino}-1-{4-[2(2H)-oxo-1,3,4,5-tetrahydro-1,3-benzodiazepin-3-yl]-1-piperidinyl}-1,4-butanedione

(51) (R,S)-4-(4-amino-3,5-dibromophenyl)-2-[(1-oxo-3-phenylpropyl)amino]-1-{4-[2(2H)-oxo-1,3,4,5-tetrahydro-1,3-benzo-diazepin-3-yl]-1-piperidinyl}-1,4-butanedione;

(52) (R,S)-4-(4-amino-3,5-dibromophenyl)-2-{{3-{[1,4']-bipiperidinyl-1'-yl}-1-oxopropyl}amino}-1-{4-[2(2H)-oxo-1,3,4,5-tetrahydro-1,3-benzodiazepin-3-yl]-1-piperidinyl}-1,4-butanedione;

(53) (R,S)-4-(4-amino-3,5-dibromophenyl)-2-{{{N-methyl-N-{1'-methyl-[1,4']bipiperidinyl-4-yl}amino}acetyl}amino}-1-{4-[2(2H)-oxo-1,3,4,5-tetrahydro-1,3-benzodiazepin-3-yl]-1-piperidinyl}-1,4-butanedione;

(54) (R,S)-4-(4-amino-3,5-dibromophenyl)-2-{{[4-(1-piperidinylmethyl)-1-piperidinyl]acetyl}amino}-1-{4-[2(2H)-oxo-1,3,4,5-tetrahydro-1,3-benzodiazepin-3-yl]-1-piperidinyl}-1,4-butanedione;

(55) (R,S)-4-(4-amino-3,5-dibromophenyl)-2-{{3-[4-(4-methyl-1-piperazinyl)-1-piperidinyl]-1-oxopropyl}amino}-1-{4-[2(2H)-oxo-1,3,4,5-tetrahydro-1,3-benzodiazepin-3-yl]-1-piperidinyl)-1,4-butanedione;

(56) (R,S)-4-(4-amino-3,5-dibromophenyl)-2-[4-(4-methyl-1-piperazinyl)benzoylamino]-1-{4-[2(2H)-oxo-1,3,4,5-tetrahydro-1,3-benzodiazepin-3-yl]-1-piperidinyl}-1,4-butanedione;

(57) (R,S)-4-(4-amino-3,5-dibromophenyl)-2-[4-(4-phenylmethyl-1-piperazinyl)benzoylamino]-1-{4-[2(2H)-oxo-1,3,4,5-tetrahydro-1,3-benzodiazepin-3-yl]-1-piperidinyl}-1,4-butanedione;

(58) 4-(4-amino-3,5-dibromophenyl)-2-{[2-(1,1-dimethylethoxy-carbonylamino)-1-oxo-6-(phenylmethoxy-carbonylamino)hexyl]-amino}-1-{4-[2(2H)-oxo-1,3,4,5-tetrahydro-1,3-benzodiazepin-3-yl]-1-piperidinyl}-1,4-butanedione;

(59) 4-(4-amino-3,5-dibromophenyl)-2-{[2-amino-1-oxo-6-(phenylmethoxycarbonylamino)hexyl]amino}-1-{4-[2(2H)-oxo-1,3,4,5-tetrahydro-1,3-benzodiazepin-3-yl]-1-piperidinyl}-1,4-butanedione;

(60) (R,S)-4-(4-amino-3,5-dibromophenyl)-2-{{3-[4-(dimethyl-amino)-1-piperidinyl]-1-oxopropyl}-amino}-1-{4-[2(2H)-oxo-1,3,4,5-tetrahydro-1,3-benzodiazepin-3-yl]-1-piperidinyl}-1,4-butanedione;

(61) 4-(4-amino-3,5-dibromophenyl)-2-{[2-{{{[1,4']bipiperidinyl-1'-yl}-acetyl}amino}-1-oxo-6-(phenylmethoxycarbonylamino)hex-yl]amino}-1-{4-[2(2H)-oxo-1,3,4,5-tetrahydro-1,3-benzodiazepin-3-yl]-1-piperidinyl}-1,4-butanedione;

(62) (R,S)-4-(4-amino-3,5-dibromophenyl)-2-{{{2-[4-(4-methyl-1-piperazinyl)-1-piperidinyl]ethyl}sulphonyl}amino}-1-{4-[2(2H)-oxo-1,3,4,5-tetrahydro-1,3-benzodiazepin-3-yl]-1-piperidinyl}-1,4-butanedione;

(63) (R,S)-4-(4-amino-3,5-dibromophenyl)-2-{{{2-[4-(4-methyl-1-piperidinyl)-1-piperazinyl]ethyl}sulphonyl}amino}-1-{4-[2(2H)-oxo-1,3,4,5-tetrahydro-1,3-benzodiazepin-3-yl]-1-piperidinyl}-1,4-butanedione;

(64) 2-{[6-amino-2-{{{[1,4']bipiperidinyl-1'-yl}-acetyl}amino}-1-oxo-hexyl]amino}-4-(4-amino-3,5-dibromophenyl)-1-{4-[2(2H)-oxo-1,3,4,5-tetrahydro-1,3-benzodiazepin-3-yl]-1-piperidinyl}-1,4-butanedione;

(65) 4-(4-amino-3,5-dibromophenyl)-2-{[3-(3,5-dibromo-4-hydroxy-phenyl)-2-(1,1-dimethylethoxy-carbonylamino)-1-oxopropyl]amino}-1-{4-[2(2H)-oxo-1,3,4,5-tetrahydro-1,3-benzodiazepin-3-yl]-1-piperidinyl}-1,4-butanedione;

(66) 2-{[2-amino-3-(3,5-dibromo-4-hydroxyphenyl)-1-oxo-propyl]amino}-4-(4-amino-3,5-dibromophenyl)-

1-{4-[2(2H)-oxo-1,3,4,5-tetrahydro-1,3-benzodiazepin-3-yl]-1-piperidinyl}-1,4-butanedione;

(67) (R,S)-3-{{{[1,4']bipiperidinyl-1'-yl}acetyl}amino}-)-4-(3,5-dibromo-4-hydroxyphenyl)-1-{4-[2(2H)-oxo-1,3,4,5-tetrahydro-1,3-benzodiazepin-3-yl]-1-piperidinyl}-1,4-butanedione;

(68) (R,S)-4-(3,5-dibromo-4-hydroxyphenyl)-1-(4-[2(2H)-oxo-1,3,4,5-tetrahydro-1,3-benzodiazepin-3-yl]-1-piperidinyl}-3-{{[4-(4-pyridinyl)-1-piperazinyl]acetyl}amino}-1,4-butanedione; and

(69) (R,S)-4-(3,5-dibromo-4-hydroxyphenyl)-3-{[(4-methyl-1-piperazinyl)acetyl]amino}-1-{4-[2(2H)-oxo-1,3,4,5-tetrahydro-1,3-benzodiazepin-3-yl]-1-piperidinyl}-1,4-butanedione;

or a salt thereof.

6. A physiologically acceptable salt of a compound according to at least one of claims 1 to 5, formed with an inorganic or organic acid or base.

7. A pharmaceutical composition comprising a compound according to at least one of claims 1 to 5 or a physiologically acceptable salt thereof and a pharmaceutical acceptable carrier and/or diluent.

8. A method for treating headache which comprises administering to a host in need of such treatment a therapeutic amount of a compound according to at least one of claims 1 to 5 or a physiologically acceptable salt thereof.

* * * * *